United States Patent
Tao et al.

(10) Patent No.: US 12,049,494 B2
(45) Date of Patent: Jul. 30, 2024

(54) COMPOSITIONS AND METHODS FOR DETECTION OF MALARIA BIOMARKERS

(71) Applicant: THE JOHNS HOPKINS UNIVERSITY, Baltimore, MD (US)

(72) Inventors: Dingyin Tao, Baltimore, MD (US); Brenton McGill, Baltimore, MD (US); Rhoel R. Dinglasan, Gainesville, FL (US)

(73) Assignee: The Johns Hopkins University, Baltimore, MD (US)

( * ) Notice: Subject to any disclaimer, the term of this patent is extended or adjusted under 35 U.S.C. 154(b) by 290 days.

(21) Appl. No.: 15/736,838

(22) PCT Filed: Jun. 17, 2016

(86) PCT No.: PCT/US2016/037968
§ 371 (c)(1),
(2) Date: Dec. 15, 2017

(87) PCT Pub. No.: WO2016/205585
PCT Pub. Date: Dec. 22, 2016

(65) Prior Publication Data
US 2019/0256586 A1    Aug. 22, 2019

Related U.S. Application Data

(60) Provisional application No. 62/180,705, filed on Jun. 17, 2015.

(51) Int. Cl.
| | | |
|---|---|---|
| *A61K 39/00* | (2006.01) | |
| *A61K 39/395* | (2006.01) | |
| *C07K 14/445* | (2006.01) | |
| *C07K 16/20* | (2006.01) | |
| *G01N 33/569* | (2006.01) | |

(52) U.S. Cl.
CPC ............ *C07K 16/205* (2013.01); *A61K 39/00* (2013.01); *A61K 39/39575* (2013.01); *C07K 14/445* (2013.01); *G01N 33/56905* (2013.01); *C07K 2317/565* (2013.01); *G01N 2333/445* (2013.01); *G01N 2800/52* (2013.01)

(58) Field of Classification Search
None
See application file for complete search history.

(56) References Cited

U.S. PATENT DOCUMENTS

| 7,205,159 B2 | 4/2007 | Cole et al. |
| 8,287,719 B2 | 10/2012 | Bhattacharya |
| 8,445,192 B2 | 5/2013 | Gandini |
| 8,623,596 B2 | 1/2014 | Gandini et al. |
| 2004/0087874 A1 | 5/2004 | Schneider |
| 2005/0004346 A1 | 1/2005 | Dziegiel et al. |
| 2010/0279319 A1 | 11/2010 | Stiles |
| 2012/0310113 A1 | 12/2012 | Giddings et al. |
| 2013/0108647 A1 | 5/2013 | Stiles et al. |
| 2015/0037806 A1 | 2/2015 | Pollak et al. |

FOREIGN PATENT DOCUMENTS

| EP | 2696193 A1 | 2/2014 |
| WO | 2010058059 A1 | 5/2010 |
| WO | 2010099607 A1 | 9/2010 |

OTHER PUBLICATIONS

Pierce Immuno Technology Catalog and Handbook, 1990; one page.*
Lloyd et al (Protein Engineering, Design & Selection, 22(3):159-168, 2009).*
Edwards, (J. Mol. Bio 334:103-119, 2003).*
Kanyavuz et al (Nature Reviews Immunology, 19:355-368, 2019).*
Edwards et al (J. Mol. Biol. 334:103-118, 2003).*
Busby et al (bioRxiv preprint first posted online May 19, 2016; pp. 1-26).*
Lipman et al., ILAR Journal, 46(3):258-268, 2005.*
Campbell, A. Laboratory Techniques in Biochemistry and Molecular Biology, Vo.l 23, Chapter 1, 1991.*
Craig et al (2004) TANDEM: matching proteins with tandem mass spectra. Bioinformatics 20:1466-1467.
Maclean et al (2006) General framework for developing and evaluating database scoring algorithms using the TANDEM search engine. Bioinformatics 22:2830-2832.
Tabb et al (2007) MyriMatch: highly accurate tandem mass spectral peptide identification by multivariate hypergeometric analysis. J Proteome Res 6:654-661.
Tanner et al (2005) InsPecT: identification of posttranslationally modified peptides from tandem mass spectra. Anal Chem 77:4626-4639.
Kim et al (2008) Spectral probabilities and generating functions of tandem mass spectra: a strike against decoy databases. J Proteome Res 7:3354-3363.
Elias et al (2007) Target-decoy search strategy for increased confidence in large-scale protein identifications by mass spectrometry. Nat Methods 4:207-214.
Taylor et al (2007) The minimum information about a proteomics experiment (MIAPE). Nat Biotechnol 25:887-893.

(Continued)

Primary Examiner — S. Devi
(74) Attorney, Agent, or Firm — Fox Rothschild LLP

(57) ABSTRACT

The present invention relates to the field of malaria. More specifically, the present invention provides methods and compositions useful for rapidly testing for malaria infection. In one embodiment, a method for identifying the malaria parasite *Plasmodium* in a human subject comprises the steps of (a) incubating a saliva sample obtained from the subject with an antibody that specifically binds PSSP17, wherein the presence of PSSP17 creates one or more antibody: PSSP17 complexes; (b) applying a detection agent that detects the antibody-PSSP17 complexes; and (c) identifying the subject as having the malaria parasite *Plasmodium* where the antibody-PSSP17 complexes are detected.

13 Claims, 28 Drawing Sheets
Specification includes a Sequence Listing.

(56) References Cited

OTHER PUBLICATIONS

Vizcaino et al (2013) The PRoteomics IDEntifications (PRIDE) database and associated tools: status in 2013. Nucleic Acids Res 41:D1063-D1069.
Petersen et al (2011) SignalP 4.0: discriminating signal peptides from transmembrane regions. Nat Methods 8:785-786.
Krogh et al (2001) Predicting transmembrane protein topology with a hidden Markov model: application to complete genomes. J Mol Biol 305:567-580.
Danecek et al (2011) The variant call format and VCFtools. Bioinformatics 27:2156-2158.
Weir et al (1984) Estimating F-statistics for the analysis of population structure. Evolution 38:1358-1370.
Saha et al (2007) Prediction methods for B-cell epitopes. Methods Mol Biol 409:387-394.
Kim et al (2012) Immune epitope database analysis resource. Nucleic Acids Res 40:W525-W530.
Mharakurwa et al (2006) PCR detection of Plasmodium falciparum in human urine and saliva samples. Malaria Journal 5:103.
Wilson et al (2008) Detection of Plasmodium falciparum histidine-rich protein II in saliva of malaria patients. Am J Trop Med Hyg 78:733-735.
Gbotosho et al (2010) Rapid Detection of Lactate Dehydrogenase and Genotyping of Plasmodium falciparum in Saliva of Children with Acute Uncomplicated Malaria. Am J Trop Med Hyg 83:496-501.
Singh et al (2014) Comparison of three PCR-based assays for the non-invasive diagnosis of malaria: detection of Plasmodium parasites in blood and saliva. Eur J Clin Microbiol Infect Dis 33:1631-1639.
Wong (2006) Salivary diagnostics powered by nanotechnologies, proteomics and genomics. JADA 137:313-321.
Fung et al (2012) Quantitative detection of PfHRP2 in saliva of malaria patients in the Philippines. Malar J 11:175.
Sturrock et al (2013) Targeting asymptomatic malaria infections: active surveillance in control and elimination. PLoS Med 10:e1001467.
MalERA Consultive Group on Diagnoses and Diagnostics (2011) A research agenda for malaria eradication: diagnoses and diagnostics. PLoS Med 8:e1000396.
Bastiaens et al (2014) Scale-up of malaria rapid diagnostic tests and artemisinin-based combination therapy: challenges and perspectives in sub-Saharan Africa. PLoS Med 11:e1001590.
Ho et al (2014) Circulating antibodies against Plasmodium falciparum histidine-rich proteins 2 interfere with antigen detection by rapid diagnostic tests. Malar J 13:480.
Teboh-Ewungkem et al (2010) A within-vector mathematical model of Plasmodium falciparum and implications of incomplete fertilization on optimal gametocyte sex ratio. J Theor Biol 264:273-286.
Kast et al (2013) Evaluation of Plasmodium falciparum gametocyte detection in different patient material. Malar J 12:438.
Tangpukdee et al (2009) Malaria diagnosis: a brief review. Korean J Parasitol 47:93-102.
Babiker et al (2008) Gametocytes: insights gained during a decade of molecular monitoring. Trends Parasitol 24:525-530.
Alonso et al (2011) A research agenda to underpin malaria eradication. PLoS Med 8:e1000406.
MalERA Consultive Group on Drugs (2011) A research agenda for malaria eradication: drugs. PLoS Med 8:e1000402.
MalERA Consultive Group on Drugs (2011) A research agenda for malaria eradication: vaccines. PLoS Med 8:e1000398.
Bousema et al (2011) Epidemiology and infectivity of Plasmodium falciparum and Plasmodium vivax gametocytes in relation to malaria control and elimination. Clin Microbiol Rev 24:377-410.
Paul et al (1999) Genetic analysis of Plasmodium falciparum infections on the north-western border of Thailand. Trans R Soc Trop Med Hyg 93:587-593.
Robert et al (1996) Effect of gametocyte sex ratio on infectivity of Plasmodium falciparum to Anopheles gambiae. Trans R Soc Trop Med Hyg 90:621-624.
Silvestrini et al (2010) Protein export marks the early phase of gametocytogenesis of the human malaria parasite Plasmodium falciparum. Mol Cell proteomics 9:1437-1448.
Florens et al (2002) A proteomic view of the Plasmodium falciparum life cycle. Nature 419:520-526.
Hall et al (2005) A comprehensive survey of the Plasmodium life cycle by genomic, transcriptomic, and proteomic analyses. Science 307:82-86.
Khan et al (2005) Proteome analysis of separated male and female gametocytes reveals novel sex-specific Plasmodium biology. Cell 121:675-687.
Sinden (2009) Malaria, sexual development and transmission: retrospect and prospect. Parasitology 136:1427-1434.
Sinden et al (2012) The biology of sexual development of Plasmodium: the design and implementation of transmission-blocking strategies. Malar J 11:60.
Guinet et al (1996) A developmental defect in Plasmodium falciparum male gametogenesis. J Cell Biol 135:269-278.
Furuya et al (2005) Disruption of a Plasmodium falciparum gene linked to male sexual development causes early arrest in gametocytogenesis. Proc Natl Acad Sci U S A 102:16813-16818.
Ubaida Mohien et al (2013) A bioinformatics approach for integrated transcriptomic and proteomic comparative analyses of model and non-sequenced anopheline vectors of human malaria parasites. Mol Cell Proteomics 12:120-131.
Ubaida Mohien et al (2010) MASPECTRAS 2: An integration and analysis platform for proteomic data. Proteomics 10:2719-2722.
Van Schaijk et al (2006) Pfs47, paralog of the male fertility factor Pfs48/45, is a female specific surface protein in Plasmodium falciparum. Mol Biochem Parasitol 149:216-222.
Van Dijk et al (2010) Three members of the 6-cys protein family of Plasmodium play a role in gamete fertility. PLoS Pathog 6:e1000853.
Lal et al (2009) Plasmodium male development gene-1 (mdv-1) is important for female sexual development and identifies a polarised plasma membrane during zygote development. Int J Parasitol 39:755-761.
Ponzi et al (2009) Egress of Plasmodium berghei gametes from their host erythrocyte is mediated by the MDV-1/PEG3 protein. Cell Microbiol 11:1272-1288.
Simon et al (2009) Sexual stage adhesion proteins form multiprotein complexes in the malaria parasite *Plasmodium falciparum*. J Biol Chem 284:14537-14546.
Reininger et al (2009) An essential role for the Plasmodium Nek-2 Nima-related protein kinase in the sexual development of malaria parasites. J Biol Chem 284:20858-20868.
Molina-Cruz et al (2012) Some strains of Plasmodium falciparum, a human malaria parasite, evade the complement-like system of Anopheles gambiae mosquitoes. Proc Natl Acad Sci U S A 109:E1957-E1962.
Manske et al (2012) Analysis of Plasmodium falciparum diversity in natural infections by deep sequencing. Nature 487:375-379.
Anthony et al (2007) Evidence of non-neutral polymorphism in Plasmodium falciparum gamete surface protein genes Pfs47 and Pfs48/45. Mol Biochem Parasitol 156:117-123.
Van Tyne et al (2011) Identification and functional validation of the novel antimalarial resistance locus PF10_0355 in Plasmodium falciparum. PLoS Genet 7:e1001383.
Joice et al (2013) Inferring developmental stage composition from gene expression in human malaria. PLoS Comput Biol 9:e1003392.
Aingaran et al (2012) Host cell deformability is linked to transmission in the human malaria parasite *Plasmodium falciparum*. Cell Microbiol 14:983-993.
Florens et al (2004) Proteomics approach reveals novel proteins on the surface of malaria-infected erythrocytes. Mol Biochem Parasitol 135:1-11.
Trieu et al (2011) Sterile protective immunity to malaria is associated with a panel of novel P. falciparum antigens. Mol Cell Proteomics 10:M111.007948.
Ecker et al (2008) Reverse genetics screen identifies six proteins important for malaria development in the mosquito. Mol Microbiol 70:209-220.

(56) References Cited

OTHER PUBLICATIONS

Ponnudurai et al (1982) The production of mature gametocytes of Plasmodium falciparum in continuous cultures of different isolates infective to mosquitoes. Trans R Soc Trop Med Hyg 76:242-250.

Fivelman et al (2007) Improved synchronous production of Plasmodium falciparum gametocytes in vitro. Mol Biochem Parasitol 154:119-123.

Edwards et al (2009) An Unsupervised, Model-Free, Machine-Learning Combiner for Peptide Identifications from Tandem Mass Spectra. Clin Proteom 5:23-36.

Perkins et al (1999) Probability-based protein identification by searching sequence databases using mass spectrometry data. Electrophoresis 20:3551-3567.

Geer et al (2004) Open mass spectrometry search algorithm. J Proteome Res 3:958-964.

Fung et al., 'Quantitative detection of Pf HRP2 in saliva of malaria patients in the Philippines' Malaria Journal, vol. 11, Article No. 175 (internal pp. 1-9) (2012).

NCBI, NCBI Refence Sequence: XP_001350591.2 (May 27, 2010).

Ngwa et al., 'Changes in the transcriptome of the malaria parasite *Plasmodium falciparum* during the initial phase of transmission from the human to the mosquito' BMC Genomics, vol. 14, Article No. 256 (internal pp. 1-21) (2013).

Tao et al., 'Sex-partitioning of the Plasmodium falciparum stage V gametocyte proteome provides insight into falciparum-specific cell biology' Molecular & Cellular Proteomics, vol. 13, No. 10, pp. 2705-2724 (2014).

\* cited by examiner

| Batch Data | | | | Accession Number | Protein Description | Seq. Cov. (%) | Score | Nr. Proteins | Nr. Peptides | Nr. Spectra | Pb Male (M) Nr. Peptides | Pb Male (M) Nr. Spectra | Pb Female (F) Nr. Peptides | Pb Female (F) Nr. Spectra | M/F Ratio |
|---|---|---|---|---|---|---|---|---|---|---|---|---|---|---|---|
| M2 | M3 | F1 | F3 | | | | | | | | | | | | |
| • | | | | PBANKA_021400 | dynein heavy chain, putative | 13.39 | 996.22 | 1 | 68 | 130 | 1 | 4 | 67 | 126 | 0.015 |
| • | | | | PBANKA_040150 | exportin 1, putative | 9.56 | 137.07 | 1 | 10 | 20 | 4 | 7 | 7 | 13 | 0.575 |
| • | | | | PBANKA_050430 | flagellar outer arm dynein-associated protein, putative | 48.52 | 80.14 | 1 | 3 | 12 | 3 | 11 | 1 | 1 | 3 |
| • | | | | PBANKA_050730 | dynein heavy chain, putative | 26.85 | 2555.88 | 1 | 150 | 373 | 149 | 371 | 2 | 2 | 74.5 |
| • | | | | PBANKA_061400 | conserved Plasmodium protein, unknown function | 4.61 | 51.17 | 1 | 2 | 12 | 1 | 7 | 2 | 5 | 0.5 |
| • | | | | PBANKA_091740 | armadillo repeat protein PF16 | 29.47 | 298.4 | 1 | 15 | 60 | 15 | 51 | 6 | 9 | 2.5 |
| • | • | | | PBANKA_113320 | cdc2-related kinase 2 | 19.8 | 65.09 | 1 | 5 | 8 | 4 | 5 | 2 | 3 | 2 |
| • | | | | PBANKA_130070 | CCp1/LCCL domain-containing protein | 43.66 | 1185.28 | 1 | 63 | 292 | 1 | 1 | 63 | 291 | 0.016 |
| • | | | | PBANKA_135960 | 6-cysteine protein P48/45 | 29.9 | 250.1 | 1 | 15 | 38 | 13 | 31 | 4 | 7 | 3.25 |
| • | | | | PBANKA_142440 | CS domain protein, putative | 16.3 | 94.59 | 1 | 5 | 6 | 2 | 2 | 7 | 13 | 0.286 |
| • | | | | PBANKA_143220 | male development gene 1 | 50.47 | 319.81 | 1 | 16 | 129 | 12 | 43 | 15 | 86 | 0.8 |
| • | | | | PBANKA_145880 | kinesin, putative | 26.88 | 518.63 | 1 | 37 | 71 | 36 | 70 | 1 | 1 | 36 |
| • | • | | | PBANKA_146300 | osmiophilic body protein | 59.41 | 4010.97 | 1 | 186 | 1804 | 7 | 9 | 186 | 1795 | 0.038 |

FIG. 10

Plasmodium falciparum proteins that were identified in pooled saliva from asymptomatic children 5-15 yrs of age from Yaounde, Cameroon (61 proteins)

| Accession Number | Description | MW | TMD | Annotated GO function |
|---|---|---|---|---|
| PF3D7_0111300 | replication factor c protein, putative | 139215 | 0 | ATP binding, nucleoside-triphosphatase activity |
| PF3D7_0216700.1 | conserved Plasmodium protein, unknown function | 167010 | 0 | ATP binding, actin binding, calmodulin binding, motor activity |
| PF3D7_0310500 | DEAD box helicase, putative | 267238 | 0 | ATP binding, helicase activity, nucleic acid binding |
| *PF3D7_0318200 | DNA-directed RNA polymerase II, putative | 278679 | 0 | DNA binding, DNA-directed RNA polymerase activity |
| *#PF3D7_0401900 | acyl-CoA synthetase (ACS6) | 110798 | 1 | long-chain fatty acid-CoA ligase activity |
| PF3D7_0419900 | phosphatidylinositol 4-kinase, putative | 611674 | 17 | phosphotransferase activity, alcohol group as acceptor |
| *#PF3D7_0422300 | alpha tubulin 2 | 49692 | 0 | GTP binding, GTPase activity, structural molecule activity |
| *%#PF3D7_0507800 | conserved Plasmodium protein, unknown function | 177427 | 0 | null |
| PF3D7_0508100 | SET domain protein, putative (SET9) | 195630 | 0 | zinc ion binding |
| #PF3D7_0509400 | RNA polymerase I (RNAPI) | 340680 | 0 | DNA binding, DNA-directed RNA polymerase activity |
| *PF3D7_0510100 | conserved Plasmodium protein, unknown function | 297575 | 0 | null |
| *PF3D7_0511500 | RNA pseudouridylate synthase, putative | 1187597 | 0 | RNA binding, pseudouridine synthase activity |
| *PF3D7_0512600 | Rab GTPase 1b (Rab1b) | 22886 | 0 | GTP binding, GTPase activity, protein binding |
| PF3D7_0528700 | peptidyl-prolyl cis-trans isomerase (CYP23) | 23199 | 0 | cyclosporin A binding, peptidyl-prolyl cis-trans isomerase activity |
| PF3D7_0529800 | conserved Plasmodium protein, unknown function | 225530 | 0 | ATP binding, actin binding, calmodulin binding, motor activity |
| *#PF3D7_0610400 | histone H3 (H3) | 15446 | 0 | DNA binding |
| PF3D7_0632500 | erythrocyte membrane protein 1, PfEMP1 (VAR) | 456921 | 0 | cell adhesion molecule binding, receptor activity |
| PF3D7_0704100 | conserved Plasmodium membrane protein, unknown function | 425269 | 7 | GTP binding, GTPase activity, translation initiation factor activity |

FIG. 11

| Accession Number | Description | MW | TMD | Annotated GO function |
|---|---|---|---|---|
| #PF3D7_0705500 | inositol-phosphate phosphatase, putative | 330704 | 0 | null |
| *PF3D7_0717900 | thioredoxin-like protein | 53378 | 1 | null |
| *PF3D7_0720700 | phosphoinositide-binding protein, putative | 258429 | 4 | phosphatidylinositol binding, protein binding |
| *PF3D7_0818900 | heat shock protein 70 (HSP70) | 73916 | 0 | ATP binding |
| *PF3D7_0831700 | heat shock protein 70 (HSP70-x) | 75054 | 1 | ATP binding |
| *PF3D7_0903200 | Rab GTPase 7 (Rab7) | 23788 | 0 | GTP binding, GTPase activity, protein binding |
| PF3D7_0904100 | adapter-related protein, putative | 161407 | 0 | protein binding |
| *#PF3D7_0906100 | developmental protein, putative | 21852 | 0 | null |
| PF3D7_0907200 | GTPase activator, putative | 134349 | 0 | Rab GTPase activator activity |
| *PF3D7_0917900 | heat shock protein 70 (HSP70-2) | 72388 | 0 | ATP binding |
| ~PF3D7_0927200 | zinc finger protein, putative | 189702 | 0 | RNA binding, zinc ion binding |
| *PF3D7_1015900 | enolase (ENO) | 48678 | 0 | phosphopyruvate hydratase activity |
| PF3D7_1029000 | conserved Plasmodium protein, unknown function, pseudogene | 80885 | 5 | null |
| *PF3D7_1034400 | flavoprotein subunit of succinate dehydrogenase (SDHA) | 70696 | 0 | electron carrier activity, flavin adenine dinucleotide binding, succinate dehydrogenase (ubiquinone) activity |
| *#PF3D7_1102400 | flavoprotein, putative | 78536 | 0 | null |
| *PF3D7_1105600 | translocon component PTEX88 (PTEX88) | 90788 | 0 | null |
| #PF3D7_1134700 | DNA-directed RNA polymerase 1, subunit 2, putative | 175534 | 0 | DNA binding, DNA-directed RNA polymerase activity, ribonucleoside binding |
| *PF3D7_1142100 | conserved Plasmodium protein, unknown function | 324828 | 0 | heat shock protein binding |
| PF3D7_1200200 | rifin (RIF) | 41979 | 1 | null |

FIG. 11 cont'd.

| Accession Number | Description | MW | TMD | Annotated GO function |
|---|---|---|---|---|
| PF3D7_1202300 | dynein heavy chain, putative | 690145 | 0 | microtubule motor activity |
| PF3D7_1207000 | conserved Plasmodium protein, unknown function | 311427 | 0 | ATP binding, actin binding, calmodulin binding, motor activity |
| *PF3D7_1211800 | polyubiquitin (PfpUB) | 42830 | 0 | ATPase activity |
| ~#PF3D7_1215100 | conserved Plasmodium protein, unknown function | 113034 | 1 | ATP binding, actin binding, calmodulin binding, motor activity |
| PF3D7_1216000 | serine--tRNA ligase, putative | 73273 | 0 | ATP binding, serine-tRNA ligase activity |
| *#PF3D7_1216900 | DNA-binding chaperone, putative | 111066 | 0 | DNA binding, heat shock protein binding |
| #%PF3D7_1218800 | secreted ookinete protein, putative (PSSP17) | 39632 | 0 | null |
| *PF3D7_1231100 | Rab GTPase 2 (RAB2) | 24424 | 0 | GTP binding, GTPase activity, protein binding |
| *#PF3D7_1235700 | ATP synthase subunit beta, mitochondrial | 58395 | 0 | hydrogen ion transporting ATP synthase activity, rotational mechanism, hydrogen-exporting ATPase activity, phosphorylative mechanism, nucleotide binding, proton-transporting ATPase activity, rotational mechanism |
| *#PF3D7_1239900 | vesicle fusion and protein sorting subunit 16, putative (VPS16) | 120301 | 0 | null |
| #PF3D7_1313500 | conserved Plasmodium membrane protein, unknown function | 209077 | 14 | hydrolase activity, triglyceride lipase activity |
| PF3D7_1318300 | conserved Plasmodium protein, unknown function | 214848 | 0 | calcium ion binding |
| #PF3D7_1319200 | conserved Plasmodium protein, unknown function | 103852 | 0 | flavin adenine dinucleotide binding |
| #PF3D7_1325900 | conserved Plasmodium protein, unknown function | 326146 | 0 | ATP binding, actin binding, calmodulin binding, motor activity |

FIG. 11 cont'd.

| Accession Number | Description | MW | TMD | Annotated GO function |
|---|---|---|---|---|
| ~PF3D7_1327300 | conserved Plasmodium protein, unknown function | 205479 | 0 | ATP binding, actin binding, calmodulin binding, motor activity |
| PF3D7_1337200 | 1-deoxy-D-xylulose 5-phosphate synthase | 140232 | 1 | catalytic activity |
| #PF3D7_1337500 | conserved Plasmodium protein, unknown function | 393260 | 0 | calcium ion binding, receptor activity |
| *PF3D7_1342600 | myosin A (MyoA) | 92279 | 0 | ATP binding, actin binding, motor activity |
| *#PF3D7_1353000 | tryptophan-rich antigen, pseudogene | 96248 | 0 | null |
| #PF3D7_1411400 | plastid replication-repair enzyme (PREX) | 235821 | 0 | 3'-5' exonuclease activity, ATP binding, DNA binding, DNA helicase activity, DNA primase activity, DNA-directed DNA polymerase activity |
| PF3D7_1421300 | conserved Plasmodium protein, unknown function | 122990 | 1 | peptidase activity, protein binding, serine-type endopeptidase activity |
| PF3D7_1434200 | calmodulin (CAM) | 16931 | 0 | calcium ion binding, enzyme binding |
| PF3D7_1443800 | zinc finger protein, putative | 48092 | 0 | nucleic acid binding, protein binding, zinc ion binding |
| PF3D7_1452200 | aminomethyltransferase, putative | 62353 | 0 | null |

*Asexual stage proteins (26 proteins): Several of these proteins are also shared with gametocyte stages
~Gametocyte stage I-II proteins (5 proteins)
Unmarked cells: stage V gametocyte proteins
Most abundant proteins by spectral count
%Proteins selected for MRM studies: Most abundant gametocyte and asexual proteins in pooled saliva

FIG. 11 cont'd.

|  | Zambia | | Cameroon | | |
| --- | --- | --- | --- | --- | --- |
|  | 20990 | 21059 | D497 | C100 | |
| PF3D7_1218800 PSSP17 |  |  |  |  | kDa<br>–35<br>–25 |
| Integrated Peak Area | 820 | 703 | 1169 | 1340 | |
| Peak Area Ratio | 0.04 | 0.04 | 0.03 | 0.06 | |
| SD Bioline RDT | Neg | Pos | - | - | |
| Pfs25 RTPCR | - | - | Neg | Neg | |
| PfCytB PCR | Neg | Neg | - | - | |
| Microscopy | Neg | Neg | Neg | Neg | |

FIG. 13

```
CLUSTAL multiple sequence alignment by MUSCLE (3.8)

Signal Peptide
Pvpssp17.seq    MPFHFSKTWCLIFLVPYFKTQIECYQDDPKL--PECDVSIDTAICINNGQKILLPEAKPY
Pfpssp17.seq    MLLYLYKIWYLILLWLYTHNQYKC--DLRLKPPECDVSIDTSICINNGQKILLPSAKPY
                 :: * * **:*:* :.*  *  *  ********:***********.***

Pvpssp17.seq    GISAHIKFDSTSAVDATGNRNHAVGNFFASTGFGGMGNSSLFRENYIYIPHGDEYFETVD
Pfpssp17.seq    GISTHITPDSLMPVDSTGNRNHAHGKFFASSGFGGIGNSALFRQNYIYIPHGDEYFESVD
                ***:**.*.**  ****:***** *:****:***:**:***:***************:**

Pvpssp17.seq    FSYTFFIYLLEDELSIKNNVEEMFCPVIHKGIIKDEVQESSPAILINAKNGRIKIVLSTS
Pfpssp17.seq    FSYTFFIYLLQDEISRKNNMEEKFCPVIHKGIIKDKIQESSPAILINTKNGRIKIVLSTS
                **********::** ***:**:***********::*********.*************

Pvpssp17.seq    SSTNSAGEEFLSNFKLRRHQWYHVAVVRHINHVRLFVNGILDSSFLTEGITKTNDFPIYI
Pfpssp17.seq    SSTNSAGEEFLSNFKLRHHQWYHMTVVRHINHVRLFVDGILDSSFLTEGITKTNDSPIYI
                *****************:*****  :***********:****************. ***

Pvpssp17.seq    GGAPYSVESCDFPFLLDELKVYNLSLGVDHIQSEAASTLNGVEPSFIYFGCFHCDINNAI
Pfpssp17.seq    GGAPYSVDSCDFPFLLDELKIYNLSIGTDQIQSEASASLSGIEPSFIYFGCFHCDMNTAI
                *******:************:****:*.*:****:::*.*:************* *.**

Pvpssp17.seq    LSCPNNYHLCNKVELYIGVYNVMRKFSLNINNLILPFSPENHTGIGVCCADI     SEQ ID NO:89
Pfpssp17.seq    LSCPNNYHLCNKMELYIGVYNVLRKFSLDVNNIILPYSSESNLGIGICCTDI     SEQ ID NO:90
                ************:*********:****::.**:***:*.*.* ***:**:**
```

FIG. 23

COMPOSITIONS AND METHODS FOR DETECTION OF MALARIA BIOMARKERS

CROSS-REFERENCE TO RELATED APPLICATIONS

This application is a 35 U.S.C. § 371 U.S. national entry of International Application PCT/US2016/037968, having an international filing date of Jun. 17, 2016, which claims the benefit of U.S. Provisional Application No. 62/180,705, filed Jun. 17, 2015, the content of each of the aforementioned applications is herein incorporated by reference in their entirety.

FIELD OF THE INVENTION

The present invention relates to the field of malaria. More specifically, the present invention provides methods and compositions useful for rapidly testing for malaria infection.

INCORPORATION-BY-REFERENCE OF MATERIAL SUBMITTED ELECTRONICALLY

This application contains a sequence listing. It has been submitted electronically via EFS-Web as an ASCII text file entitled "P13038-04_ST25.txt." The sequence listing is 40,507 bytes in size, and was created on Jun. 16, 2016. It is hereby incorporated by reference in its entirety.

BACKGROUND OF THE INVENTION

Malaria control efforts have yielded significant progress toward reducing the burden of malaria. An estimated 274 million fewer cases and 1.1 million fewer malaria-related deaths were reported in the last decade (WHO, 2013). However, expanding drug resistance, the cost of sustained control efforts and the risk of malaria resurgence in countries that have reached the pre-elimination phase have resulted in the generation of road maps on how to maintain the momentum toward reaching the goal of elimination and eradication (WHO, 2007; Alonso, et al., 2011; malERA Consultative Group 2011).

Individuals presenting with malaria symptoms must have the diagnosis confirmed by expert microscopy or RDT prior to treatment. Malaria RDTs detect specific *Plasmodium* antigens in blood and commonly use one or more of three target antigens: histidine-rich protein 2 (HRP2), lactate dehydrogenase (LDH) and aldolase. HRP2 is expressed only by *Plasmodium falciparum* (Pf) and is the most widely used target antigen. LDH and aldolase are expressed across all *Plasmodium* species but appear to have lower diagnostic accuracy among current RDTs that incorporate these two antigens (FIND, 2012). In fact, a recent comparative analysis of WHO-qualified RDTs demonstrated significant variability in performance for many of the widely used RDTs (WHO, 2013). Of the 42 RDTs that qualified for the study, only four had detection rates above 90% at the WHO recommended lower limit of detection (200 parasites/µL) (Perkins et al., 2008).

As national malaria control programs consider strategies and tools to support malaria elimination (malERA Consultative Group, 2011), it is imperative that the malaria community reassess diagnostic research priorities in pre-elimination settings because the epidemiology of malaria changes significantly as regions transition from control to pre-elimination phase activities (Cotter, 2013). Infections become localized in defined geographic areas and are more frequently imported from higher-transmission regions. Importantly, a larger proportion of ongoing transmission is attributed to low parasite density and subclinical infection, which are not readily detected by currently available RDTs or microscopy (Bottius, et al., 1996; Laishram, et al., 2013; FIND report 2012 Round 4). As such, it has been argued that passive case detection strategies based at health care facilities need to be augmented with active infection (asymptomatic) detection strategies using more sensitive diagnostic tools.

SUMMARY OF THE INVENTION

The present invention is based, at least in part, on the development of a non-invasive malaria rapid diagnostic test (RDT). The test comprises the detection of female-specific gametocyte proteins in saliva. In one embodiment, the female-specific gametocyte protein biomarkers comprises PF3D7_1218800. This gene was originally referred to as "*Plasmodium* secreted ookinete protein 17, or PSOP17" and was referred to as such in previous scientific publications. However, given its expression in gametocytes, this annotation was no longer correct, and we refer to the protein herein as PSSP17, *Plasmodium* sexual stage protein 17. In another embodiment, the protein biomarker comprises PF3D7_0507800. The present invention can also comprise the detection of histidine rich protein 2 (HRP2). In further embodiments, the female-specific gametocyte protein biomarkers include one or more of PF3D7_0111300 (replication factor c protein, putative), PF3D7_0216700.1 (conserved *Plasmodium* protein, unknown function), PF3D7_0310500 (DEAD box helicase, putative), PF3D7_0318200 (DNA-directed RNA polymerase II, putative), PF3D7_0401900 (acyl-CoA synthetase (ACS6)), PF3D7_0419900 (phosphatidylinositol 4-kinase, putative), PF3D7_0422300 (alpha tubulin 2), PF3D7_0507800 (conserved *Plasmodium* protein, unknown function), PF3D7_0508100 (SET domain protein, putative (SETS)), PF3D7_0509400 (RNA polymerase I (RNAPI)), PF3D7_0510100 (conserved *Plasmodium* protein, unknown function), PF3D7_0511500 (RNA pseudouridylate synthase, putative), PF3D7_0512600 (Rab GTPase 1b (Rab1b)), PF3D7_0528700 (peptidyl-prolyl cis-trans isomerase (CYP23)), PF3D7_0529800 (conserved *Plasmodium* protein, unknown function), PF3D7_0610400 (histone H3 (H3)), PF3D7_0632500 (erythrocyte membrane protein 1, PfEMP1 (VAR)), PF3D7_0704100 (conserved *Plasmodium* membrane protein, unknown function), PF3D7_0705500 (inositol-phosphate phosphatase, putative), PF3D7_0717900 (thioredoxin-like protein), PF3D7_0720700 (phosphoinositide-binding protein, putative), PF3D7_0818900 (heat shock protein 70 (HSP70)), PF3D7_0831700 (heat shock protein 70 (HSP70-x)), PF3D7_0903200 (Rab GTPase 7 (Rab7)), PF3D7_0904100 (adapter-related protein, putative), PF3D7_0906100 (developmental protein, putative), PF3D7_0907200 (GTPase activator, putative), PF3D7_0917900 (heat shock protein 70 (HSP70-2)), PF3D7_0927200 (zinc finger protein, putative), PF3D7_1015900 (enolase (ENO)), PF3D7_1029000 (conserved *Plasmodium* protein, unknown function, pseudogene), PF3D7_1034400 (flavoprotein subunit of succinate dehydrogenase (SDHA)), PF3D7_1102400 (flavoprotein, putative), PF3D7_1105600 (translocon component PTEX88 (PTEX88)), PF3D7_1134700 (DNA-directed RNA polymerase 1, subunit 2, putative), PF3D7_1142100 (conserved *Plasmodium* protein, unknown function), PF3D7_1200200 (rifin (RIF)), PF3D7_1202300 (dynein heavy chain, putative), PF3D7_1207000 (conserved *Plasmodium* protein, unknown function), PF3D7_1211800 (polyubiquitin (PfpUB)), PF3D7_1215100 (conserved *Plasmodium* protein, unknown function), PF3D7_1216000 (serine—tRNA ligase, putative), PF3D7_1216900 (DNA-binding chaperone, putative), PF3D7_1218800 (secreted ookinete protein, putative (PSSP17)), PF3D7_1231100 (Rab GTPase 2 (RAB2)), PF3D7_1235700 (ATP synthase subunit beta, mitochondrial), PF3D7_1239900 (vesicle fusion and protein sorting subunit 16, putative (VPS16)), PF3D7_1313500 (conserved *Plasmodium* membrane protein, unknown function), PF3D7_1318300 (conserved *Plasmodium* protein, unknown function), PF3D7_1319200 (conserved *Plasmodium* protein, unknown function), PF3D7_1325900 (conserved *Plasmodium* protein, unknown function), PF3D7_1327300 (conserved *Plasmodium* protein, unknown function), PF3D7_1337200 (1-deoxy-D-xylulose 5-phosphate synthase), PF3D7_1337500 (conserved *Plasmodium* protein, unknown function), PF3D7_1342600 (myosin A (MyoA)), PF3D7_1353000 (tryptophan-rich antigen, pseudogene), PF3D7_1411400 (plastid replication-repair enzyme (PREX)), PF3D7_1421300 (conserved *Plasmodium* protein, unknown function), PF3D7_1434200 (calmodulin (CAM)), PF3D7_1443800 (zinc finger protein, putative), and PF3D7_1452200 (aminomethyltransferase, putative).

The present invention provides antibodies to PSSP17 that can be used in the methods and compositions described herein. In one embodiment, an antibody or fragment thereof specifically binds to the *Plasmodium* female-specific gametocyte biomarker protein, PSSP17. *Plasmodium* species include *P. falciparum, P. vivax, P. ovale, P. malariae* and *P. knowlesi*. The antibodies can specifically bind to PSSP17 from one or more of *P. falciparum, P. vivax, P. ovale, P. malariae* and *P. knowlesi*. In a specific embodiment, the antibodies specifically bind to *P. vivax* PSSP17. In another embodiment, the antibodies specifically bind to *P. falciparum* PSSP17.

In certain embodiments, the present invention provides an antibody or fragment thereof that specifically binds SEQ ID NO:8, which is the synthetic gene sequences that is codon optimized for *E. coli* expression. This sequence was also used as the antigen for creating the monoclonal antibodies designated as 10E2B7 and 27C9B5. In a specific embodiment, an anti-PSSP17 antibody comprises a variable heavy chain comprising SEQ ID NO:20. In another embodiment, an anti-PSSP17 antibody comprises a variable light chain comprising SEQ ID NO:40. In a further embodiment, an anti-PSSP17 antibody comprises (a) a variable heavy chain comprising SEQ ID NO:20; and (b) a variable light chain comprising SEQ ID NO:40.

In another specific embodiment, an anti-PSSP17 antibody comprises a variable heavy chain comprising SEQ ID NO:60. In another embodiment, an anti-PSSP17 antibody comprises a variable light chain comprising SEQ ID NO:80. In a further embodiment, an anti-PSSP17 antibody comprises (a) a variable heavy chain comprising SEQ ID NO:60; and (b) a variable light chain comprising SEQ ID NO:80. The variable heavy and light chains can be combined, e.g., the variable heavy chain from mAb 10E2B7 can be used in combination with the variable light chain from mAb 27C9B5, and vice versa.

A variable heavy chain of an anti-PSSP17 antibody can also comprise the complementarity determining regions (CDRs) shown in SEQ ID NOS:24, 25, and 27 (mAb 10E2B7) or SEQ ID NOS:63, 65 and 67 (mAb 27C9B5), or combinations of the foregoing. In other embodiments, a variable light chain of an anti-PSSP17 antibody can also comprise the CDRs shown in SEQ ID NOS:43, 45, and 47 (mAb 10E2B7) or SEQ ID NOS:83, 85 and 87 (mAb 27C9B5), or combinations of the foregoing.

Thus, in particular embodiments, an antibody comprises (a) a variable heavy chain comprising the complementarity determining regions (CDRs) shown in SEQ ID NOS:23, 25 and 27; and (b) a variable light chain comprising the CDRs shown in SEQ ID NOS:43, 45 and 47. In other embodiments, an antibody comprises (a) a variable heavy chain comprising the CDRs shown in SEQ ID NOS:63, 65 and 67; and (b) a variable light chain comprising the CDRs shown in SEQ ID NOS:83, 85 and 87.

The antibodies can further comprise any one or more of the framework regions described herein. It is understood that SEQ ID NOS: 9-88 provided in the sequence listing are embodiments of the present invention and can be used to design an anti-PSSP17 antibody. For recombinant expression of the antibodies, the leader sequences described herein can be utilized. It is also understood that the composition (e.g., kits) and method claims can be utilized and practice with any of the antibody embodiments described herein.

In another aspect, the present invention provides kits. The kits can be used as described herein, specifically, to determine whether a subject has a malaria parasite (e.g., *P. falciparum* or *P. vivax*). In one embodiment, a kit comprises an anti-PSSP17 antibody described herein. The antibody can comprise a detectable label or a label is provided in the kit and conjugated to the antibody by the end user. Alternatively, a secondary antibody is provided that comprises a detectable label. In other embodiments, a kit comprises a second anti-PSSP17 antibody that can be labeled (or is pre-labeled) and used as a detection reagent. Thus, in one embodiment, a kit can comprise (a) at least one antibody that specifically binds PSSP17; and (b) a detection reagent for detecting the presence of PSSP17 in a saliva sample obtained from a subject suspected of having a malaria parasite.

In another embodiment, the kit can further comprise an antibody that specifically binds histidine rich protein 2 (HRP2). The antibody can comprise a detectable label or a label is provided in the kit and conjugated to the antibody by the end user. Alternatively, a secondary antibody is provided that comprises a detectable label. In other embodiments, a kit comprises a second anti-HRP2 antibody that can be labeled (or is pre-labeled) and used as a detection reagent. Thus, in another embodiment, a kit can further comprise (c) at least one antibody that specifically binds histidine rich protein 2 (HRP2); and (d) a detection reagent for detecting the presence of HRP2 in a saliva sample obtained from a subject suspected of having a malaria parasite.

In other embodiments, the kits can comprise a positive control for PSSP17, wherein the positive control is the amino acid sequence shown in SEQ ID NO:8. In specific embodiments, the kits comprising an anti-PSSP17 antibody comprise an antibody that specifically binds SEQ ID NO:8. In a more specific kit embodiment, the at least one antibody that specifically binds PSSP17 comprises (a) a variable heavy chain comprising SEQ ID NO:20; and (b) a variable light chain comprising SEQ ID NO:40. In another kit embodiment, the at least one antibody that specifically binds PSSP17 comprises (a) a variable heavy chain comprising SEQ ID NO:60; and (b) a variable light chain comprising SEQ ID NO:80.

In yet another kit embodiment, the at least one antibody that specifically binds PSSP17 comprises (a) a variable heavy chain comprising the complementarity determining regions (CDRs) shown in SEQ ID NOS:23, 25 and 27; and (b) a variable light chain comprising the CDRs shown in SEQ ID NOS:43, 45 and 47. In a further kit embodiment, the at least one antibody that specifically binds PSSP17 comprises (a) a variable heavy chain comprising the CDRs shown in SEQ ID NOS:63, 65 and 67; and (b) a variable light chain comprising the CDRs shown in SEQ ID NOS:83, 85 and 87.

The kits of the present invention can further comprise a lateral flow immunoassay device. In certain embodiments, the kit comprises a lateral flow strip. The lateral flow strip can be used as part of a sandwich ELISA. An antibody that specifically binds PSSP17 can be labeled with biotin and streptavidin can be deposited at the test line of the strip. A second antibody that specifically binds PSSP17 can be used as a detection reagent. It can be pre-deposited on the strip itself or provided in the kit to be incubated with the sample (along with the primary PSSP17 antibody (i.e., capture reagent) prior to loading on to the lateral flow strip. In one embodiment, the antibodies can be labeled (e.g., with biotin for the capture reagent or with a detectable label for the detection reagent) by the user prior to incubation with the sample. Alternatively, the antibodies pre-conjugated and/or pre-labeled. In a further embodiment, IgG can be deposited at the control line of the lateral flow strip. Indeed, the kit can utilize many different forms of lateral flow and such embodiments are described herein and known to those of ordinary skill in the art.

In a specific embodiment, a rapid diagnostic test kit for detection of the malaria parasite *Plasmodium* comprises (a) a plurality of capture reagents that bind to one or more of the proteins listed in FIG. 11; (b) a detection agent for detecting the presence of one or more of the proteins listed in FIG. 11 that bind to the capture reagents; (c) a container for collecting a sample from an individual; and (d) instructions for collecting a sample from the individual, incubating the plurality of capture reagents, detecting the presence of the capture reagents bound to the proteins. In another specific embodiment, the one or more proteins listed in FIG. 11 comprises PF3D7_1218800 (PSSP17). In yet another embodiment, the one or more proteins listed in FIG. 11 further comprises PF3D7_0507800. In other embodiments, the kit further comprises a capture reagent that binds to histidine rich protein 2 (HRP2). In particular embodiments, the capture reagent is an antibody. The kits can further comprise a positive control protein comprising SEQ ID NO:8.

In another aspect, the present invention provides methods for identifying whether a subject has a malaria parasite. The subject can be asymptomatic or symptomatic for malaria. Such methods rely, in part, on the detection of a female-specific gametocyte protein in a saliva sample obtained from the subject. The method can also comprise detecting HRP2. In one embodiment, a method for identifying the malaria parasite *Plasmodium* in a human subject comprises the steps of (a) incubating a saliva sample obtained from the subject with an antibody that specifically binds PSSP17, wherein the presence of PSSP17 creates one or more antibody: PSSP17 complexes; (b) applying a detection agent that detects the antibody-PSSP17 complexes; and (c) identifying the subject as having the malaria parasite *Plasmodium* where the antibody-PSSP17 complexes are detected. Subject identified as having a malaria parasite (e.g., *P. falciparum, P. vivax*, or the like) can be treated with anti-malarials. The choice of anti-malarial depends on the malaria control policies of the nation where the subject is located. Such anti-malarials can include, but are not limited to, quinine, chloroquine, amodiaquine, roguanil, chlorproguanil, proguanil, cycloquanil, pyrimethamine, sulfadoxine, pyrimethamine-sulfadoxine, pyrimethamine-dapsone, primaquine, amopyroquine, chlorproquanil, quinidine, tetracycline, dapsone, doxycycline, clindamycin, sulphonamides, arteflene, mefloquine, halofantrine, bulaquine, artemisinin, artemether, arteether, atovaquone, lumefantrine, dihydroartemisinin, piperaquine, artesunate, pyronaridine, azithromycin, tafenoquine, trimethoprim, sulfamethoxazole, artemisone, ferroquine, fosmidomycin, tinidazole, naphthoquine, methylene blue, (+)-erythromefloquine, tert-butyl isoquine, trioxaquine, an endoperoxide, a dihydrofolate reductase inhibitor, or a dihydroorotate dehydrogenase inhibitor.\

Thus, in other embodiments, a method for treating a human subject identified as having the malaria parasite *Plasmodium* comprises the steps of (a) incubating a saliva sample obtained from the subject with an antibody that specifically binds PSSP17, wherein the presence of PSSP17 creates one or more antibody: PSSP17 complexes; (b) applying a detection agent that detects the antibody-PSSP17 complexes; and (c) administering a malaria treatment to the subject where the antibody-PSSP17 complexes are detected. In particular embodiments, the present invention can be used to determine parasite clearance after drug treatment, specifically for stages that are responsible for transmission to mosquitoes.

Furthermore, the compositions and methods of the present invention can be used across the globe for weekly screening in schools in malaria endemic countries: Teachers/administrators can conduct weekly screening of all children across the high-risk age groups for malaria (typically ages 5-16 years across much of Sub-Saharan Africa, though the targeted population can change according to local malaria transmission. Children who are determined to be positive, yet asymptomatic, can be provided anti-malarials to clear the parasite reservoir. The choice of antimalarial used is dependent on national malaria control policies.

The present invention can also be used in routine screening in oil, logging, and plantation establishments in malaria endemic countries. Clinical/human resources staff can collect samples from workers to prevent malaria incidence. This screening method can be extended to workers' families and surrounding villages. Individuals found to be harboring parasites can be provided anti-malarials.

The compositions and methods of the present invention can further be used as a rapid test for epidemiological surveys/studies in developing countries by research groups (government/academic) to estimate subclinical carriage prevalence. Furthermore, clinicians can use the rapid test in private practice in developing and developed countries for patients.

The present invention can also be used a rapid test for screening travelers entering into a country at known ports of entry (air, land, sea). This is especially important for countries that have reached the malaria elimination phase or have been verified to be "malaria-free" to prevent reintroduction. Screening can also be conducted in developed countries to screen carrier entry following holiday/work travel to malaria endemic countries.

The present invention can further be included as a component of a work travel kit for high-level members of multinational companies who are assigned to oversee operations in malaria endemic countries. In addition, the present invention can be included as a component of a holiday travel kit for all members of society. The kit allows for easy, unambiguous self-diagnosis/screening. The individual can either take anti-malarials included in the travel kit or obtained from a local dispensary.

BRIEF DESCRIPTION OF THE FIGURES

FIG. 10. A PSMA reanalysis of the existing *Plasmodium berghei* male and female gametocyte proteome using the current iteration of the genome revealed that many sex-specific proteins were shared between males and females. The relative enrichment of unique peptides was examined in the respective male and female batches from the original study to determine the degree of expression of these shared proteins.

FIG. 11. *Plasmodium falciparum* proteins that were identified in pooled saliva from asymptomatic children 5-15 yrs of age from Yaounde, Cameroon (61 proteins).

FIG. 13. Comparative analysis of detection approaches used to identify asymptomatic carriers. We compared the ability of anti-PSSP17 antibodies to detect antigen in 12 µl of filtered but unconcentrated saliva proteins (12 µg/well) with MRM-based mass spectrometry, RDT, RTPCR, PCR and microscopy. For MRM analyses of saliva, we calculated the Peak Area Ratio, which is the ratio of the target analyte's integrated peak area over internal standard's integrated peak area. From blood samples, we used the SD Bioline RDT, RTPCR amplification of the Pfs25 gametocyte transcript, PCR amplification of parasite cytochrome B (CytB) gene and microscopy.

FIG. 23. Alignment of *P. falciparum* PSSP17 and its ortholog in *P. vivax*. Signal peptide shown as an arrow and the region used to raise monoclonal antibodies is shown as a bar.

DETAILED DESCRIPTION OF THE INVENTION

Figures 1A, 1B, 1C:
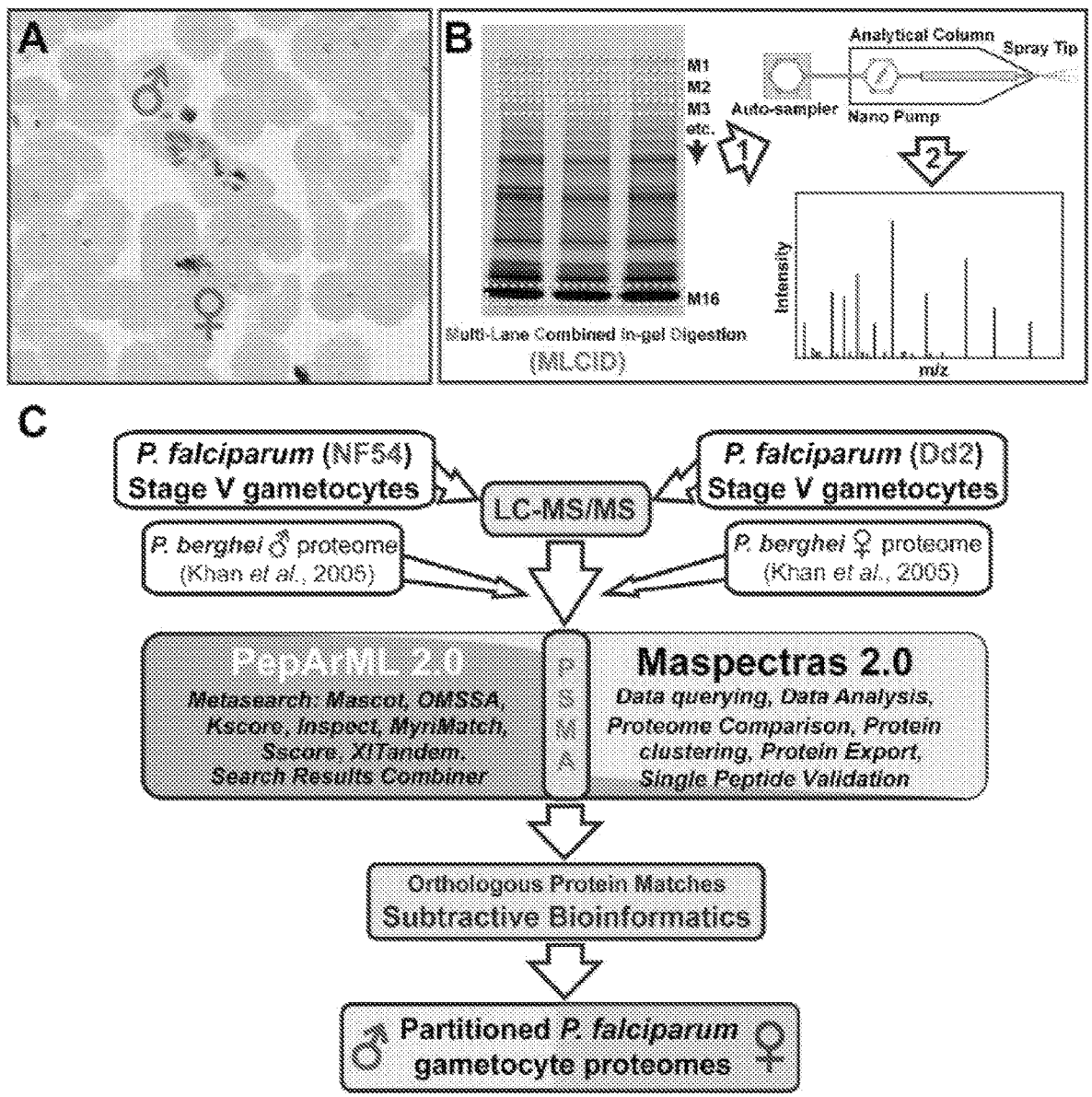
FIG. 1A-1C. Workflow for *Plasmodium falciparum* male and female protein partition analysis using proteomics and bioinformatics analysis. (A) Gametocyte sex ratios were determined using differential staining and microscopy. Improved R66 Giemsa is diluted 1:40 in Sorensen buffer (pH 7.2) and used to stain a methanol-fixed, thin smear of stage V (mature) gametocytes from a gametocyte culture. Gametocytes can be differentiated according to five classical parameters (Carter & Graves, 1988) as well as by differential Giemsa staining patterns. Males (M) appear pink with no distinct nucleus and females (F) appear blue with a distinct nucleus. (B) Proteomics workflow. Soluble and membrane proteins were extracted for Multi-Lane Combined In-gel Digestion (MLCID, see methods) prior to Chip-based nano-HPLC MS/MS analysis. (C) Bioinformatics workflow. LC MS/MS data from NF54 and Dd2 is searched on PepArML meta search engine with 6 search engines. *P. berghei* MS/MS male proteome and MS/MS female proteome is also uploaded to PepArML and Maspectras2. The result is combined in PepArML by unsupervised machine learning and stored in Maspectras2 and queried for analysis. Proteome results are then compared to the *P. berghei* MS/MS male proteome and MS/MS female proteome as shown. This comparison is done by orthologous protein matches and a subtractive bioinformatics approach, producing partitioned proteomes for male and female gametocytes.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "antigen" is generally used in reference to any substance that is capable of reacting with an antibody. More specifically, as used herein, the term "antigen" refers to a synthetic peptide, polypeptide, protein or fragment of a polypeptide or protein, or other molecule which elicits an antibody response in a subject, or is recognized and bound by an antibody.

As used herein, the term "biomarker" refers to a molecule that is associated either quantitatively or qualitatively with a biological change. Examples of biomarkers include polypeptides, proteins or fragments of a polypeptide or protein; and polynucleotides, such as a gene product, RNA or RNA fragment; and other body metabolites. In certain embodiments, a "biomarker" means a compound that is differentially present in a biological sample from a subject or a group of subjects having a first phenotype (e.g., a subject having the malaria parasite *Plasmodium*) as compared to a biological sample from a subject or group of subjects having a second phenotype (e.g., a subject having the malaria parasite *Plasmodium*). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). Alternatively, the differential presence of a biomarker can be characterized by a -fold change in level including, for example, a level that is increased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold; or that is decreased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold. A biomarker is preferably differentially present at a level that is statistically significant (e.g., a p-value less than 0.05 and/or a q-value of less than 0.10 as determined using, for example, either Welch's T-test or Wilcoxon's rank-sum Test).

The term "one or more of" refers to combinations of various biomarker proteins. The term encompasses 1, 2, 3, 4, 5, 6, 7, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40 . . . N, where "N" is the total number of biomarker proteins in the particular embodiment. The term also encompasses at least 1, at least 2, at least 3, at least 4, at least 5, at least 6, at least 7, at least 8, at least 9, at least 10, at least 11, at least 12, at least 13, at least 15, 16, 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40 . . . N. It is understood that the recitation of biomarkers herein includes the phrase "one or more of" the biomarkers and, in particular, includes the "at least 1, at least 2, at least 3" and so forth language in each recited embodiment of a biomarker panel.

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. As used herein, the terms "specific binding" or "specifically binding" when used in reference to the interaction of an antibody and a protein or peptide means that the interaction is dependent upon the presence of a particular structure (i.e., the epitope) on the protein.

As used herein, the terms "binding agent specific for" or "binding agent that specifically binds" refers to an agent that binds to a biomarker and does not significantly bind to unrelated compounds. Examples of binding agents that can be effectively employed in the disclosed methods include, but are not limited to, proteins and antibodies, such as monoclonal or polyclonal antibodies, or antigen-binding fragments thereof. In certain embodiments, a binding agent binds a biomarker (e.g., a polypeptide biomarker) with an affinity constant of, for example, greater than or equal to about $1\times10^{-6}$ M.

By "antibody" is meant any immunoglobulin polypeptide, or fragment thereof, having immunogen binding ability. As used herein, the terms "antibody fragments", "fragment", or "fragment thereof" refer to a portion of an intact antibody. Examples of antibody fragments include, but are not limited to, linear antibodies; single-chain antibody molecules; Fc or Fc' peptides, Fab and Fab fragments, and multi-specific antibodies formed from antibody fragments. In most embodiments, the terms also refer to fragments that bind an antigen of a target molecule (e.g., a biomarker protein described herein) and can be referred to as "antigen-binding fragments." As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies that specifically binds the target antigen.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "an effective amount" is meant the amount of a required to ameliorate the symptoms of a disease relative to an untreated patient. The effective amount of active compound(s) used to practice the present invention for therapeutic treatment of malaria varies depending upon the manner of administration, the age, body weight, and general health of the subject. Ultimately, the attending physician or veterinarian will decide the appropriate amount and dosage regimen. Such amount is referred to as an "effective" amount.

The term "malaria" includes the art recognized condition known as "malaria" e.g., disorders which are caused by a protozoan of the genus *Plasmodium*. Malaria is generally characterized by symptoms such as headache, malaise, anemia, splenomegaly, and paroxyms with cold, hot, and wet stages and is transmitted by mosquitoes. In a further embodiment, the protozoan is selected from the group consisting of: *P. falciparum, P. vivax, P. ovale, P. malariae*, and *P. knowlesi*.

Examples of malaria treatment or anti-malarials include, but are not limited to, quinine, chloroquine, amodiaquine, roguanil, chlorproguanil, proguanil, cycloquanil, pyrimethamine, sulfadoxine, pyrimethamine-sulfadoxine, pyrimethamine-dapsone, primaquine, amopyroquine, chlorproquanil, quinidine, tetracycline, dapsone, doxycycline, clindamycin, sulphonamides, arteflene, mefloquine, halofantrine, bulaquine, artemisinin, artemether, arteether, atovaquone, lumefantrine, dihydroartemisinin, piperaquine, artesunate, pyronaridine, azithromycin, tafenoquine, trimethoprim, sulfamethoxazole, artemisone, ferroquine, fosmidomycin, tinidazole, naphthoquine, methylene blue, (+)-erythromefloquine, tert-butyl isoquine, trioxaquine, an endoperoxide, a dihydrofolate reductase inhibitor, or a dihydroorotate dehydrogenase inhibitor. In particular embodiments, the present invention can be used to determine parasite clearance after drug treatment, specifically for stages that are responsible for transmission to mosquitoes. Other uses of the present invention in conjunction with treatment are described herein.

The term "solid support", as used herein, refers to any composition and/or material that is capable of immobilizing a compound including, but not limited to, immobilizing an antibody (i.e., for example, an antibody that binds to an HRP2) or an antigen (i.e., for example, an HRP2 protein). A solid support may include, but is not limited to, a membrane (e.g. a charged membrane), plastic, beads, strips, microtiter wells, microchannels, etc.

II. Detection of Malaria Parasite Biomarkers

A. Detection by Immunoassay

In specific embodiments, the malaria parasite biomarkers of the present invention can be detected and/or measured by immunoassay. Immunoassay requires biospecific capture reagents/binding agent, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

In certain embodiments, the expression levels of the biomarkers employed herein are quantified by immunoassay, such as enzyme-linked immunoassay (ELISA) technology. In specific embodiments, the levels of expression of the biomarkers are determined by contacting the biological sample with antibodies, or antigen binding fragments thereof, that selectively bind to the biomarker; and detecting binding of the antibodies, or antigen binding fragments thereof, to the biomarkers. In certain embodiments, the binding agents employed in the disclosed methods and compositions are labeled with a detectable moiety. In other embodiments, a binding agent and a detection agent are used, in which the detection agent is labeled with a detectable moiety.

For example, the level of a biomarker in a sample can be assayed by contacting the biological sample with an antibody, or antigen binding fragment thereof, that selectively binds to the target biomarker (referred to as a capture molecule or antibody or a binding agent), and detecting the binding of the antibody, or antigen-binding fragment thereof, to the biomarker. The detection can be performed using a second antibody to bind to the capture antibody complexed with its target biomarker. A target biomarker can be an entire protein, or a variant or modified form thereof. Kits for the detection of biomarkers as described herein can include pre-coated strip/plates, biotinylated secondary antibody, standards, controls, buffers, streptavidin-horse radish peroxidise (HRP), tetramethyl benzidine (TMB), stop reagents, and detailed instructions for carrying out the tests including performing standards.

The present disclosure also provides methods for detecting the malaria parasite *Plasmodium* in a subject, wherein the levels of expression of the malaria parasite biomarkers in a biological sample are determined simultaneously. For example, in one embodiment, methods are provided that comprise: (a) contacting a biological sample obtained from the subject with a plurality of binding agents that selectively bind to a plurality of biomarkers disclosed herein for a period of time sufficient to form binding agent-biomarker complexes; and (b) detecting binding of the binding agents to the plurality of biomarkers. The detection of the biomarkers indicates the presence of the malaria parasite in the subject. In further embodiments, detection thereby determines the levels of expression of the biomarkers in the biological sample; and the method can further comprise (c) comparing the levels of expression of the plurality of biomarkers in the biological sample with predetermined threshold values, wherein levels of expression of at least one of the plurality of polypeptide biomarkers above or below the predetermined threshold values indicates, for example, the presence of the malaria parasite in the subject. Examples of binding agents that can be effectively employed in such methods include, but are not limited to, antibodies or antigen-binding fragments thereof, aptamers, lectins and the like.

In a further aspect, the present disclosure provides compositions that can be employed in the disclosed methods. As further described herein, in particular embodiments, the present invention comprises a lateral flow assay. In certain embodiments, a lateral flow device (e.g., a strip) is provided that comprises a binding agent deposited on the device. For example, a strip can be constructed to contain a binding agent (e.g., a biotinylated mAb against PSSP17).

The strip can further be designed to contain streptavidin at the test line. The control line of the strip can comprise IgG. In alternative embodiments, the lateral flow device does not comprise a detection agent; the detection agent (and binding agent) can be added to the sample in a tube prior to being deposited on the lateral flow strip (or prior to placing the lateral flow strip into the sample tube).

In certain embodiments, such compositions comprise a solid substrate and a plurality of binding agents immobilized on the substrate, wherein each of the binding agents is immobilized at a different, indexable, location on the substrate and the binding agents selectively bind to a plurality of biomarkers disclosed herein. In a specific embodiment, the locations are pre-determined. In one embodiment, the binding agents selectively bind to a plurality of biomarkers described herein. Binding agents that can be employed in such compositions include, but are not limited to, antibodies, or antigen-binding fragments thereof, aptamers, lectins and the like.

In a related aspect, methods for assessing malaria in a subject are provided, such methods comprising: (a) contacting a biological sample obtained from the subject with a composition disclosed herein for a period of time sufficient to form binding agent-polypeptide biomarker complexes; and (b) detecting binding of the plurality of binding agents to the plurality of polypeptide biomarkers. In further embodiments, detection thereby determines the levels of expression of the biomarkers in the biological sample; and the method can further comprise (c) comparing the levels of expression of the plurality of polypeptide biomarkers in the biological sample with predetermined threshold values, wherein levels of expression of at least one of the plurality of polypeptide biomarkers above or below the predetermined threshold values indicates malaria status in the subject.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds a biomarker and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

In specific embodiments, the assay performed on the biological sample can comprise contacting the biological sample with one or more capture agents (e.g., antibodies, peptides, aptamer, etc., combinations thereof) to form a biomarker: capture agent complex. The complexes can then be detected and/or quantified. A subject can then be identified as having the malaria parasite based on a comparison of the detected/quantified/measured levels of biomarkers to one or more reference controls as described herein.

In one method, a first, or capture, binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker (or to the bound capture antibody) is then used to detect binding of the polypeptide biomarker to the capture antibody. The detection antibody is preferably conjugated, either directly or indirectly, to a detectable moiety. Examples of detectable moieties that can be employed in such methods include, but are not limited to, cheminescent and luminescent agents; fluorophores such as fluorescein, rhodamine and eosin; radioisotopes; colorimetric agents; and enzyme-substrate labels, such as biotin.

In another embodiment, the assay is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate. Suitable microporous membranes include, for example, those described in US Patent Application Publication no. US 2010/0093557 A1. Methods for the automation of immunoassays are well known in the art and include, for example, those described in U.S. Pat. Nos. 5,885,530, 4,981,785, 6,159,750 and 5,358,691.

The presence of several different polypeptide biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations. For example, a kit can In certain embodiments, such methods employ an array, wherein multiple binding agents (for example capture antibodies) specific for multiple biomarkers are immobilized on a substrate, such as a membrane, with each capture agent being positioned at a specific, pre-determined, location on the substrate. Methods for performing assays employing such arrays include those described, for example, in US Patent Application Publication nos. US2010/0093557A1 and US2010/0190656A1, the disclosures of which are hereby specifically incorporated by reference.

Multiplex arrays in several different formats based on the utilization of, for example, flow cytometry, chemiluminescence or electron-chemiluminesence technology, can be used. Flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis.

In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

B. Detection by Electrochemicaluminescent Assay

In several embodiments, the biomarker biomarkers of the present invention may be detected by means of an electrochemicaluminescent assay developed by Meso Scale Discovery (Gaithersrburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. Nos. 7,497,997; 7,491,540; 7,288,410; 7,036,946; 7,052,861; 6,977,722; 6,919,173; 6,673,533; 6,413,783; 6,362,011; 6,319,670; 6,207,369; 6,140,045; 6,090,545; and 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

C. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. Nos. 6,537,749; 6,329,209; 6,225,047; 5,242,828; PCT International Publication No. WO 00/56934; and PCT International Publication No. WO 03/048768.

In a particular embodiment, the present invention comprises a microarray chip. More specifically, the chip comprises a small wafer that carries a collection of binding agents bound to its surface in an orderly pattern, each binding agent occupying a specific position on the chip. The set of binding agents specifically bind to each of the one or more one or more of the biomarkers described herein. In particular embodiments, a few micro-liters of blood serum or plasma are dropped on the chip array. Biomarker proteins present in the tested specimen bind to the binding agents specifically recognized by them. Subtype and amount of bound mark is detected and quantified using, for example, a fluorescently-labeled secondary, subtype-specific antibody. In particular embodiments, an optical reader is used for bound biomarker detection and quantification. Thus, a system can comprise a chip array and an optical reader. In other embodiments, a chip is provided.

III. Kits for the Detection of Biomarkers

In another aspect, the present invention provides kits for qualifying malaria status, which kits are used to detect the biomarkers described herein. In a specific embodiment, the kit is provided as a lateral flow immunoassay kit comprising antibodies to the biomarkers of the present invention including, but not limited to, PSSP17.

The kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of the sample.

In certain embodiments, a patient can be diagnosed by adding a biological sample (e.g., saliva) from the patient to the kit and detecting the relevant biomarkers conjugated with antibodies, specifically, by a method which comprises the steps of: (i) collecting saliva from the patient; (ii) adding the saliva from patient to a diagnostic kit; and, (iii) detecting the biomarkers conjugated with antibodies. In this method, the antibodies are brought into contact with the patient's saliva. If the biomarkers are present in the sample, the antibodies will bind to the sample, or a portion thereof. In other kit and diagnostic embodiments, saliva not be collected from the patient (i.e., it is already collected). Saliva samples can be collected from subject of varying ages. Moreover, in other embodiments, the sample may comprise a blood, serum, sweat, tissue, urine or a clinical sample.

The kit can also comprise a washing solution or instructions for making a washing solution, in which the combination of the capture reagents and the washing solution allows capture of the biomarkers on the solid support for subsequent detection by, e.g., antibodies or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration or normalization. Detection of the markers described herein may be accomplished using a lateral flow assay.

In certain embodiments, the malaria parasite biomarker proteins of the present invention can be detected and/or measured by immunoassay. Immunoassay requires biospecific capture reagents, such as antibodies to capture the biomarkers. Many antibodies are available commercially. Antibodies also can be produced by methods well known in the art, e.g., by immunizing animals with the malaria parasite biomarker proteins. Proteins can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or luminescence/fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds a malaria parasite biomarker proteins and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

In specific embodiments, the assay performed on the biological sample (e.g., saliva) can comprise contacting the biological sample with one or more capture agents (e.g., antibodies, peptides, aptamer, etc., combinations thereof) to form a biomarker: capture agent complex. The complexes can then be detected and/or quantified. In certain embodiments, a subject can then be identified as being asymptomatic or symptomatic for malaria based on the presence of the malaria parasite biomarker proteins in the sample or a comparison of the detected/quantified/measured levels of malaria parasite biomarker proteins to one or more reference controls as described herein.

In particular embodiments, the malaria parasite biomarker proteins of the present invention can be captured and concentrated using nano particles. In a specific embodiment, the proteins can be captured and concentrated using Nanotrap® technology (Ceres Nanosciences, Inc. (Manassas, Va.)). Briefly, the Nanotrap platform reduces pre-analytical variability by enabling biomarker enrichment, removal of high-abundance analytes, and by preventing degradation to highly labile analytes in an innovative, one-step collection workflow. Multiple analytes sequestered from a single sample can be concentrated and eluted into small volumes to effectively amplify, up to 100-fold or greater depending on the starting sample volume (Shafagati, 2014; Shafagati, 2013; Longo, et al., 2009), resulting in substantial improvements to downstream analytical sensitivity.

In another aspect, the present invention provides kits for rapidly diagnosing malaria in asymptomatic and/or symptomatic individuals. In particular embodiments, the kit is provided as a 61 par point of care use malaria RDT. The kit can comprise antibodies (or fragments that specifically bind) to the proteins described herein. In a specific embodiment, the antibodies specifically bind to a protein biomarker, which biomarkers include one or more of PF3D7_0111300 (replication factor c protein, putative), PF3D7_0216700.1 (conserved *Plasmodium* protein, unknown function), PF3D7_0310500 (DEAD box helicase, putative), PF3D7_0318200 (DNA-directed RNA polymerase II, putative), PF3D7_0401900 (acyl-CoA synthetase (ACS6)), PF3D7_0419900 (phosphatidylinositol 4-kinase, putative), PF3D7_0422300 (alpha tubulin 2), PF3D7_0507800 (conserved *Plasmodium* protein, unknown function), PF3D7_0508100 (SET domain protein, putative (SETS)), PF3D7_0509400 (RNA polymerase I (RNAPI)), PF3D7_0510100 (conserved *Plasmodium* protein, unknown function), PF3D7_0511500 (RNA pseudouridylate synthase, putative), PF3D7_0512600 (Rab GTPase 1b (Rab1b)), PF3D7_0528700 (peptidyl-prolyl cis-trans isomerase (CYP23)), PF3D7_0529800 (conserved *Plasmodium* protein, unknown function), PF3D7_0610400 (histone H3 (H3)), PF3D7_0632500 (erythrocyte membrane protein 1, PfEMP1 (VAR)), PF3D7_0704100 (conserved *Plasmodium* membrane protein, unknown function), PF3D7_0705500 (inositol-phosphate phosphatase, putative), PF3D7_0717900 (thioredoxin-like protein), PF3D7_0720700 (phosphoinositide-binding protein, putative), PF3D7_0818900 (heat shock protein 70 (HSP70)), PF3D7_0831700 (heat shock protein 70 (HSP70-x)), PF3D7_0903200 (Rab GTPase 7 (Rab7)), PF3D7_0904100 (adapter-related protein, putative), PF3D7_0906100 (developmental protein, putative), PF3D7_0907200 (GTPase activator, putative), PF3D7_0917900 (heat shock protein 70 (HSP70-2)), PF3D7_0927200 (zinc finger protein, putative), PF3D7_1015900 (enolase (ENO)), PF3D7_1029000 (conserved *Plasmodium* protein, unknown function, pseudogene), PF3D7_1034400 (flavoprotein subunit of succinate dehydrogenase (SDHA)), PF3D7_1102400 (flavoprotein, putative), PF3D7_1105600 (translocon component PTEX88 (PTEX88)), PF3D7_1134700 (DNA-directed RNA polymerase 1, subunit 2, putative), PF3D7_1142100 (conserved *Plasmodium* protein, unknown function), PF3D7_1200200 (rifin (RIF)), PF3D7_1202300 (dynein heavy chain, putative), PF3D7_1207000 (conserved *Plasmodium* protein, unknown function), PF3D7_1211800 (polyubiquitin (Pf-pUB)), PF3D7_1215100 (conserved *Plasmodium* protein, unknown function), PF3D7_1216000 (serine—tRNA ligase, putative), PF3D7_1216900 (DNA-binding chaperone, putative), PF3D7_1218800 (secreted ookinete protein, putative (PSSP17)), PF3D7_1231100 (Rab GTPase 2 (RAB2)), PF3D7_1235700 (ATP synthase subunit beta, mitochondrial), PF3D7_1239900 (vesicle fusion and protein sorting subunit 16, putative (VPS16)), PF3D7_1313500 (conserved *Plasmodium* membrane protein, unknown function), PF3D7_1318300 (conserved *Plasmodium* protein, unknown function), PF3D7_1319200 (conserved *Plasmodium* protein, unknown function), PF3D7_1325900 (conserved *Plasmodium* protein, unknown function), PF3D7_1327300 (conserved *Plasmodium* protein, unknown function), PF3D7_1337200 (1-deoxy-D-xylulose 5-phosphate synthase), PF3D7_1337500 (conserved *Plasmodium* protein, unknown function), PF3D7_1342600 (myosin A (MyoA)), PF3D7_1353000 (tryptophan-rich antigen, pseudogene), PF3D7_1411400 (plastid replication-repair enzyme (PREX)), PF3D7_1421300 (conserved *Plasmodium* protein, unknown function), PF3D7_1434200 (calmodulin (CAM)), PF3D7_1443800 (zinc finger protein, putative), and PF3D7_1452200 (aminomethyltransferase, putative).

In other embodiments, the methods, compositions and kits of the present invention can comprise monoclonal antibodies, cGMP conjugated monoclonal antibodies, cGMP recombinant proteins, cGMP saliva collection vessels and stabilization buffers.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Sex-Partitioning of the *Plasmodium falciparum* Stage V Gametocyte Proteome Provides Insight into *Falciparum*-Specific Cell Biology Sexual stages represent only a small fraction of *Plasmodium falciparum* parasites that are present during human malaria infection, yet they alone are responsible for disease transmission. As such, the Malaria Eradication Research Agenda (malERA) has prioritized the need for studies specifically addressing these transmission stages, with the hope of developing new transmission-blocking vaccines and drugs, as well as diagnostics that are specific for these sexual stages. In fact, one of the critical gaps in malaria transmission biology and surveillance centers on the lack of knowledge about the infectivity of symptomatic and asymptomatic gametocytemic individuals for mosquitoes. Many infected individuals harboring the *Plasmodium falciparum* sexual stage, or gametocyte, are asymptomatic carriers and they represent the primary reservoir for malaria transmission. Missing the opportunity to treat these carriers will increase the risk for epidemic malaria in regions that have approached the elimination phase. Thus, proper surveillance of gametocyte carriers is critical for evaluating ongoing malaria control and elimination programs. Surveillance is difficult, however, because gametocytes comprise only 0.1-2% of the total body parasite load during active infection, and are only observed in the bloodstream in their mature (Stage V) form, with the first four developing stages sequestered in tissues. Microscopy-based analysis for sex ratio determination and infectivity studies remains limited due to cost, training and suitability for population-wide studies. Although light microscopy remains the gold standard for malaria diagnosis, the relatively low prevalence of circulating gametocytes makes it difficult to, accurately detect much less quantify these stages. Moreover, due to variations in skill level of microscopists and inconsistency in method, exclusive use of light microscopy estimates of gametocyte carriage carries a high risk of error. Importantly, the presence of stage V gametocytes in the bloodstream alone, as determined by thick smear microscopy does not imply infectivity to mosquitoes. Ratios of male and female gametocytes in the blood circulation are generally skewed towards the female, but they can vary significantly based on co-infection, parasite and gametocyte density and host environmental factors and it is therefore hypothesized that this variation in sex ratios will influence mosquito infectivity. For example, mature gametocyte sex ratios can change during the course of infection in response to host cues or especially following antimalarial treatment resulting in an increase in the number of males. However, it remains unknown whether the transmission potential to mosquitoes of the individuals in these studies fluctuated due to the changes in sex ratio.

There are currently no molecular tools to distinguish male and female mature *P. falciparum* gametocytes (of which at least one of each is required for fertilization and ookinete development in the mosquito), and there is no correlate available to predict gametocyte infectiousness to mosquitoes. Although the proteome of *Plasmodium* gametocytes has been described, these previous analyses fell just short of providing the partitioned male and female proteomes for *P. falciparum*. Moreover, the availability of the genomes of human, primate and rodent malaria parasites and the acquisition of sequence information for recently derived field isolates of *P. falciparum* have created the opportunity to understand gene diversity and conservation in sexual stage development across Plasmodia. Identifying markers that differ between male and female *P. falciparum* stage V gametocytes is critical in informing transgenic approaches aimed at separating the two. It has been argued that the inherent evolutionary differences between rodent and human malaria parasites, especially for the sexual stages, limit the utility of the *P. berghei* gametocyte proteome in providing a priori knowledge of these markers. Several iterations and improvements to the *P. berghei* genome have been made available since 2005, while MS search engines have commensurately improved further compounding the issue. However, we would also argue that the current evidence suggests a high degree of conservation in gametocyte gene complement across *Plasmodium*, and therefore presumably in sex-specific genes-despite key differences such as gametocyte sequestration and morphology. Here, we report on our effort to partially address these scientific gaps and to test our gametocyte gene conservation hypothesis through the use of leading-edge comparative protein bioinformatics analyses of the mature stage V gametocyte proteomes of two distinct *P. falciparum* strains with our updated *P. berghei* male and female gametocyte proteomes.

Materials and Methods

Parasite Culture and Gametocyte Isolation:
*P. falciparum* NF54 Gametocyte Culture.
*P. falciparum* gametocytes were cultured in RPMI-1640 containing HEPES and glutamine and supplemented with 10% human serum and hypoxanthine as described earlier (34). *P. falciparum* NF54 strain was diluted to 0.5% mixed stage asexual parasites and 4% hematocrit in complete culture medium in six well plates. Plates were transferred to 37° C. incubator and microaerophilic environment was created using desiccators as candle jar. Media was exchanged every day without the addition of new blood from day 1 to day 17 (culture maturation). To remove asexual stage parasites 50 mM N-acetylglucosamine was added to the culture media from day 8 (early stage gametocytes) until day 10. Blood smears were made every alternate day to monitor the progress of the culture and to determine gametocyte percent on day 18. Stage V gametocytes (stage V) were harvested from culture at day 17 post-gametocytogenesis initiation and isolated by passage through a LS-25 Midi MACS column (CS Miltenyi).
*P. falciparum* Dd2 Gametocyte Culture.
The production of stage V gametocytes was performed using a modified version of a previously described protocol (35). Ten (10) mL cultures at 4% hematocrit and ~5% ring parasitemia were sorbitol synchronized. After 24 hours, trophozoite cultures were transferred to a T75 flask to which complete media and red blood cells were added to create a 30 mL culture with 2% hematocrit in each flask. After another 24 hrs, adding 50% old media and 50% new complete media stressed the newly reinvaded rings. Cultures were allowed to develop to late schizonts and then split into three T75 flasks evenly. Twenty (20) mLs of fresh media was then added to each flask. During sexual stage development, fresh media was added daily. At 48 hours after sexual stage invasion, 1 mL of 1M N-Acetyl-D-Glucosamine was added to all flasks in order to clear asexual parasites. Drug treatment was given during media changes for three consecutive days. On day nine of sexual development, the cultures were MACS column separated to purify late stage gametocytes. Purified cultures were washed in PBS and snap frozen.

Protein Extraction.

The GiRBC elution from MACS column was washed with cold PBS three times prior to protein extraction. Freezing and thaw method was applied to extracted the soluble proteins by adding 120 μL 5 mM phosphate buffer containing 0.5 mM PMSF, 1 mM EDTA and 1 mM protease inhibitors cocktail (Sigma, St. Louis, Mo.) to $1\times10^6$ GiRBC pellets. Totally four cycles of freezing and thaw cycles were used. The supernatant was collected as soluble protein fraction after centrifugation at 20,000 g for 30 min at 4° C. To get the membrane part proteins, the pellets was washed by cold PBS for 3 times prior to be dissolved in 95 μL SDT-lysis buffer including 4% (w/v) SDS, 100 mM Tris/HCl, 0.1 M DTT, pH 7.6, then boiled at 95° C. for 5 min. The supernatant was collected as membrane part protein fraction after centrifugation at 20,000 g for 5 min at 4° C.

Multi-Lane Combined in-Gel Digestion (MLCID).

We used a Multi-Lane Combined In-gel Digestion (ML-CID) strategy to reduce the impact of non-specific absorption during the process of in-gel tryptic digestion and to avoid losing the SDS-PAGE separation power. For NF54 parasites, we used 3 lanes for the soluble protein fraction and 4 lanes for the membrane fraction, respectively, and each lane was loaded with 20 μL of sample under reducing conditions. After resolving on a 4-20% precast gradient gel (BioRad, Hercules, Calif.), the proteins were stained with Coomassie. GiRBC soluble and membrane fractions were cut into 14 slices by combining 3 lanes (soluble) and 16 slices by combining 4 lanes (membrane). Both the soluble and membrane fractions from Dd2 were cut into 14 slices by combing 3 lanes. Gel slices were cut into 1 xl mm pieces prior to de-staining, reduction and alkylation, tryptic digestion and peptide extraction. The extracted peptides were lyophilized and then were re-suspended in 2% ACN, 97.9% water and 0.1% formic acid buffer for LC-MS/MS analysis.

LC-MS/MS.

Biological in-gel digestion replicates were analyzed independently as follows. One third of the MLCID sample of all the fractions, were injected onto an Agilent LC-MS system comprised of a 1200 LC system coupled to a 6520 Q-TOF via an HPLC Chip Cube interface. The only exception to this process was made for the first low molecular weight fraction, which consisted primarily of hemoglobin, and thus only ⅕₀th of this fraction was injected. The sample was trapped and analyzed using an Agilent Polaris-HR-Chip-3C18 chip (360 nL, 180 Å C18 trap with a 75 μm i.d., 150 mm length, 180 Å C18 analytical column). Peptides were loaded onto the enrichment column automatically by autosampler using 97% solvent A (0.1% formic acid in water) and 3% solvent B (0.1% formic acid in 90% acetonitrile) at a flow rate of 2 μL/min. Elution of peptides from the analytical column was performed using a gradient starting at 97% A at 300 nL/min. The mobile phase was 3-10% B for 4 min, 10-35% B for 56 min, 35-99% for 2 min, and maintained at 99% B for 6 min, followed by re-equilibration of the column with 3% B for 10 min. Data dependent (autoMS2) mode was used for MS acquisition by Agilent 6520 Q-TOF in 2 GHz. Precursor MS spectra were acquired from m/z 315 to 1700 and the top 4 peaks were selected for MS/MS analysis. Product scans were acquired from m/z 50 to 1700 at a scan rate of 1.5/second. A medium isolation width (~4 amu) was used, and a collision energy of slope 3.9 V/100 Da with a 2.9 V offset was applied for fragmentation. A dynamic exclusion list was applied, with precursors excluded of 0.50 min after two MS/MS spectrum was acquired.

Mass Spectrometry Data Search and Analysis.

Each sample was further fractionated into 14 membrane and 14 soluble fractions. Raw data from Dd2 sample runs (2 biological replicates, 217,165 MS/MS total spectra) and NF54 GiRBC sample runs (3 biological replicates, 497,006 MS/MS total spectra) was converted to mzXML format using Trapper (Institute for Systems Biology, Seattle, Wash.). A merged search was performed on the mzXML data for each fraction using the PepArML metasearch engine (36), which automatically conducts target and decoy searches using the following: Mascot (37), OMSSA (38) and Tandem (39) with native, K-score (40) and S-score pluggable scoring modules (41), and Inspect (42) with MS-GF spectral probability scoring (43). The results were then combined using an unsupervised machine-learning strategy, and the peptide identification false discovery rates were estimated using identifications from the reversed decoy searches (44).

The data was searched by a combined database of SwissProt Human and *Plasmodium falciparum* sequences from GeneDB (2013.02), which consists of 28,960 entries with the following parameters; fixed modification: carbamidomethyl cysteine and variable modification: oxidized methionine; mass tolerance: 30 ppm and 20 ppm respectively for precursor and fragment ions; one missed cleavage. The results from the metasearch were combined and the results were parsed into the MASPECTRAS 2 data analysis system (18) with data filters of 1% spectra FDR and 5% peptide FDR, and protein identifications were then clustered to remove redundancy. Proteins were clustered together if there was a peptide identification shared between them, since this indicates substantial sequence similarity, and the protein with the greatest number of peptides identified was considered the unique protein identification from that group. Throughout this paper we report only the unique identifications. Proteins identified by single peptides were manually validated. The data analysis pipeline meets all MIAPE standards (45) and the proteomics data have been deposited in the ProteomeExchange via the PRotein IDEntifications database (PRIDE) partner repository with the dataset identifier PXD000813 (46). The protein lists have also been uploaded to PlasmoDB (plasmodb.org).

For the reanalysis of the Khan, et al. dataset (11), the individual MS raw files from Male (113,213 total MS/MS spectra) and Female dataset (243,468 total MS/MS spectra) were searched against a combined database of SwissProt Human, Mouse and *P. berghei*. Using these results we determined the male/female partitioned proteomes for *P. falciparum* gametocytes through a subtractive bioinformatics proteomics approach. Briefly, in our approach, we take protein identification lists and use set comparisons to generate protein lists that are specific for biological states, with those protein lists clustered to remove redundancy. Therefore, we took the NF54 and Dd2 gametocyte-infected red blood cell lysate proteome and subtracted out all host proteins, generating the NF54 and Dd2 gametocyte proteomes. Putative male-specific, female-specific, and sex-unspecific proteomes were generated by taking protein identifications unique to NF54 and Dd2, respectively. These putative proteomes were then BLAST searched against the two previous datasets of Khan et al. and Silvestrini et al. (8, 11). In house developed Python scripts were used for BLAST automation, with an e-value cutoff of 0.01 and >40% identity for BLAST 2.2.20 homology search. In order to focus on the parasite proteome, all identified human proteins were excluded from this analysis.

Identified proteins were annotated by GeneDB (02, 2013); specifically, the Gene Ontology database was searched by BLAST homology for annotations. The surface expressed (SE) proteins were predicted by searching for canonical signal peptides with the SignalP 4.1 Server (47). Transmembrane domain information was obtained on all identified proteins by the transmembrane protein prediction tool TMHMM Server v. 2.0 (48).

Analysis of Diversity and Divergence for Male and Female *P. falciparum* Gametocyte Proteins.

The 7EN SNP diversity statistic, representing mean pairwise non-synonymous SNP diversity per site, was calculated for previously generated data within each genic region for a given population using the VCFtools—site-pi utility (49). For each pair of populations, the Fst divergence statistic was calculated for each gene with the VCFtools implementation of Fst and weighted Fst estimators as described in Weir and Cockerham (50).

Expression of Recombinant Proteins and Generation of Polyclonal Antibodies for proteomic validation.

The selection of predicted immunogenic domains for each protein were based on physiochemical properties of each gene (PF3D7_0906100; PF3D7_1218800; PF3D7_0309100; PF3D7_0422000) using the Bcepred server (51) and Immune epitope Database (IEDP) (52). Each codon-optimized gene or gene fragment (GenScript) was used as a template for PCR along with the following primer sets (all 5' to 3'): PF3D7_0906100, F-CAC-CATGGGTAACAAAATTAGC (SEQ ID NO:1), R-TTTCAGGTTTTTGATACGTTCC (SEQ ID NO:2); PF3D7_1218800, F-CACCAAAATCGTGCTGTCCA (SEQ ID NO:3), R-ACCGAAGTAAATAAAACTCGGTTC (SEQ ID NO:4); PF3D7_0309100, F-CACCGACCT-GAGCGGCCT (SEQ ID NO:5), R-CAGTTCTTCGTTTTT-GATGAACACG (SEQ ID NO:6). Each 20 µl PCR reaction consisted of 0.25 µl of DNA (200 ng/µl), 4.0 µl of 5× iProof DNA polymerase buffer, 0.4 µl of dNTPs (10 mM each), 0.4 µl each of forward and reverse primers (10 µM), 0.1 µl of iProof DNA polymerase (2 U/µl), and 14.85 µl of sterile deionized water. Reaction conditions were 98° C. for 2 minutes, followed by 40 cycles of 98° C. for 15 seconds, 62° C. for 25 seconds, and 72° C. for 25 seconds. All forward primers were appended with the nucleotides CACC on the 5' end to facilitate directional insertion of each amplicon into the *E. coli* expression vector pBAD202/D-TOPO. Ligation and transformation steps were carried out according to the manufacturer's protocols, and clones were grown on selective LB agar plates with kanamycin (50 µg/ml) overnight at 37° C. For each gene, colonies were picked and screened by PCR and then sequenced to confirm proper orientation and reading frame. Prior to induction, positive clones were grown in LB media+kanamycin (50 µg/ml) overnight at 37° C. in a shaking incubator (200 RPM). Each overnight culture was then used to seed 50 mL of fresh LB+kanamycin (50 µg/mL), grown to an O.D.600≈0.4, and then induced with arabinose (0.01%) for 6-8 hours at 37° C. Cells were harvested by centrifugation at 10,000×g for 10 minutes, and the presence of recombinant protein from each expression was confirmed by western blot using mouse anti-His monoclonal Ab (Sigma). The cell pellets were then processed for recombinant protein using BugBuster Reagent (Novagen) following the manufacturer's protocol for both soluble and insoluble fractions. Recombinant protein was then purified by immobilized metal affinity chromatography (ProBond, Invitrogen) following the manufacturer's "hybrid" protocol for inclusion bodies and the "native" protocol for soluble protein. Following elution from the column, eluates positive for protein by Western blot were pooled and dialyzed overnight (3,500-10,000 Da MWCO) against imadozole-free elution buffer and then concentrated using diafiltration (3,000 Da MWCO).

To generate polyclonal antibodies, Swiss Webster mice were immunized with purified recombinant protein emulsified with incomplete Freund's adjuvant (Sigma) following a prime and 3 boosts at two week intervals. The mice were exsanguinated at the end of the immunization regimen to collect serum.

Immunofluorescence Microscopy Assays.

*P. falciparum* NF54 gametocyte and trophozoite samples were fixed with 4% paraformaldehyde/0.0075% glutaraldehyde and prepared for fluorescence microscopy by washing three times with PBS. The cells were permeabilized with 0.2% Triton-X 100/PBS for 10 minutes and then washed as before. After washing, samples were blocked with 3% BSA in PBS overnight at 4° C. The samples were then incubated with mouse anti-gametocyte protein serum (1:50) for 1 hr at RT. Cells were washed with PBS as before and detected with Alexa Fluor® 488 Goat Anti-Mouse IgG (H+L), highly cross-adsorbed (Molecular Probes®, 1:1000) in 0.02% Evans blue for 1 hr at RT. Following incubation, the cells were washed three times with PBS, resuspended in PBS, spotted on slides and allowed to air dry. Samples were mounted using Slow Fade Gold antifade reagent with DAPI (Molecular Probes) or Aqua Poly/mount (Polysciences Inc.). Samples were imaged using a Nikon Upright E800 microscope equipped with SPOT camera and software and a Nikon 90i light microscope (Nikon Corp., Tokyo, Japan) connected to a Hamamatsu ORCA high sensitivity monochrome CCD camera.

Results

The *Plasmodium falciparum* Stage V Gametocyte Proteome: NF54 vs. Dd2.

We selected two *P. falciparum* strains for proteomic analysis of stage V gametocytes: a transmission-competent reference isolate, NF54 (West Africa) (14) and a Southeast Asian clone Dd2 (15). Importantly, Dd2 has a defect in male gametocyte development resulting in arrested and morphologically altered male stages. The genetic basis of this defect is at least in part, a mutation in the male development 1 (MDV-1) gene (16). Assuming that the stage V proteome of Dd2 will be enriched for female proteins, we can then characterize the male- and female-specific *P. falciparum* proteomes by comparative analysis of Dd2 and NF54.

We produced three biological replicates of *P. falciparum* (NF54 isolate) stage V gametocytes in the presence of GlcNAc to reduce the number of asexuals that could remain present at 17 days post-initiation of gametocytogenesis. Microscopic analysis of thin-blood smears from the day 17 culture suggested a predominantly stage V culture (~6-7% gametocytemia), with few stage IV gametocytes and a sex ratio of approximately 1:4 for male vs. female (FIG. 1A, Table 1). In parallel, we cultured the *P. falciparum* Dd2 mutant clone and induced gametocytogenesis in the presence of GlcNAc to produce two biological replicates of preferentially female-enriched stage V gametocyte samples. We determined by microscopy the number of pre-stage V gametocytes in two replicate cultures with low and high gametocytemias to be 14.5% and 27.3%, respectively (Table 2). The proportion of morphologically altered tear-drop forms were 0.6% and 1.2% and rectangular forms were 0.4% and 1.6% for each of the two replicates. Although far fewer in number we considered these latter forms to be likely male gametocyte stages 1-4 and thus, a potential source of contaminating male proteins.

TABLE 1

Microscopic verification of the Stage V gametocyte male-to-female ratio for the *Plasmodium falciparum* NF54 used in this study. Several thin-smear slides taken from a N-acetylglucosamine (GlcNAc) treated culture of NF54 was examined by oil-immersion microscopy (1000X) at day 17 post-initiation of gametocytogenesis by 1/40 dilution of Giemsa in Sorensen's buffer.

|  | Read 1 | Read 2 | Read 3 | Pooled |
|---|---|---|---|---|
| Total # RBCs counted | 1204 | 1212 | 1130 | 3546 |
| Number of Males (pink) | 16 | 15 | 17 | 48 |
| Number of Females (blue) | 88 | 58 | 40 | 186 |
| Total # Gametocytes (Stage V) | 104 | 73 | 57 | 234 |
| Gametocytemia (Stage V) | 0.09 | 0.06 | 0.05 | 0.07 |
| Male:Female Ratio | 0.18 | 0.26 | 0.43 | 0.26 |

TABLE 2

Microscopic verification of purified Pre- and Mature Stage V gametocytes for the *Plasmodium falciparum* Dd2 line used in this study.

|  | Gametocytemia (%) | Pre-Stage V (%) | Tear drop (%) | Rectangular (%) |
|---|---|---|---|---|
| LOW | 503/758 (66.3) | 73/503 (14.5) | 3/503 (0.60) | 2/503 (0.40) |
| HIGH | 506/536 (94.4) | 138/506 (27.3) | 6/506 (1.19) | 8/506 (1.58) |

The Dd2 clone has a defect in male gametocyte development. However, the presence of Pre-Stage V gametocytes would complicate the partitioning of Dd2 proteins since male-specific markers in *P. falciparum*, e.g., alpha-tubulin II are expressed in pre-stage V females. In addition to determining the number of Pre-Stage V's we also ascertained the number of "tear drop" and "rectangular" forms, which have been hypothesized to be malformed male gametocytes. The contamination level with Pre-Stage V as well as these malformed parasites helped explain our Dd2 gametocyte proteome.

Figures 2A, 2B, 2C, 2D, 2E, 2F, 2G, 2H:
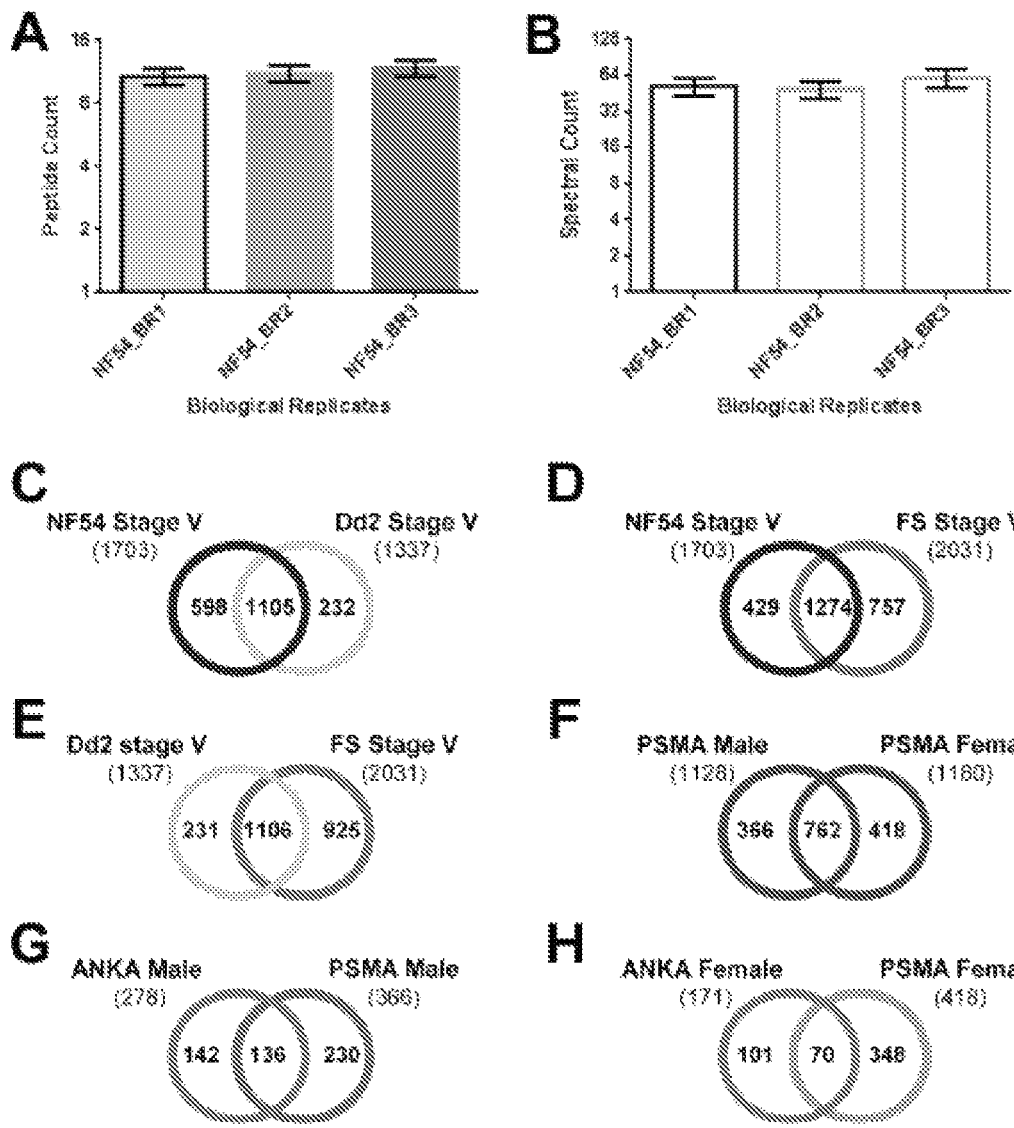
FIG. 2A-2H. Summary of protein identifications from the reanalysis of *Plasmodium berghei* ANKA 2.34 Male and Female Gametocyte Proteomes and the current Stage V *Plasmodium falciparum* gametocyte proteomes for the NF54 isolate and Dd2 strain. Reproducibility of the analyses of the *P. falciparum* NF54 samples is shown. Three biological replicates for *P. falciparum* NF54 preparations were analyzed by MS. The 1090 proteins identified from analysis of all replicates were considered for statistical analysis. (A) Peptides per identified protein for each biological replicate (B) and spectra per identified protein for each biological replicate. Normalized peptide count and spectral count were analyzed by one-way ANOVA with Geisser-Greenhouse correction method. Average values are plotted with error bars of 95% CI. (C). Male and Female *P. berghei* protein identification following the re-analysis of the published dataset. Out of 1546 total unique protein identification 762 proteins were in common between *P. berghei* male and *P. berghei* female at 1% spectra FDR (minimum one unique peptide for a protein, see methods for single peptide validation details) and 5% peptide FDR for a protein. We found that 366 proteins were specific for male *P. berghei* and 418 proteins were *P. berghei* female specific. (D). *P. falciparum* NF54 and Dd2 protein identification. There were 1105 proteins in common between 1703 Pf NF54 and 1337 Pf Dd2 total protein identification at 1% spectra FDR (minimum one unique peptide for a protein, see methods for single peptide validation details) and 5% peptide FDR for a protein. We observed that 598 proteins were NF54-specific and 232 proteins were Dd2-specific. (E)-(F). Proteins in common between NF54, Dd2 and FSgv data. 74% Pf. NF54 proteins were present in the Silvestrini gametocyte stage V and 82% of the Pf. Dd2 proteins were stage V proteins in accordance with the Silvestrini stage V data.

We demonstrated highly consistent acquisition of the mixed-sex stage V gametocyte proteome (FIG. 2A), with greater than 95% reproducibility in protein identifications across biological replicates (FIG. 2A-B). We identified 1,703 mature NF54 stage V proteins, including all the known and well-studied gametocyte surface markers such as P230, P48/45, P47 and the LCCL domain-containing (CCp) protein family of molecules (Table 1). Of these, 449 (26%) proteins were consistently and exclusively identified in the membrane fraction of each sample. In parallel, a total of 1,337 proteins were reproducibly identified from the two Dd2 biological replicates (Table 2). Of these, 726 (54%) proteins were consistently and exclusively identified in the membrane fraction of each sample. For both NF54 and Dd2 it remains unclear if these proteins localize to the parasite plasmalemma or RBC membrane. We observed that NF54 and Dd2 have 1105 proteins in common, 598 NF54-specific proteins and 232 Dd2-specific proteins, which may include proteins emanating from the malformed, arrested male gametocytes (Table 2). We compared our NF54 gametocyte stage V proteome (1703 proteins), which will be referred to in the text as $DTg^V$, with the recently described *P. falciparum* 3D7/NF54 gametocyte stage V proteomes, gametocyte stage I-II and trophozoite protein lists (8), the datasets of which we refer to in our study here on as $FSg^V$ (2,031 proteins), $FSg^{I-II}$ (1,427 proteins) and FS Asx (1,345 proteins), respectively. For these three datasets, we converted the previous and now deprecated accession numbers for each protein to the new protein identifiers as described in the *P. falciparum* 3D7 databases in GeneDB (Version 3) and PlasmoDB (Version 9.3.11 Mar. 11, 2013). The NF54 stage V proteome was comparable to the previously described 3D7/NF54 gametocyte stage V proteome (8), with 1,274 proteins found to be in common between the two NF54 datasets. We also noted the addition of 429 newly identified NF54 proteins to the gametocyte proteome (FIG. 2D). Together, these two datasets represent the most complete *P. falciparum* NF54 stage V gametocyte proteome to date. The Dd2 stage V proteome was also comparable to the $FSg^V$ proteome, with 1106 proteins in common (FIG. 2E). Similar to the results with our NF54 stage V comparison, we noted that ~230 Dd2-specific proteins had partitioned from FSgv. The acquisition of the NF54 and Dd2 stage V gametocyte proteomes (summary MS statistics are provided in Table 3) represents the first step in our Systematic Subtractive Protein Bioinformatics analysis (SSB) approach, which is outlined in FIG. 1C.

TABLE 3

Mass spectrometry data summary statistics for *P. falciparum* NF54 and Dd2 stage V gametocytes.

| Strain | Total # Spectra | # Unique Spectra | Unique Proteins Identified |
|---|---|---|---|
| *P. falciparum* NF54 | | | |
| Membrane Fraction | 97,128 | 96,167 | 1455 |
| Soluble Fraction | 87,308 | 86,390 | 1031 |
| Total NF54 | 184,436 | 182,557 | 1703* |
| *P. falciparum* Dd2 | | | |
| Membrane Fraction | 80,127 | 36,064 | 1065 |
| Soluble Fraction | 77,364 | 49,184 | 893 |
| Total Dd2 | 157,491 | 85,248 | 1337* |
| Combined Total | 341,927 | 267,805 | 1935** |

*783 proteins are shared between membrane and soluble NF54 proteins and
*621 proteins are shared between Dd2 membrane and soluble proteins.
**1105 proteins are shared between Dd2 and NF54 proteins.

Re-Analysis of the Rodent Malaria Sex-Specific Proteomes.

To define and characterize the subset of conserved male and female *Plasmodium* gametocyte markers, we sought to compare the Dd2 and NF54 data with the available male and female proteomes from the rodent malaria parasite, *P. berghei* ANKA 2.34 (11) (see FIG. 1C for the strategy). However, given the number of iterations of the *P. berghei* genome since 2005, as well as further refinement of MS search engines capabilities, we first performed a PepArML-Search MASPECTRAS2 Analysis (PSMA) of the original peptide spectral data from that study, to allow for appropriate and updated comparisons of protein identities (17, 18).

Our re-analysis resulted in updated *P. berghei* male (1,128 clustered proteins) and female (1,180 clustered proteins) gametocyte proteomes (Table 4). From these two datasets we identified 762 clustered proteins (FIG. 2F) that were common between male and female gametocytes, as compared to the 51 shared proteins originally reported between berghei males and females (11). The re-analyzed (PSMA) sex-specific protein lists increased from 278 to 366 male proteins (FIG. 2G) and 171 to 418 female proteins (FIG. 2H). We found that only 136 proteins were conserved between the original and current Male-specific protein lists (Table 2F) and 70 proteins between the original and current Female-specific protein lists (Table 2G). Taken altogether, the combined datasets represent the most complete ANKA sex-specific gametocyte proteomes to date. Apart from the increased resolution of the data set through the use of the PSMA approach, we also noted that seven proteins originally described to be male specific (11), actually partitioned to the female specific protein list and that two proteins originally reported to be female specific were now found to be in the male specific list (Table 5). We also observed that several proteins were putatively shared between males and females in the current PSMA analyses with differential enrichments in one sex over the other (FIG. 10).

TABLE 4

Comparative mass spectrometry data summary statistics. Summary of the re-analyses of the *Plasmodium berghei* ANKA 2.34 Male and Female Gametocyte Proteomes using an updated *P. berghei* genome database (version 2013-01) and the PepArML Search-MASPECTRAS2 Analysis (PSMA) platform.

|  | Total # Spectra | # Unique Peptide | Unique Proteins Identified |
|---|---|---|---|
| *P. berghei* MALE | | | |
| Previous [a] | — | — | 650 |
| Current [b] | 30,786 | 9,389 | 1,128 |
| *P. berghei* FEMALE | | | |
| Previous | — | — | 541 |
| Current | 41,719 | 9,465 | 1,180 |
| MALE Specific | | | |
| Previous | — | 698 | 278 |
| Current | 5,076 | 2,158 | 366 |
| FEMALE specific | | | |
| Previous | — | 216 | 171 |
| Current | 3,405 | 1,359 | 418 |
| Shared Male/Female | | | |
| Previous | — | 758 | 69 |
| Current | 64,024 | 10,407 | 762 |

[a] Search engine used in previous analyses: Mascot (11).
[b] Search engine used in current analyses: Mascot, OMSSA, X!Tandem, Kscore, Sscore, Inspect and MyriMatch.

TABLE 5

A PSMA reanalysis of the existing *Plasmodium berghei* male and female gametocyte proteome using the current iteration of the genome revealed significant changes in the assignment of male and female proteins.

| | | Previous [α] | | Current [β] | |
|---|---|---|---|---|---|
| Acc. Number | Protein Description | M | F | M | F |
| PBANKA_050450 | cytoplasmic dynein intermediate chain, putative | • | | | • |
| PBANKA_080230 | ubiquitin transferase, putative | • | | | • |
| PBANKA_090620 | conserved *Plasmodium* protein, unknown function | • | | | • |
| PBANKA_093990 | U6 snRNA-associated Sm-like protein LSm4, putative (LSM4) | • | | | • |
| PBANKA_103870 | conserved *Plasmodium* protein, unknown function | • | • | | |
| PBANKA_113640 | conserved *Plasmodium* protein, unknown function | • | | | • |

TABLE 5-continued

A PSMA reanalysis of the existing *Plasmodium berghei* male and female gametocyte proteome using the current iteration of the genome revealed significant changes in the assignment of male and female proteins.

| | | Previous [α] | | Current [β] | |
|---|---|---|---|---|---|
| Acc. Number | Protein Description | M | F | M | F |
| PBANKA_120490 | conserved *Plasmodium* protein, unknown function | • | | | • |
| PBANKA_123400 | vacuolar ATP synthetase, putative | • | | | • |
| PBANKA_141440 | exportin-T, putative | | • | • | |

[α] See reference (11).
[β] PepArML-Search MASPECTRAS2 Analysis (PSMA).

Importantly, two proteins that were highlighted [cf original Table 1 in (11)] as male-specific based on separation of gametocytes expressing GFP under the control of a sex-specific promoter, the Dynein heavy chain (PBANKA_092540) and Dynein heavy chain (PBANKA_041610) retained the same partitioning. The 6-cysteine protein, P230p (PBANKA_030600), was previously described to be male-specific and we find this to hold true following PSMA re-analysis as well. There were two proteins, the transmission-blocking vaccine candidate, P48/45 (PBANKA_135960) and the male development gene 1 (PBANKA_143220), which were not previously reported in the original proteomic study of *P. berghei* gametocytes, but following PSMA, we noted that these two previously described male-specific proteins (19, 20) were indeed present in the original raw dataset and in our reanalysis did not exhibit sex-specific partitioning. Further interrogation of the data suggests that P48/45 appear to be enriched (3.25-fold based on spectral counts) in *P. berghei* males as opposed to females (FIG. 10). Interestingly, despite its moniker, male development gene 1 (MDV1) appeared to be less enriched in males as opposed to females based on our PSMA reanalysis, which follows the report by Lal, et al., (2009), wherein it was shown that MDV1 is in both males and females but is particularly important for female gametocyte development (21). Although it was recently shown that the egress of male gametes is partly dependent on MDV1 (22). We also noted that a dynein heavy chain protein (PBANKA_050730) that did not partition to either sex appears to have a 74.5-fold enrichment in males. Conversely, we also determined that another dynein heavy chain protein (PBANKA_021400) appears to be enriched 67-fold in females. A kinesin (PBANKA_145880), which has not been fully described to date, was enriched 36-fold in the male fraction. The CCp1/LCCL1 domain containing protein (PBANKA_130070), which was hypothesized to be female specific (23) was also found in both male and female fractions, but was 63-fold enriched in the male fraction. The osmiophilic body protein (PBANKA_146300), a putative female-specific protein was found in both male and female fractions and is 27-fold enriched in the female fraction. These sex-specific enrichments are significant and strongly support the notion that while MS sensitivity enables their detection in the fraction, these fractions are likely unable to isolate completely male- or female-specific proteins. However, evidence from the literature is borne of both *P. berghei* and *P. falciparum* studies, and it remains to be seen whether *falciparum*-specific expression and sex-partitioning mirrors that of *P. berghei*.

We anticipated differential partitioning following PSMA, since we had also observed that a direct comparison of the Pb PSMA lists with the published Pb sex-specific lists resulted in only 136 shared male-proteins (FIG. 2E) and only 70 shared female-proteins (FIG. 2H). Moreover, we observed that there are 100 proteins from the original male-specific dataset (278) that are also found in the PSMA conserved male and female proteins (762 proteins). We could therefore account for only 178 male proteins of the original 278 male-specific proteins. In addition to the 70 shared female-specific proteins, we found that 85 proteins from the original female-specific dataset were also in the PSMA conserved male and female protein list (762 proteins). We could therefore account for only 86 female-specific proteins of the original 171 female-specific proteins. Altogether, re-analysis of the available *P. berghei* mature gametocyte proteome data by PSMA has significantly improved the quality of this data set. We used this new annotation for comparison with the *P. falciparum* NF54/Dd2 stage V proteome data.

Systematic Subtractive Protein Bioinformatics Analysis (SSB) to Partition Male and Female Stage V Gametocyte Proteomes.

Figure 8A:
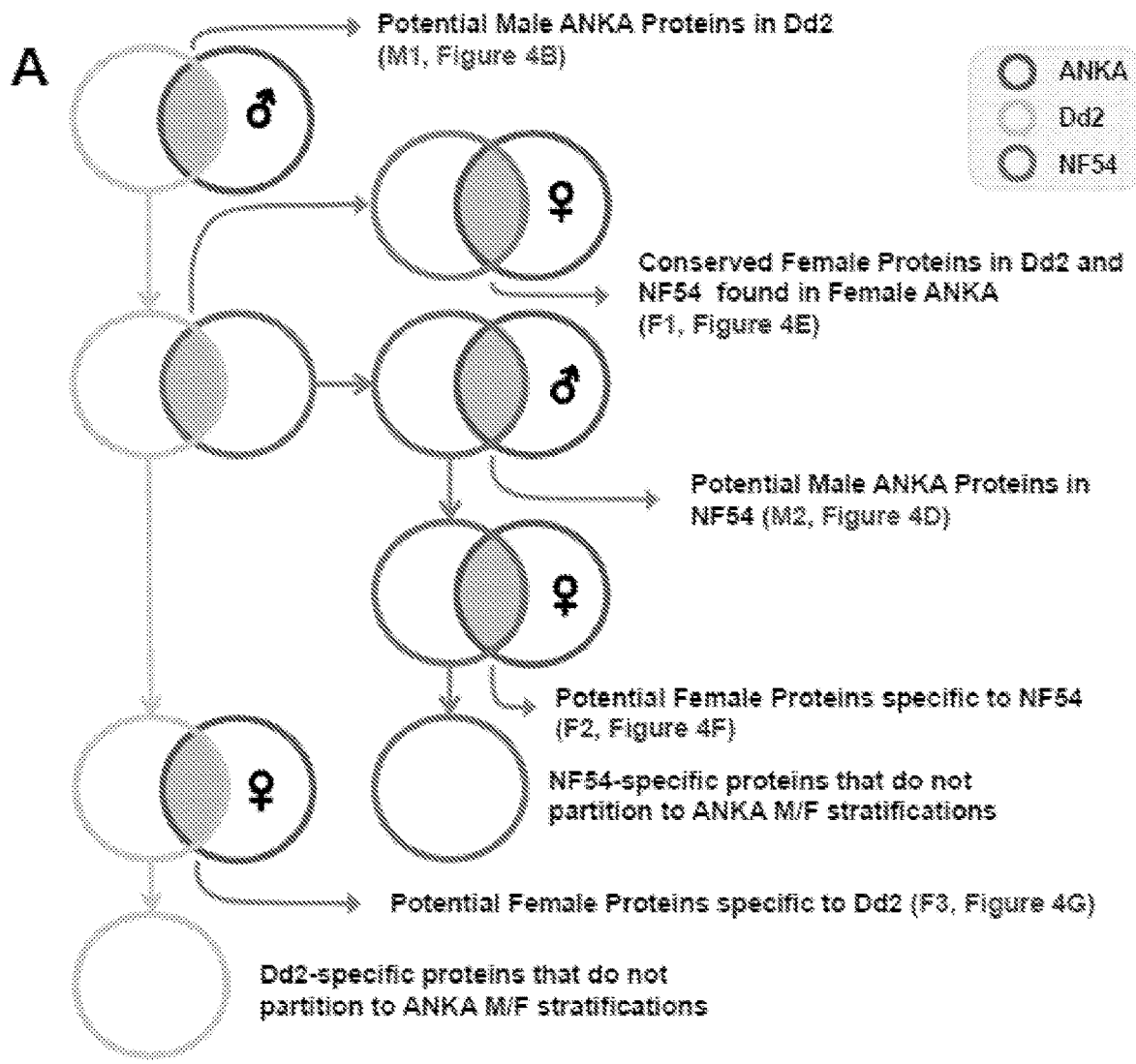
FIG. 8A-B. To define the male and female proteomes of *P. falciparum* stage V gametocytes we employed a SSB work-flow using the re-analyzed *P. berghei* mature gametocyte proteome data as a reference. See FIG. 1C and FIGS. 3B-G.
Figure 8B:
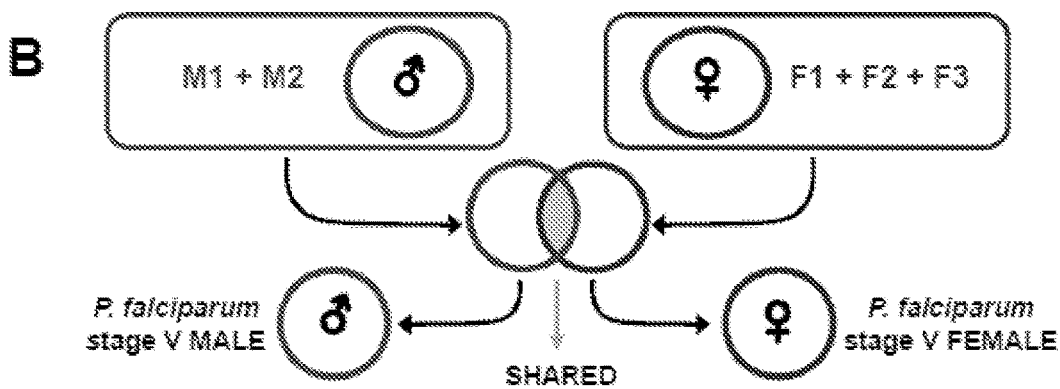

To define the male and female proteomes of *P. falciparum* stage V gametocytes we employed a SSB work-flow using the re-analyzed *P. berghei* mature gametocyte proteome data as a reference (FIG. 1C, FIG. 8). This approach is based on the assumption that sexual development is fundamentally evolutionarily conserved across the genus, although not all proteins will sex-partition similarly between the different lineages. Thus, the re-analyzed *P. berghei* male/female gametocyte PSMA datasets along with the proteome of a mutant *P. falciparum* clone, Dd2, which is defective in male gametocyte development, permit the sex-specific partitioning of our mixed-sex NF54 stage V gametocyte proteome. Integral in this process is using the known or strongly supported *P. falciparum* male/female gametocyte proteins as positive control markers (e.g., P47). This will allow us to track their partitioning throughout the SSB workflow (FIG. 4B-G).

Figure 4A:
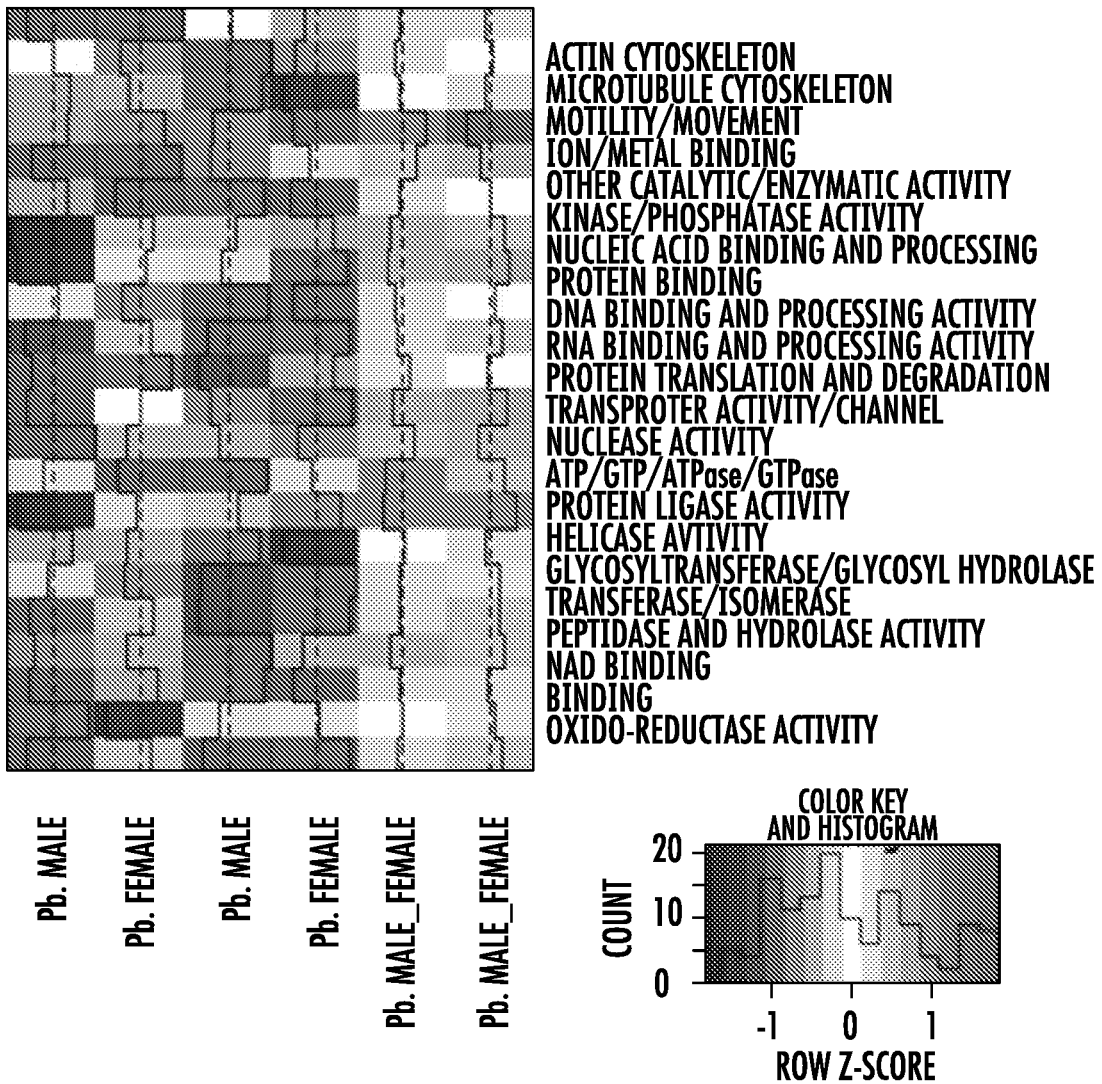
FIG. 4A-4B. Analyses of GO molecular function and signatures of selection in male and female *P. falciparum* proteins. (A) Enrichment analysis of GO molecular function terms in *Plasmodium berghei* and *Plasmodium falciparum*. Z-scores are shown as representation of enrichment, color coded as the key in top left corner. Histogram shows general distribution of enrichments across all samples. Histograms along columns show exact enrichment amounts. Column normalization for total proteins detected was performed by calculating total number of GO terms divided by total proteins detected. For simplicity, GO terms were reduced to 22 categories and enrichment calculated over these. (B) Genetic diversity within a parasite population is represented by PiN across 25 parasite isolates from Senegal and divergence between parasite populations is represented by Fst when comparing the Senegalese isolates with a set of parasite strains from Papua New Guinea (PNG). Several as yet uncharacterized sex-specific genes (i.e., PF3D7_1430800 and PF3D7_0131600) show high levels of divergence suggesting that they are under strong diversifying selection.
Figure 4B:
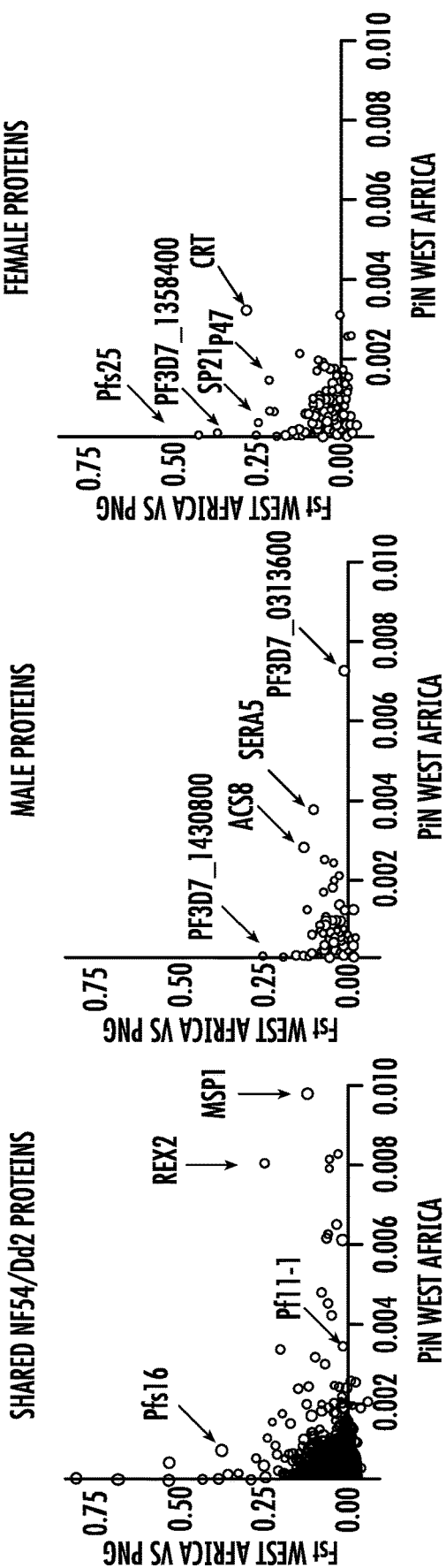

Step 1. We curated the Dd2 proteome by first identifying Dd2 proteins that are conserved in the male *P. berghei* PSMA (ANKA-M) dataset and generating a new list of male-subtracted proteins, i.e., female-enriched proteins (Dd2-FE; 1258 proteins). The male proteins that are shared with Dd2 are set aside (Dd2-M; 79 proteins) (FIG. 4B).

Step 2. This set was then combined with the mixed-sex protein list from NF54 to identify proteins that are conserved between Dd2-FE and NF54 and are likely to be enriched in female specific proteins (Dd2-FE/NF54; 1045 proteins; FIG. 4C). The proteins that are excluded from the overlap are then used to generate a list of likely male-enriched proteins (NF54-ME; 658 proteins) and Dd2-FE specific proteins (Dd2-FE-SP; 213 proteins) (FIG. 4C).

Step 3. The NF54-ME protein list is then used to search the *P. berghei* male-specific gametocyte protein list (ANKA-M; 366 proteins) to identify orthologs by BLAST (FIG. 4D). *P. falciparum* NF54 proteins with syntenic matches in the male *P. berghei* list are likely to be genus conserved and male-specific (NF54-M; 155 proteins). The NF54-ME proteins that do not have matches are likely to be NF54-specific proteins (NF54-SP; 503 proteins).

Step 4. The Dd2-FE/NF54 (1045) protein list was used to search the *P. berghei* Female-specific gametocyte protein list (ANKA-F; 418 proteins) to identify orthologs by BLAST. This analysis identified 181 proteins conserved between the two datasets, and 864 proteins that are Dd2-FE/NF54-specific and 237 proteins that are specific to *P. berghei* females (FIG. 4E).

Step 5. The NF54-ME list (male-enriched, 658 proteins) was used to determine if there are proteins that are conserved with the ANKA-F (female, 418 proteins) list. We surprisingly found 60 proteins that are conserved between ANKA-F and the putative male-enriched NF54-ME protein subset. Following the comparison, we noted that 598 proteins are likely to be highly enriched with male-specific *P. falciparum* proteins.

Although we did not anticipate missing proteins that do not partition to each of the subsequent protein lists, we nonetheless performed a set of additional data filtering steps as follows:

Determine if there are any overlapping proteins between NF54 F (181 proteins) and ANKA-M (366 proteins). This filtering step was performed to check that we had erroneously assigned a female protein that was actually found in the ANKA-M list. As expected no overlapping proteins were observed (data not shown).

Determine the overlap of between Dd2-M or "M1" protein list (79 proteins) and the NF54-M or "M2" protein list (155 proteins) to assess Dd2 vs. NF54 specific protein subsets. We observed 60 conserved proteins between these two lists, and these conserved proteins represent the putative *P. falciparum*-specific male gametocyte proteins. Proteins that are conserved between these two divergent *P. falciparum* lines were categorized as conserved *P. falciparum* male proteins (conserved Pf-M; 60 proteins). Interestingly, 19 proteins were found to be specific to only Dd2 (Dd2-M-SP) and 95 proteins were NF54-specific (NF54-M-SP).

Determine if there are proteins that are conserved between NF54-M or "M2" list (male-specific, 155 proteins) and the ANKA-F (female, 418 proteins) list. The NF54-M list was predicted to be highly enriched in male-specific proteins and we observed, as we had expected in this quality check of the data, no overlap with *P. berghei* female proteins.

Determine if there are proteins that are conserved between NF54-SP (503 proteins) with the ANKA-F (418 proteins) list. We identified 60 proteins, and these were set aside and categorized as NF54-SP-female proteins (NF54-SP-F) for subsequent inclusion in the *berghei*-driven female-specific list. The remaining 443 proteins, which were not shared with Dd2 or present in the *P. berghei* dataset, were considered NF54-specific proteins, non-sex partitioning (or potentially *P. falciparum* male-specific) (FIG. 4F).

Determine if there are proteins that are conserved between Dd2-FE-SP (213 proteins) and the ANKA-F (418 proteins) list. We identified 17 female proteins that appear to be completely Dd2-specific (Dd2-SP) in our analysis (FIG. 4G). Since we expected that all of the Dd2-FE-SP were gametocyte female-specific proteins, we hypothesized that the remaining 196 proteins from this list are Dd2-specific, non-(sex) partitioning.

Determine if there are proteins that are conserved between Dd2-FE/NF54 (1,045 proteins) and ANKA-M (366 proteins) list? As expected, we did not identify any contaminating males in this protein list since, in theory, the Dd2-FE is female enriched and thus any matching proteins from the mixed NF54 gametocyte stage V proteome, should be female-specific (data not shown).

The systematic steps described above allowed us to assemble a list of putative cross-strain (NF54-Dd2) *P. falciparum* male (Pf-M) and female (Pf-F) stage V gametocyte protein lists. Our initial Pf-M list, which was a grouping of NF54-M and Dd2-M proteins, identified 174 proteins; while our Pf-F list, which was a grouping of NF54-F, Dd2-SPF, and NF54-SPF proteins, identified 258 proteins. Of note there were marked differences in the composition of the Pf-M and Pf-F protein lists from either NF54 or Dd2, with the latter contributing only 11% of the proteins for Pf-F and 33% of the proteins for Pf-M.

Partitioning of Male- and Female-Specific Gametocyte Proteins in *P. falciparum*.

Pf-MALES.

Of those described to be male specific in *P. berghei* (11), we noted that the Mitogen-activated protein kinase 2 (MAP2; PF3D7_1113900), the Dynein light chain type 2 (PF3D7_1114000) were also only found in the male proteome in *P. falciparum*). The ortholog of the second *P. berghei* dynein heavy chain (PF3D7_0905300), which was originally described to be male-specific as well, was found to be non-sex partitioning. The 6-cysteine protein, P230p (PF3D7_0208900), which was previously described to be male-specific in *P. berghei* and confirmed in our PSMA analysis was also found to be male-specific in *P. falciparum*. The same was noted for the NIMA-related kinase 1 (NEK1; PF3D7_1228300), which was also male-specific in *P. falciparum*. The ortholog of the *P. cynomolgi* and *P. vivax* sperm-specific protein Don Juan (PF3D7_1413200) was found to be male specific. This protein was not found in the FS Asx and $FSg^{I-II}$ databases, but Florens, et al., (2002) apparently detected the protein in highly synchronized trophozoites(9). One of the top male-partitioning proteins in *P. berghei* (PBANKA_050730) (11) was detected in our total NF54 gametocyte stage V proteome but the ortholog (PF3D7_1023100) did not partition to either sex. PBANKA_050730 was already found to be shared in *berghei* males and females so it would naturally not partition in *P. falciparum*, since the male- and female-specific *berghei* lists were used to guide the assembly of the male and female lists in *P. falciparum*.

Pf-FEMALES.

Our dataset supports the argument that both the NIMA related kinase-4 (NEK4, PF3D7_0719200) and LCCL/CCp3 (PF3D7_1407000) proteins are conserved between *P. berghei* and *P. falciparum* female gametocytes. We also noted that NIMA related kinase 2 (NEK2, PF3D7_0525900) partitioned to females. A functional NEK2 has been shown to be essential for human/murine parasite development in the mosquito and its expression appears to be female gametocyte specific (24). The ortholog of the *P. berghei* female-specific Dynein heavy chain (PF3D7_0729900) did not partition to either sex. Interestingly, P28, which is expressed as a transcript in gametocytes and only translated during gametogenesis, was identified in the female proteome. Although there are clearly differences in the conditions of gametocyte cultures as opposed to in vivo development, which may lead to the misexpression of P28 protein, it is also possible that female gametocyte activation may have occurred during cell harvest. Our data however, clearly supports the current hypothesis that P28 is female-specific. Approximately 46% of the 299 proteins (138) are conserved proteins with unknown function and represent a rich set of potential female markers for subsequent study.

We then took the Pf-M (174 proteins) and Pf-F (258 proteins) proteomes that were generated above to identify proteins that are conserved in the asexual trophozoite and the earlier gametocyte stages I-II, as described above, to further refine our *P. falciparum* male/female Stage V proteomes (Pf-M' and Pf-F', respectively). We also sought to identify any potential overlapping proteins that may have partitioned "artificially" according to the *P. berghei* PSMA lists but in fact are non-sex partitioning in *P. falciparum* and found none (data not shown).

Comparison of Predicted Functions of Male- and Female-Specific Gametocyte Proteins in *P. berghei* and *P. falciparum*.

Figure 3A:
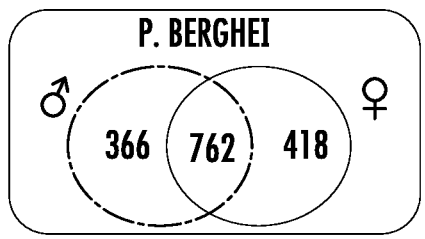
FIG. 3A-3H. Results from the Systematic Subtractive Protein Bioinformatic Approach (SSB). (A) Male and Female *P. berghei* protein identification following the re-analysis of the published dataset. (Refer to FIG. 2) (B-G) Detail overlap results from FIG. 8. (H) Partitioned *P. falciparum* male (174) and female (258) specific proteins.
Figure 3B:
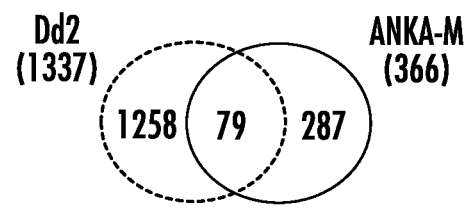
Figure 3C:
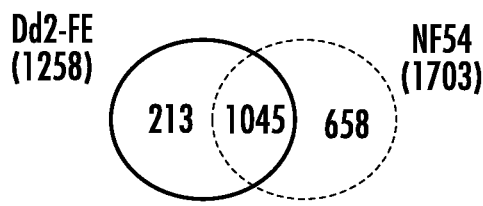
Figure 3D:
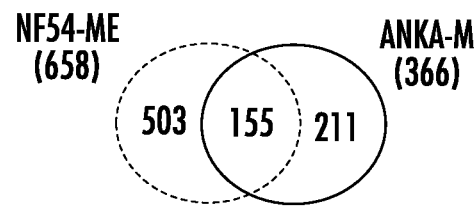
Figure 3E:
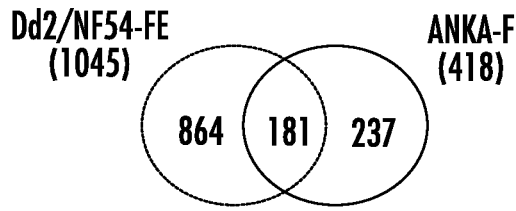
Figure 3F:
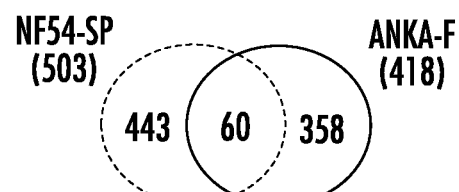
Figure 3G:
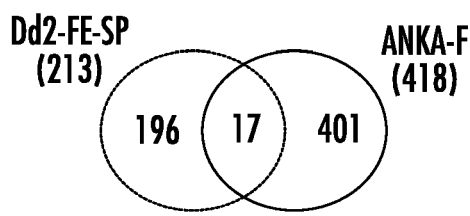
Figure 3H:
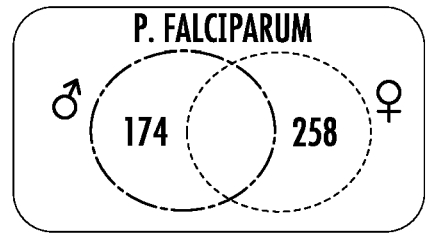

To identify potential functional differences in male vs female gametocytes based on the proteomics data, we measured enrichment of molecular function based on Gene Ontology (GO) terms in the male and female protein data sets from both *P. berghei* (FIG. 3A) and *P. falciparum* (FIG. 3H). Indeed we identified enrichment of GO terms relating to cell motility and movement as well as microtubule cytoskeleton in the male gametocyte proteins, reflecting the exflagellation process during male gamete maturation (FIG. 4A). Conversely the analysis identified GO term enrichment in female proteins for RNA binding and processing as well as for protein translation, relating to the translational repression mechanism that allows or just-in-time protein expression in the female gamete. The relevance of other enriched functions such as particular enzymatic activities in male (kinase, phosphatase) and female gametocyte proteins (transferase, isomerase, and oxidoreductase) remains to be determined.

Signatures of Natural Selection in Male and Female Gametocyte Proteins.

All the major transmission blocking vaccine candidates (i.e., Pfs25, P47 and P230) are not exposed to the human immune system during infection (unless the infected RBCs are cleared) but become functional upon mosquito infection when they present on the gamete and/or ookinete surface and interact with host factors. For example, P47 has an important role in immune evasion that contributes to the differential susceptibility of *A. gambiae* M and S strains to *P. falciparum* infection (25). The immunomodulatory role of P47 is reflected in unusual population structure with fixed differences between African and non-African parasite populations (26, 27). To systematically test for signatures of natural selection in the genes encoding the sets of male and female *P. falciparum* gametocyte proteins, we determined the rate of single nucleotide polymorphisms (SNPs) within a parasite population in Senegal (West Africa), and between this West African parasite population and a population from Papua New Guinea (26) (FIG. 4B). As a measure of balancing selection within the Senegalese population, we calculated SNP 7E (N) for each gene based on a sequence comparison of a total of 25 sequenced parasite isolates (28). SNP 7E (N) quantifies the number of pairwise non-synonymous differences amongst the set of strains analyzed. As a measure for positive selection between populations, we also calculated Fst for each gene by comparing the genetic diversity within the African parasite population with the diversity in the PNG parasite population. As predicted, P47 showed one of the highest Fst levels amongst all the male and female proteins (FIG. 4B). Interestingly, the female gametocyte marker and major vaccine candidate Pfs25 has an even higher value, reflecting strong positive selection potentially due to selection of gamete recognition and compatibility. In addition, several hypothetical proteins are encoded by genes with high Fst such as the male-specific gene PF3D7_1430800 and the female-specific gene PF3D7_1358400. Except for one gene encoding a conserved hypothetical male protein PF3D7_0313600, the sex-specific gene set shows significantly lower diversity within the African population than known markers of balancing selection such as MSP1 or SERA5. This would suggest that none of the male and female-specific proteins described here interact with the human immune system, either because these proteins are not present on the infected RBC surface or because of their low abundance during human infection.

Identification of *P. falciparum*-Specific Gametocyte Sex Proteomes.

Figure 5A:
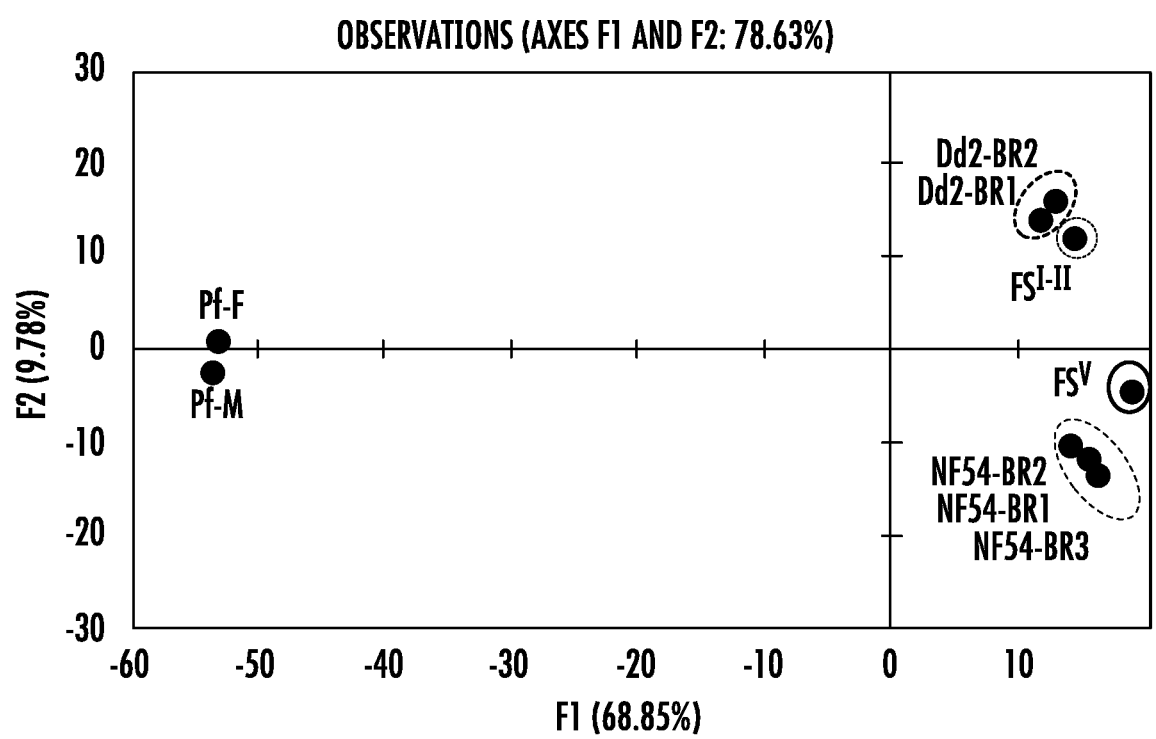
FIG. 5A-5I. Principal components analysis (PCA) and SSB analyses for the identification of *P. falciparum* male-specific proteins that are lost as a result of the Dd2 male development defect. (A) PCA was performed on Male and Female Specific *P. falciparum* stage V proteomes (Pf-M and Pf-F, respectively), two biological replicates (BR1 and BR2) from Dd2, three biological replicates (BR1-3) from NF54, FSgV (3D7/NF54 stage V) and FSg$^{I-II}$ (3D7/NF54 stage I-II). Proteins with at least 10 spectral counts averaged across all proteomes were used for qualitative protein analysis. (B/C) Stage-specific analyses identifies 354 putative *P. falciparum*-specific male (B) and 177 female (C) gametocyte proteins. (D-G) Stage-specific analysis identifies 843 gametocyte-specific proteins in the NF54 proteome (D), of which 216 are also present in Stage I/II and 627 are only expressed in more mature gametocyte stages (E). The same analysis identifies in Dd2 533 gametocyte-specific proteins (F) of which 189 are present in Stage I/II while 344 are only expressed in Stage III and later (G). (H/I) Stage-specificity of male and female Dd2 proteins reveals limited overlap between Stage I/II and conserved male *P. falciparum* proteins (H), but significant overlap and between Dd2 Stage III-V and *P. falciparum*-specific female proteins (I).
Figure 5B:
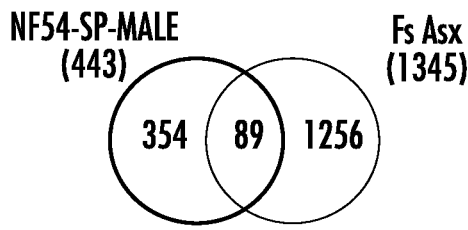
Figure 5C:
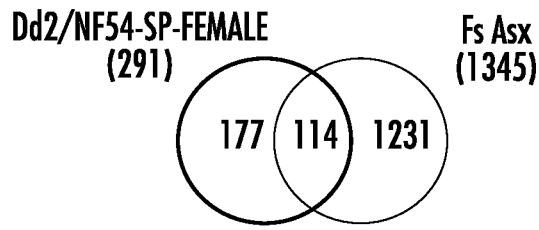
Figure 9A:
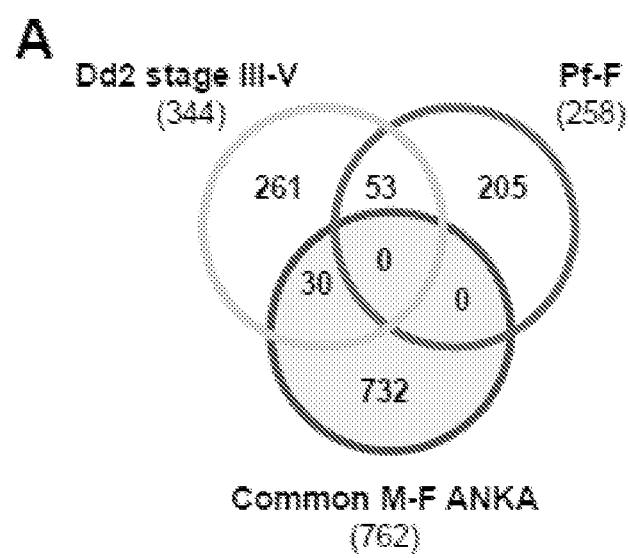
FIG. 9A. Expanding the Pf-Female protein list to include those that are not 2 stage V-specific (to capture putative stage III-IV proteins) does not result in additional 'female hits' in the Dd2gIII-V 523 list.
Figure 9B:
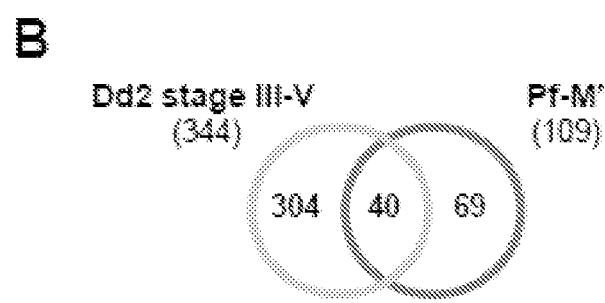
FIG. 9B. A comparison A comparison of the Dd2gV 528 stage-V specific protein list with the Pf-M (*P. falciparum* 529 male-specific) protein list identified 40 conserved proteins, which may include stage III male candidate markers.

Once we had assembled the male- and female-specific protein lists based on conservation with *P. berghei*, we sought to determine if we can derive through the SSB approach the *P. falciparum*-specific sex partitioned protein lists. We first performed a principal components analysis using male and female-specific *P. falciparum* stage V proteomes (Pf-M and Pf-F, respectively), replicate Dd2 and NF54 stage V gametocyte proteomes, as well as $FSg^V$ and $FSg^{I-II}$ protein lists (FIG. 5A). As expected the PCA clearly demonstrated enrichment for stage V proteins in NF54. To derive the putative male-specific stage V protein list, we compared the NF54-specific male list (443 proteins) with the FS Asx protein list and identified 354 proteins that likely represent the non-conserved *falciparum*-specific male proteome (FIG. 5B). To derive the putative female-specific stage V protein list, we first removed 573 proteins that are shared between Dd2FE/NF54-SP (864 proteins) and the ANKA Male-Female Common (762 proteins) protein lists. This step effectively filtered out proteins that would still be present in the Dd2-FE/NF54-SP list and that are conserved between *falciparum* and *berghei*. From this *P. falciparum* female-specific protein list (291 proteins, FIG. 5C), we filtered out proteins that are also found in the FS Asx (1345 proteins) set to identify 177 stage V-specific female proteins (FIG. 9B). We were cognizant that the FS Asx dataset may not have captured all the late trophozoite or schizont/ merozoite proteins that may be present in our samples, since GlcNAc treatment never completely removes all persisting asexual stages from a gametocyte culture. These "missed" asexual proteins are highlighted in the respective male and female lists (Tables S6A and S6C). Considering the presence of obvious merozoite/schizont contaminants, we conservatively assembled a list of 339 male and 174 female stage V specific proteins.

Figure 5D:
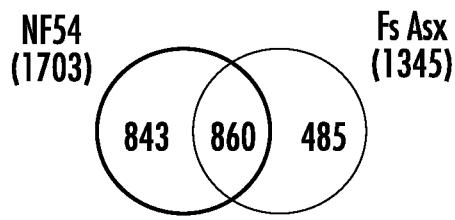
Figure 5E:
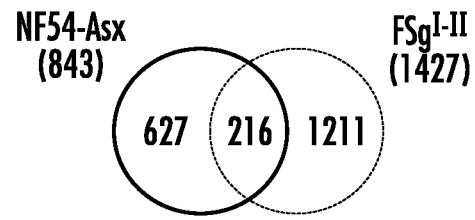

We further determined the degree of NF54 stage V specificity of proteins to stage V gametocytes by comparing $DTg^V$ with the FS Asx protein lists and noted that 860 proteins were conserved (FIG. 5D). These 860 proteins comprise 50% of the total $DTg^V$ proteome, and may represent proteins that are simply conserved between trophozoites and stage V gametocytes, or potential contaminating proteins that are present in the culture, despite the treatment with GlcNAc. Of the remaining 843 proteins from $DTg^V$, 216 proteins were found to be conserved in the $FSg^{I-II}$ dataset, indicating that these proteins are expressed early in gametocytogenesis and remain present on stage V gametocytes, given the apparent absence of stage I-II in the culture, as determined by microscopy (see above). The remaining 627 proteins that did not match with either the FS Asx or $FSg^{I-II}$ datasets, represents a potential pool of stage III-IV gametocyte markers in addition to those that are present in stage V. Of these 627 proteins, 422 proteins (67%) were identified in the membrane fraction and supported by GO predictions for cellular component and biological process. Of the 627, 188 proteins (30%) have predicted transmembrane domains and 52% (325/627 proteins) of which are conserved hypothetical proteins. Several previously described proteins appear in this putative list of Stage III-V markers, including four LCCL domain-containing proteins CCp2 (PF3D7_1455800), CCp3 (PF3D7_1407000), CCp5 (PF3D7_0109100) and FNPA (PF3D7_1451600), which all have hypothesized adhesive functions (23). CCp3 and CCp5 were found to be female-specific proteins in our analyses. The NIMA related kinases, NEK2 (PF3D7_0525900) and NEK4 (PF3D7_0719200) are also found in this list and categorized as female-specific proteins as well. There are 95 male-specific proteins present in this list, including the two dynein heavy chain proteins (PF3D7_1122900 and PF3D7_0905300). This short list of proteins represents a pool of well-studied targets that may be used to specifically select stage III gametocytes from culture.

Identification of the Stage-Specific Male/Female Protein Markers as an Indicator for Stage Transition and to Investigate the Stage-Specific Dd2 Defect.

Since Dd2 is defective in the production of mature, stage V male gametocytes (15), we hypothesized that the Dd2 proteome is more enriched in the stage I-II gametocytes, representing the small subset of rectangular and tear-drop forms that we had described from the Dd2 culture (Table 2). Following PCA analysis, we observed that Dd2 clustered with gametocyte stages I-II proteins, which likely reflects the arrested male gametocytes in this strain. Moreover, the male specific and female specific stage V proteomes appear to be distinct from all other clusters. The PCA also shows biological reproducibility of our proteome, as NF54 and Dd2 replicates cluster clearly.

Figure 5F:
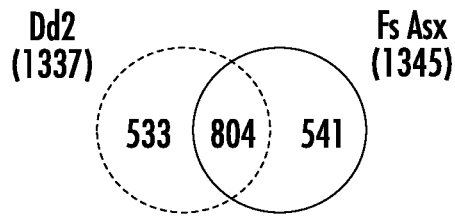
Figure 5G:
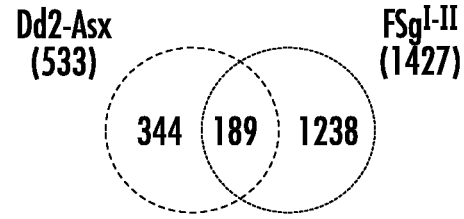

To identify the putative arrest of male gametocytes in Dd2 candidate male protein markers, we also sought to further narrow the Dd2 stage V gametocyte dataset into stage specific proteins, and thus compared the Dd2 gametocyte stage V proteome (1,337 proteins), referred to as $Dd2g^V$, with the FS Asx and $FSg^{I-II}$ datasets. We noted that 804 proteins were conserved between FS Asx and $Dd2g^V$ datasets (FIG. 5F). Of these, 603 Dd2 trophozoite-conserved proteins are also found in the NF54 trophozoite-conserved subset. These 603 proteins comprise 56% of the total $Dd2g^V$ proteome, and may similarly represent proteins that are conserved between trophozoite and stage V gametocytes, or contaminating proteins that remain present in the GlcNAc-treated culture. Of the remaining 533 proteins from $Dd2g^V$, 189 proteins were found in the $FSg^{I-II}$ dataset as well (FIG. 5C, indicating that these proteins are expressed early in gametocytogenesis and remain present on female stage V gametocytes. For Dd2, we found 344 proteins that are stage V-specific. Of these stage V proteins, 227 proteins (66%, 227/344) were identified in the membrane fraction, 62% (142/227 proteins) are conserved hypothetical proteins with diverse predicted GO functions and 89% (127/142) of these proteins have predicted transmembrane domains.

Figure 5H:
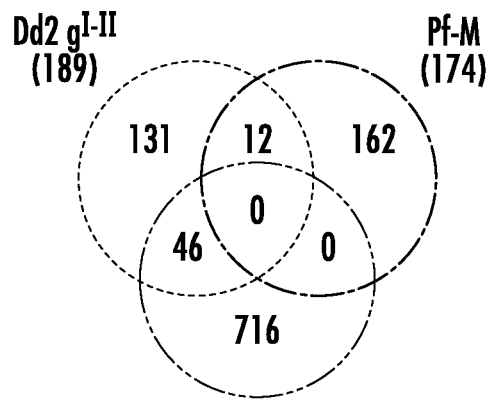

Since Dd2 is defective in producing morphologically distinct stage V males, we examined whether the 189 Dd2 proteins shared with $FSg^{I-II}$ are enriched in male gametocytes (FIG. 5H). We found that only 12 proteins were common between the Pf-M protein list (174 proteins) and the $Dd2g^{I-II}$ set. These 12 proteins are also shared between the Pf-M and NF54-SP protein list, which is potentially male-specific, and the $Dd2g^{I-II}$ set (data not shown). Of these 12 proteins, 2 proteins PF3D7_0508200 and PF3D7_1215100 had corresponding transcript markers for immature gametocytes (29), and were also thus absent from the stage V-specific Pf-M protein list (109 proteins). As expected, 46 proteins were found in $Dd2g^{I-II}$ list that are orthologs of proteins that were shared between males and females in *P. berghei*. Twelve of these proteins have ~2-fold (or greater) enrichment in males in *P. berghei*. Although we cannot be certain that the same fold-enrichment exists for *falciparum*, based on these analyses, only 24/189 (13%) of the $Dd2g^{I-II}$ proteins are male; suggesting no male-specific enrichment. This is not unexpected given that the 162 remaining Pf-M proteins may be expressed only at stage III or IV during gametocytogenesis.

Figure 5I:
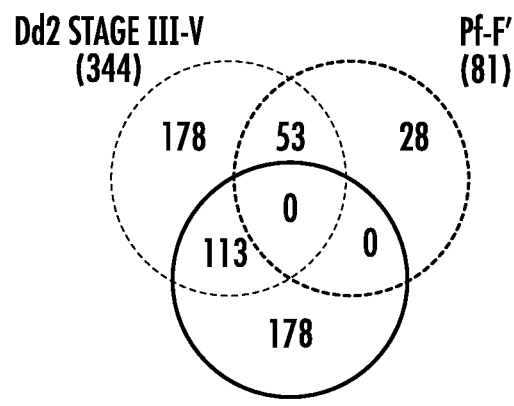

We also examined whether the 344 Dd2 proteins that are specific for Stage III-V are enriched in female proteins (FIG. 5I). To test this hypothesis we looked for proteins in the Dd2g$^V$ stage-V specific protein list that are also found in the Pf-F (291 *P. falciparum* female-specific proteins) list that we had generated previously, which we then refined to only stage V-specific female proteins, Pf-F' (81 proteins). We observed that 28 proteins were not found in the Dd2g$^V$ stage-V specific protein list, and 53 proteins were conserved, suggesting that only 15% (53/344) of the Dd2g$^{III-V}$ specific protein list were in the combined Dd2/NF54 female protein list. It is possible that the number of mature stage V females in Dd2 with the full protein complement is low; falling below the identification criteria threshold used in this study. There are 113 proteins that are shared between Dd2/NF54-SP Females and Dd2, which gives a total of 164 female-specific proteins in the Dd2g$^{III-V}$ list. The lack of enrichment in female proteins in this list may suggest that a significant proportion of the 178 Dd2g$^{III-V}$ proteins (Tables 57J) are male-female shared proteins or stage III males. In fact, only 26/178 (15%) of these proteins have orthologs in the ANKA male-female shared protein list. Moreover, expanding the Pf-Female protein list to include those that are not stage V-specific (to capture putative stage III-IV proteins) does not result in additional 'female hits' in the Dd2g$^{III-V}$ list (FIG. 9A). Moreover, of the 291 proteins that remain partitioned to Dd2g$^{III-V}$, only 10% (30/291) have orthologs in the male-female shared protein list. Assuming that the developmental defect in Dd2 extends beyond the presence of mature males and also results in slower maturation of females, the 178 Dd2/NF54-SP female proteins may represent the remaining complement of mature stage V proteins.

A comparison of the Dd2g$^V$ stage-V specific protein list with the Pf-M (*P. falciparum* male-specific) protein list identified 40 conserved proteins (FIG. 9B), which may include stage III male candidate markers. We found that two conserved proteins of unknown function, PF3D7_1413200 and PF3D7_1235800, had corresponding stage specific transcript markers for immature gams, i.e., stages II-IV (29) and another conserved protein, PF3D7_1404200 had a corresponding mature (stage V) gametocyte transcript marker. The remaining 69 proteins may represent a pool of candidate stage IV-V male gametocyte markers. Indeed, we found that of the 10 proteins with corresponding stage-specific transcript markers, 5 were mature stage V gametocyte proteins, and 3 corresponded to young (stage I) or immature (II-IV) gametocytes. Two of the 10 proteins were predicted to be ring-stage specific, which are likely contaminants in the sample and the last protein did not have a predicted profile that was captured by the defined stages used in the Joice, et al. (2013) study (29).

Validation of the Sex-Specificity for a Subset of Female Protein Markers.

Figure 6:
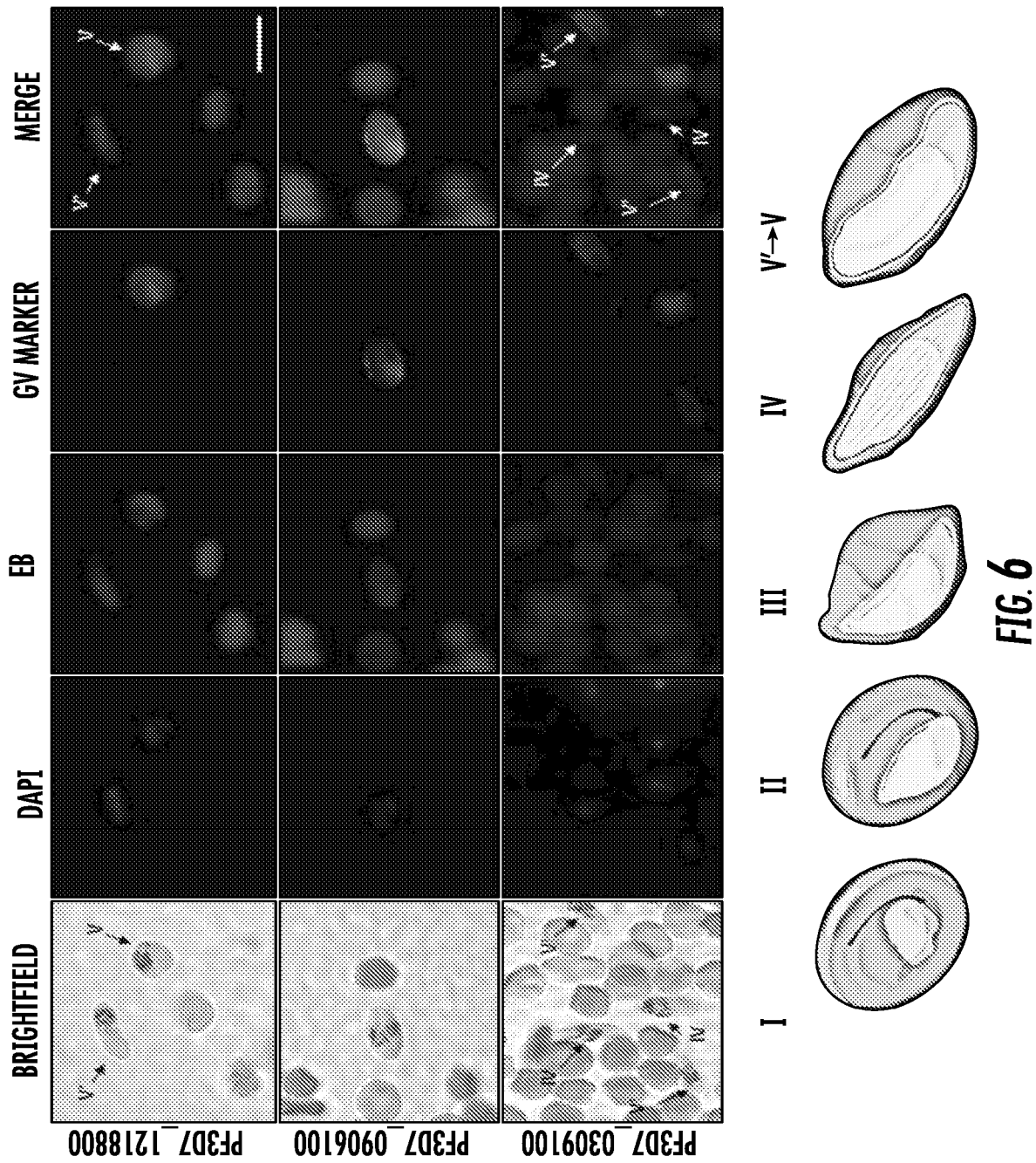
FIG. 6. Immunofluorescence analysis and validation of antibodies elicited against putative male- and female-specific gametocyte stage V proteins. Antibodies were raised in mouse against PF3D7_1218800, PF3D7_0390100 and PF3D7_0906100. Lower panel, cartoon depicting the various stages of NF54 gametocyte development, especially stages IV and V, which we predict would be the primary stage present in a day 18 gametocyte culture. Gametocytes that are labeled V' are considered mature stage V parasites, and those labeled V, are considered complete "falciform" (crescent) shaped stage V gametocytes. EB, Evans blue counter stain for protein, and appear red. GV (gametocyte stage V marker antibodies) are detected with Alexa488-conjugated secondary antibodies and appear green. DAPI stains nuclear DNA and appears blue. Scale bar=10 μm.
Figures 7A, 7B, 7C:
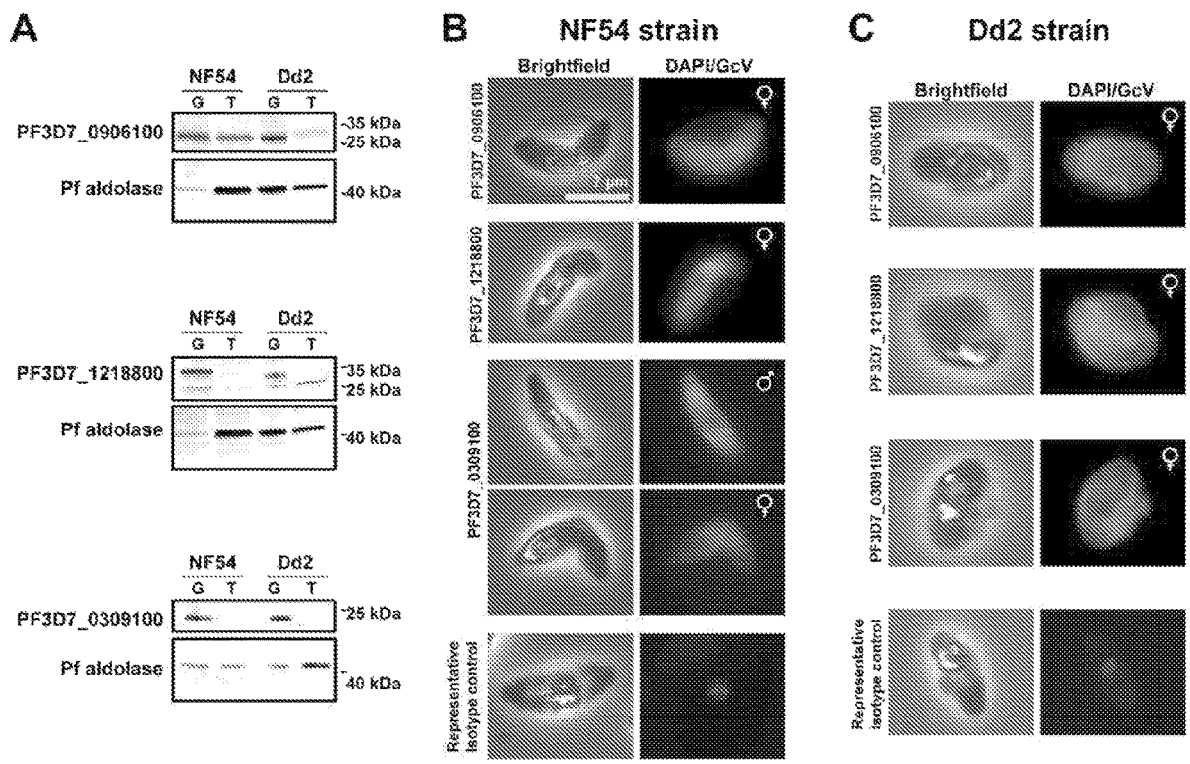
FIG. 7A-7C. Western blots and immunohistochemistry using NF54 and Dd2 strains validate female stage V gametocyte specificity for two of three candidate protein markers. (A) Western blots of total day 18 stage V gametocyte and synchronized trophozoite protein lysates using the respective antibodies along with anti-*P. falciparum* aldolase antibodies used as a loading control. Western blots showed that PF3D7_1218800 and PF3D7_0309100 were present in female gametocytes (Dd2 is defective in mature male gametocyte development), yielding bands in gametocyte but not trophozoite samples for both NF54 and Dd2. Antibodies to PF3D7_0906100 stain gametocytes and trophozoites from NF54 but primarily stains Dd2 gametocytes. (B) Representative results for fluorescence immunohistochemistry of strain NF54 along with an isotype control. PF3D7_1218800 and PF3D7_0906100 were found to be female specific (green). PF3D7_0309100, which is an ortholog of a putative female specific protein in *P. berghei* is not sex-specific in *P. falciparum*. (C) Representative results for fluorescence immunohistochemistry of strain Dd2 along with an isotype control. PF3D7_1218800, PF3D7_0906100, and PF3D7_0309100 were all found to stain female parasites (green), as Dd2 fail to produce mature stage V male gametocytes. Parasite sex was microscopically determined using published morphological characteristics of male and female gametocytes along with spatially distinct DAPI staining (blue) of DNA. Female gametocytes have condensed DAPI staining whereas male gametocytes have diffused DAPI staining.

We successfully generated mouse antibodies to three proteins (PF3D7_1218800; PF3D7_0906100; PF3D7_0309100). PF3D7_1218800, PF3D7_0906100 and PF3D7_0309100 were selected based on their predicted female-specificity using the ANKA male and female proteomes. We tested the stage specificity of these antibodies by staining NF54 male and female gametocytes (FIG. 5) and noted that antibodies for all three proteins stained fully "falciform" stage V gametocytes from day 17 cultures. Interestingly, PF3D7_0309100 appears to differentiate falciform from stage IV-V transitioning gametocytes, i.e., elongated gametocytes with no relaxing of the ends to those gametocytes with more pronounced curvature but not completely falciform (30). The antibodies were further validated by western blot analysis to assess stage specificity (FIG. 6A). We found that the anti-PF3D7_0906100 antibodies recognized a ~28 kDa protein band (predicted $M_r$=21.9 kDa) in both day 17 gametocyte and synchronized trophozoite lysates from NF54 and Dd2. However, the staining intensity appeared to be more pronounced for NF54 gametocytes and less so for Dd2 trophozoites. Anti-PF3D7_1218800 antibodies recognized a ~37 kDa protein band (predicted $M_r$=39.6 kDa) and a lower MW band around 26 kDa in NF54 and Dd2 gametocytes only. However, the antibodies also recognized a similar lower $M_r$ band, ~26 kDa in the Dd2 trophozoite sample. The exact nature and identity of this protein band is not clear at present, but given the developmental defect in Dd2 during gametocytogenesis, we cannot rule out the possibility of dysregulated protein expression in the asexual stages of Dd2. Anti-PF3D7_0309100 antibodies appear to be highly specific to gametocytes in both NF54 and Dd2.

We further determined sex-specific staining by the antibodies using the morphological characteristics of male and female gametocytes (15) along with strong DAPI co-staining of DNA (FIG. 6B). Of the three antisera tested, two (PF3D7_1218800 and PF3D7_0906100) were found to be female specific. Antibodies to PF3D7_0309100, which is found in the "NF54-Dd2 Common Proteins", stained both males and females (FIG. 6B-C). PF3D7_0906100 also referred to as a putative Developmental Protein was identified in our Dd2 stage V gametocyte protein list and in the Trophozoite protein list (8) and was therefore not included in any of the stage V specific male and female protein lists. Although the ortholog in *P. berghei* (PBANKA_041520) was included in the Female-specific protein list for *P. berghei*, a close examination of the spectral data revealed that it was identified by a single peptide only in a single replicate batch of purified females. It is likely that this protein exists in both males and females in *P. berghei*.

Discussion

One of the major caveats of the SSB approach is that the analysis is limited by the proteome size and accuracy of categorization. We recognized, a priori, that we are likely to miss out on a few potential male or female proteins, as we had noted in the comparison of our dataset with the previously published, FSg$^V$ mixed-sex proteome. However, it is also clear that given the differential efficiencies in proteome acquisition across MS approaches, the community must consider using the combined databases in their proteome mining studies for proteins of interest. For example, we were able to corroborate the identification of the non-(sex) partitioning, PIESP2 (PF3D7_0501200) in stage I-II and stage V gametocytes. It is a putative exported parasite-infected erythrocyte surface protein, with a predicted PEXEL motif, in stage V gametocytes. PIESP2 was notable in that transcript for this protein is virtually absent in stages I-II and stage V gametocytes (PlasmoDB) and it was also found to be potentially on the RBC membrane surface in asexuals and during liver stage development.

We had also observed the consistent partitioning of Dd2-specific proteins following our comparisons with the NF54 (DTgV) and the 3D7/NF54 (FSgV) stage V proteomes. Proteomic analyses of Dd2 has not been performed to date, but this observed partitioning is really unexpected as we would expect that the differences in gene content between the two *falciparum* strains should probably be minimal. While we have begun a partial analysis of the Dd2 developmental defect by identifying the enrichment of stage and male-specific proteins, the morphological differences observed even for the mature female Dd2 gametocytes suggest that the defect may also result in dysregulated expression of proteins that would not normally be present during 'normal' gametocytogenesis.

From a translational perspective, we have provided sex-specific information for several stage-specific gametocyte transcript markers that can be used to analyze blood samples taken during surveillance studies in malaria endemic countries. In the same vein, the antibodies that we have generated in this study may ultimately represent novel diagnostic markers for gametocyte carriage in the blood or other body fluid (e.g., urine or saliva) of infected but asymptomatic individuals. PF3D7_0906100 (conserved hypothetical protein), PF3D7_0309100 (a putive development gene) and PF3D7_1218800 (putative secreted ookinete protein, PSSP17) have not been well characterized to date. Previous attempts to knock out PSSP17 in *P. berghei* were unsuccessful and highlight the importance of this protein in parasite development in the asexual blood stages as well. The complete characterization of each of these proteins is the focus of current efforts in our laboratories, as they have potential as new transmission-blocking vaccine targets and/or sex-specific biomarkers of gametocyte carriage.

Example 2: Development of a Rapid Diagnostic Test (RDT) for Asymptomatic Gametocyte Carriers

*Plasmodium falciparum* sexual stage gametocyte parasites do not cause disease but are critical for transmission of the malaria parasite through the mosquito vector from one human to another. To date, no simple point of care diagnostic to identify gametocyte carriers and individuals with submicroscopic asexual stage parasitemia exists. Current rapid diagnostic tests (RDTs) do not have enough sensitivity to identify such carriers. PCR is the only commonly used method for identifying, but it is costly and cannot be done in a rural health clinic in malaria endemic regions throughout the world. Current RDTs use blood as the biological sample source and in many countries in malaria endemic countries, cultural blood taboos exist, thereby limiting the usefulness of sampling blood from individuals who are not sick but are carriers. The present inventors have identified malaria parasite biomarkers for parasite carriage in the saliva of asymptomatic children in Cameroon and Zambia. Antibodies have been developed that can identify the sexual stage gametocyte in human saliva.

In particular embodiments, saliva is used as a biological source for parasite protein biomarkers (DNA has been the primary target). Antibodies (non-monoclonal) can already identify female-specific gametocyte proteins in saliva. No other group has been able to identify unequivocally more than 3-4 parasite proteins in saliva. The present inventors have identified 61 parasite proteins.

Because saliva is hypotonic, the present inventors hypothesized that infected red blood cells in the oral cavity vasculature carrying either asexual or gametocyte stages are carried by the gingival crevicular fluid (GCF) into saliva and lyse, releasing parasite-derived proteins into saliva, which can then be collected in a small volume. The GCF is a serum ultrafiltrate tissue fluid that seeps into the gingival sulcus from gingival connective tissue and the vasculature through thin sulcular epithelia. Periodontitis-related inflammation results in the further thinning of the sulcular epithelial membrane barrier. In turn, this results in an increase in GCF and an increase in serum transudate, including red cells and neutrophils. Gingivitis or periodontitis in general is widespread in developing countries. The present inventors hypothesized that due to potential gametocyte stage V sequestration in capillary beds, the extensive capillary loop structure and periodontitis that gametocyte and asexual stage parasitized red cells can transfer into the GCF, which mixes with saliva. The infected red cells then lyse in saliva releasing its parasite-derived proteins.

A low cost, non-invasive RDT with greater sensitivity is needed in malaria endemic countries, especially in those countries where current control methods are working. These countries are entering the pre-elimination phase and as they progress, the epidemiology of the disease changes from sick to carrier state. The current RDTs do not work in identifying these carriers. As described herein, the present inventors have generated the sex-specific (male/female) proteomes of *Plasmodium falciparum* stage V gametocytes. Sixty-one *P. falciparum* proteins have been identified in the saliva of asymptomatic children.

In addition, the present inventors identified a female-specific, gametocyte protein across several samples. The present inventors also have developed antibodies against this protein and demonstrated its sex and stage specificity. To date, 392 saliva samples have been collected from asymptomatic children and comprehensively analyzed. The target female gametocyte protein has been identified in >90% of the samples.

Furthermore, the present inventors have identified the target protein in about 12 microliters of saliva (unconcentrated) from several samples using the antibodies by western blot. They have also demonstrated the identification of the HRP2 protein from *Plasmodium falciparum* asexual stages in about 12 microliters of unconcentrated saliva samples by commercially available monoclonal antibodies on a western blot.

Paired-blood samples analyzed by current RDTs or by expert microscopy or PCR/RTPCR have been collected and analyzed. The present inventors were able to identify asymptomatic carriers using the antibody to probe the human saliva at a level matching PCR/RTPCR. Blood samples that were analyzed using a current RDT were found to be negative, but positive by PCR and western blot.

We have identified 61 parasite-derived proteins in the saliva of asymptomatic children in Cameroon and detected and quantified a novel gametocyte-specific marker in a total 392 samples (12 unblinded and 380 blinded) from Cameroon and Zambia. We produced an antibody that is specific for this gametocyte protein in 12 μl of filtered, non-concentrated saliva from children who were determined to be negative by either a HRP2 rapid diagnostic test or expert microscopy from blood samples, but positive by PCR. We also demonstrated that anti-HRP2 antibodies recognize cognate antigen in the saliva of these asymptomatic individuals. Thus, the antibody-mediated detection is at the level of PCR-sensitivity.

Targeted Biomarker Discovery & Sensitivity Analyses Using Laboratory Samples.

Acquisition of the required baseline data and optimal analytical parameters prior to the analysis of the unblinded and blinded field samples.

We developed a robust, liquid chromatography tandem mass spectrometry (LC-MS/MS) analytical approach using a quadrupole time-of-flight (QTOF) instrument at a sensitivity of ~10-33 gametocytes/μL (33 μL saliva digested peptides spiked with different amount of gametocytes protein digested peptides) and have surpassed the expected number of parasite-specific proteins that can be detected and identified in an artificial saliva sample containing serial dilutions of stage V gametocyte culture-derived parasite proteins.

We also developed a robust and simple workflow for the collection of unstimulated saliva in the field and the stabilization of host and pathogen-derived proteins in the saliva sample.

As described herein, we also produced mouse polyclonal antibodies against three gametocyte proteins. We noted that one protein, PSSP17/PF3D7_1218800 (FIG. 12A), a conserved, secreted protein from female gametocytes was among the 61 proteins detected across different saliva samples from asymptomatic children (FIG. 11). The fact that the male: female gametocyte ratio is generally skewed towards females provides additional support for selection of this protein as a gametocyte biomarker. We also selected a conserved hypothetical asexual protein (PF3D7_0507800) from this list of 61 that was also present within a majority of the saliva samples to confirm that other asexual antigens can serve as a biomarker.

Targeted Biomarker Discovery & Sensitivity Analyses Using Field-Derived Samples.

Acquisition of the potential spectrum of parasite-derived proteins from the saliva of asymptomatic children in Cameroon.

We collected 12 samples from 5-15 yr old children from Cameroon through a school-based sampling approach of children who were asymptomatic (of any febrile illness). Our LC-MS/MS analysis captured 61 of the most abundant parasite proteins from a pool of five different saliva samples from asymptomatic children; ~20-fold higher than what was previously reported from Gambian children with suspected malaria (Huang, et al., 2012). These proteins represent potential novel biomarkers of parasite carriage but do not likely exemplify the complete repertoire of malarial parasite proteins in saliva.

We then developed a more sensitive LC-Multiple Reaction Monitoring MS (MRM-MS) assay (Carr et al., 2014) using the stable isotope dilution method with an internal standard diagnostic peptide (with stable isotope-labeled Arg/Lys residues) derived from PF3D7_1218800 and PF3D7_0507800 using existing samples. This assay would permit the relative and absolute quantification of the biomarkers in saliva.

Field Validation of Targeted Gametocyte Stage V Biomarkers.

Analysis of blinded samples of saliva (which would include ≥139 gametocyte positive samples and approximate the same number of gametocyte negatives+/− asexual parasitemia) from individuals recruited from malaria endemic countries.

We used the MRM-MS assay to determine the prevalence of two target candidate biomarkers PSSP17/PF3D7_1218800 and PF3D7_0507800 across a larger number of samples (N=392) from two countries with differing malaria transmission characteristics. We collected paired saliva-blood or saliva-RDT samples from individuals residing in Yaoundé, Cameroon (school-based sampling) and Nchelenge District, Zambia (household sampling), using the DNA genotek saliva collection device to collect 2 mL of saliva from asymptomatic children 5-15 years of age.

Figures 12A, 12B, 12C, 12D, 12E:
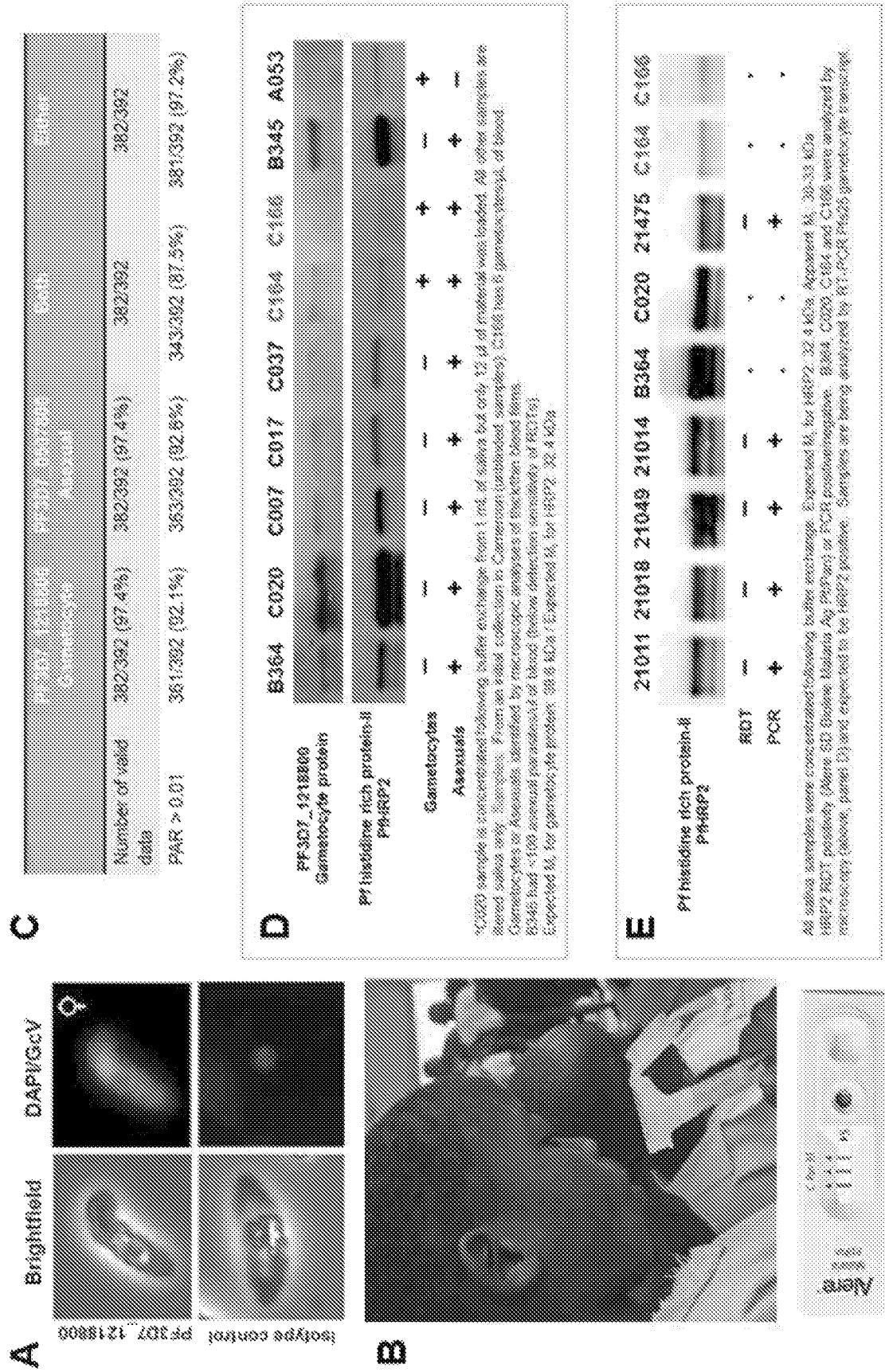
FIG. 12A-12E. Assay development for the analysis of saliva samples from asymptomatic children from Cameroon and Zambia. (A) Immunofluorescence assays of *Plasmodium falciparum* stage V gametocytes (GcV) stained by mouse antibodies(green) raised against the respective proteins, which were previously determined to be female-specific gametocyte proteins since these are orthologs of *P. berghei* female gametocyte proteins. DAPI stains nuclear DNA and appears blue. (B) Saliva collection (2 mL total volume/individual) using the saliva collection device developed by DNA genotek was conducted in schools among asymptomatic children 5-15 years old (pictured) or at homes in Zambia (not shown). The lower image shows the rapid diagnostic test (RDT) made by Alere, i.e., the SD Bioline Malaria Ag Pf/Pan test used in Zambia. (C) We moved ahead with PF3D7_1218800 as a target biomarker for female gametocytes and a novel asexual protein, PF3D7_0507800, as potentially new biomarker for asymptomatic asexual carriage that we had originally confirmed to be present in the saliva of asymptomatic children from Cameroon (Tao, et al., unpublished) and designed a Multiple Reaction Monitoring MS assay. We found that of the 392 blinded samples total (350 from Cameroon/42 from Zambia), 392 had a strong signal for the internal standard peptide. We were then able to calculate the proportion of positive saliva samples. PAR is the peak area ratio of the target analyte's integrated peak area over internal standard's integrated peak area [2 pmol of internal standard in 10 µl were injected per sample]. (D) The antibodies to PF3D7_1218800 recognize the target in saliva suggesting that a RDT is indeed possible for human saliva detection of gametocytes (12 µl of 0.22 micron filtered saliva/well). Sample from C166 is from an 11 year old child with 6 gametocytes/µL. Monoclonal antibody against PfHRP2 recognizes its target in the filtered but unconcentrated saliva. Paired blood smears were analyzed for gametocytes (sexual) and asexual parasite stages from each individual providing the saliva sample. †CO20 sample is concentrated following buffer exchange from 1 mL of saliva but only 12 µl of material was loaded. All other samples are filtered saliva only. Samples (red font): From an initial collection in Cameroon (unblinded samples). B345 had <100 asexual parasites/ul of blood (below detection sensitivity of RDTs). Expected $M_r$ for gametocyte protein: 39.6 kDa/Expected $M_r$ for HRP2: 32.4 kDa. (E) Anti-PfHRP2 mAb recognizes HRP2 in filtered, concentrated saliva sample 15 µg loaded/well. Note that HRP2 does not ionize and cannot be detected by MS/MS, as evident in the lack of mass spectrometry evidence for this protein in PlasmoDB. Each sample from Zambia (case numbers 21,000 were analyzed by RDT at time of collection or by PCR for the *Plasmodium* cytochrome B gene from blood spots. All saliva samples were concentrated following buffer exchange. Expected $M_r$ for HRP2: 32.4 kDa, Apparent $M_r$: 30-33 kDa. HRP2 RDT positively (Alere SD Bioline Malaria Ag Pf/Pan) or PCR positive/negative. B364, CO20, C164 and C166 were analyzed by microscopy and are expected to be HRP2 positive. Blue (+) indicate positive for both gametocytes and asexuals by microscopy. The western blot suggests that antibody-mediated detection of HRP2 or PF3D7_1218800 (gametocyte protein) approaches the sensitivity of PCR and better than the gold standard microscopic identification.

We collected a total of 392 saliva samples from Cameroon and Zambia (FIG. 12B). Of these, 12 samples were unblinded and were part of the initial collection in May 2013. The remaining 380 samples were completely blinded in terms of (i) identity and demographic information, (ii) presence/absence of gametocytes and asexuals in paired thick and thin blood smears, (iii) results of the paired HRP2 RDT, and (iv) the results following the nested PCR amplification of the *Plasmodium* cytochrome B gene from paired dried blood spots.

We analyzed a total of 380 blinded samples from Cameroon (N=338) and Zambia (Nchelenge District, N=42), and 12 unblinded samples from Cameroon. Of the total samples analyzed, 392 gave highly reproducible spectra and were thus considered valid identifications. We observed that more than 90% of the saliva samples contained detectable levels of PSSP17/PF3D7_1218800 (gametocyte biomarker) and PF3D7_0507800 (asexual biomarker) and ~88% of the samples contained both biomarkers (FIG. 12C). The Peak Area Ratio (PAR) of >0.01 is the minimum threshold identified for an unequivocal identification and suggests potential abundance differences for each target biomarker in saliva.

We then directly tested the point of care bioassay potential of our targets by determining the capacity of anti-PF3D7_1218800 antibodies to detect antigen despite potential abundance differences across saliva samples (FIG. 12D). We have thus demonstrated that mouse antibodies that were generated against the stage V, female gametocyte-specific protein easily detected the target protein in a western blot using only 12 μl of saliva. Importantly, the saliva was only filtered through a 0.22 μm membrane to remove debris but remained otherwise unconcentrated. Using commercially available anti-Pf histidine rich protein-2 (HRP2) monoclonal antibodies, we were also able to demonstrate the abundance of HRP2 in saliva (FIG. 12E). To date, the identification of HRP2 by mass spectrometry has never been accomplished, owing to the intrinsic properties of this protein that affect detection of tryptic peptides by any mass spectrometry instrumentation using standard protocols. We now have proof-of-concept evidence that antibodies against known (HRP2) and novel (PSSP17) parasite proteins work directly on filtered and unconcentrated saliva.

Paired blood samples for each of the 338 blinded samples from Cameroon included thick and thin blood smears and 100 μl of finger-prick blood that was stored in RNAlater. The blood films were initially analyzed by microscopy at the time of collection and we subsequently determined if we can detect the presence of gametocytes in individuals that are microscopy negative by RTPCR amplification of the Pfs25 transcript (Bousema, et al., 2011; Mlambo, et al., 2008).

We have extracted RNA from 338 paired blood samples and have begun RT-PCR analyses. We were able to compare the various detection approaches, including MRM-MS, RDT, RTPCR/PCR and microscopy for a few samples to provide a general overview of the spectrum of observations thus far (FIG. 13). As we had shown previously for different saliva samples, our MRM results support our western blot data and easily identified asymptomatic carriers that would have otherwise been classified as negative by RDT or microscopy (gold standard). The RDT results for Case 21059 would likely have been interpreted to be a false positive, since the PCR analysis was negative. However, as clearly shown in FIG. 13, the saliva-derived western blot and MRM results suggest that the individual did in fact have parasitemia levels that should have been easily verified by PCR. Interestingly, although Pfs25 can be readily detected in the blood from individuals that are also microscopy positive for the presence of asexuals and/or gametocytes (data not shown), in some cases despite corroboration of negative microscopy data by RTPCR, we nonetheless identified the gametocyte protein in human saliva (Case D497 and C100).

For Case 20990, this individual would have been classified as parasite negative because PCR, RDT and microscopy data were corroborative.

As described herein, we report the unequivocal presence of P. falciparum asexual and stage V gametocyte-specific "biomarker" proteins in the saliva of subclinical/asymptomatic children from two malaria endemic countries. Our analysis of 392 saliva samples demonstrates that a large proportion of asymptomatic and gametocytemic children are left undetected by the current molecular, RDT and gold standard approaches; further underscoring the need for novel diagnostic tools to support malaria elimination and eradication efforts.

Example 3: Synthetic Gene Sequence for PSSP17 that is Codon-Optimized for E. coli Expression P. falciparum gametocyte diagnostic biomarker, PSSP17 (PlasmoDB.org accession #: PF3D7_1218800), which is a 39.6 kDa protein (394 amino acids) that is translated from a 1050 bp mRNA transcript. The natural sequence is published on PlasmoDB.org and can be accessed using that number. However, for the purpose of producing a highly immunogenic recombinant protein, only a subset of the entire protein sequence was selected based on physico-chemical properties of the protein including hydrophobicity, helicity, linearity, presence of predicted B cell epitopes and CD4+ T helper epitopes, surface exposure, and so forth, which yielded a 117 amino acid (351-bp) fragment. A synthetic (cDNA) 351-bp gene sequence for PSSP17 (SEQ ID NO: 7; amino acid sequence shown in SEQ ID NO:8) that is codon-optimized for expression in E. coli was then produced and subcloned to an expression vector to make the recombinant protein with a HIS tag for subsequent purification. The protein was then used to generate mouse and rabbit antibody against PSSP17 that exhibited high specificity for the target biomarker. It is envisioned that a quality and process controlled Research Cell Bank (RCB) is developed to ensure that the synthetic sequence-derived recombinant subunit PSSP17 can be made in large quantities for use as a positive control. The RCB is used as the seed line for downstream process development of clinical diagnostic grade material. The recombinant subunit protein is used to generate both a capture and detection monoclonal antibody for the saliva-based RDT for every production lot. The epitopes recognized by the monoclonal antibodies are mapped against the recombinant subunit protein and the antibodies themselves are sequenced. Importantly, the recombinant subunit protein is also provided as a critical component of the RDT kit as a positive control. Positive controls do not exist for the currently available RDTs that are being used to diagnose symptomatic malaria. These control proteins have been identified by the Foundation of Innovative New Diagnostics, the WHO, and Roll Back Malaria Program as a critical tool to allow ministries of health and end users in malaria-endemic countries to conduct random quality checks of RDT lots, many of which have been in storage for protracted periods of time and under different temperatures. It is therefore envisioned that, in particular embodiments, a lyophilized, highly standardized positive control is provided with each lot of the RDTs to ensure that RDTs from a given production lot are performing as claimed.

Example 4: Saliva-Based Malaria Asymptomatic & Asexual Rapid Test (SMAART)

We have developed a novel, point-of-care, non-invasive, rapid diagnostic test kit to identify subclinical carriers with very low levels of malarial parasites in their blood and biofluids. The test uses monoclonal antibodies, against a Plasmodium falciparum female gametocyte stage specific biomarker that we have observed to be present in saliva from 5 to 15 year old asymptomatic children in malaria endemic areas such as Cameroon and Zambia. SMAART (SSaliva-based Malaria Asymptomatic and Asexual Rapid Test) is a simplified, lateral flow immunoassay platform. The current sensitivity of SMAART is Europium chelate, visible fluorescence detection of 2-12 parasites/µL. Importantly, the current rapid diagnostic tests deployed in the field and that detect only asexual, malaria parasite antigens in the field have a sensitivity of about 200 parasites/µL of blood.

Figures 14A, 14B:
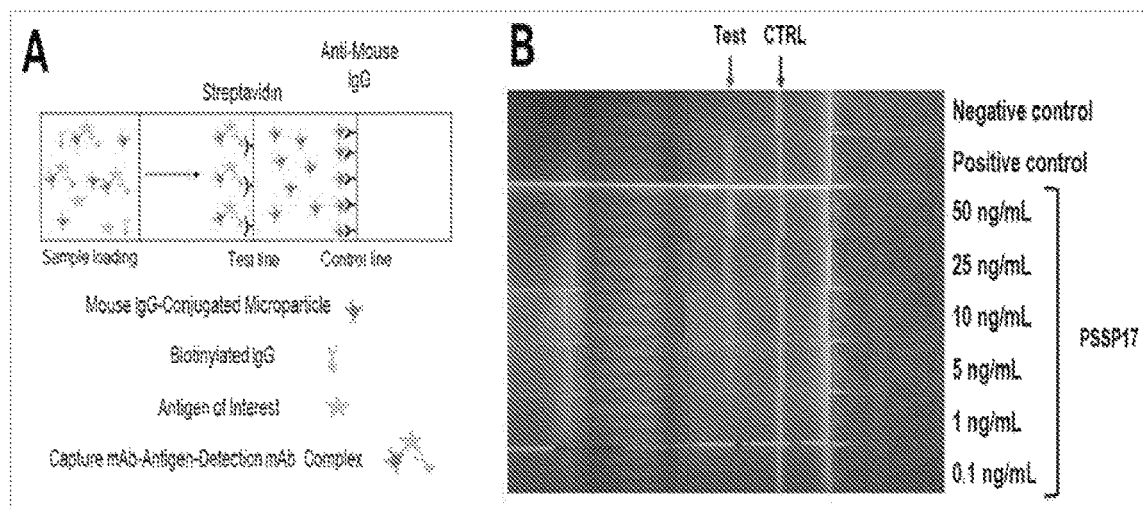
FIG. 14A-14B. Lateral Flow Immunoassay (LFIA) detection of the gametocyte specific proteins, PSSP17. (A) Schematic for the gRAD LFIA (BioPorto, Denmark). The readout in panel (B) is an image acquired by a camera phone.

FIG. 14. shows the Lateral Flow Immunoassay (LFIA) detection of the gametocyte specific proteins, PSSP17. (A) Schematic for the gRAD LFIA (BioPorto, Denmark). (B) Malaria gametocyte biomarker PSSP17 in 20 µL of solution (saliva) was captured by biotinylated anti-PSSP17 10E2.B7 and immobilized on the Test line, which is striped with streptavidin. Detection of PSSP17 was achieved by adding the EuChelate nanoparticle-conjugated anti-PSSP17 27C9.B5 mAb to the 20 µL reaction solution, and diluting out with 120 µL sample dilution buffer (SDB-50, BioPorto) to a final concentration of 140 µL. As a negative control, 100 ng/mL of PfHRP2 (final concentration in the reaction) was used as the spiked-in antigen and EuChelate labeled mAbs were detected on the control (CTRL) line as it is striped with anti-mouse IgG. As a positive control we used mature P. falciparum gametocyte lysate (estimated to be ~150 gametocytes/µL). The lower limit of detection of recombinant PSSP17 was between 1-5 ng/mL, which is about 3-12 gametocytes/4. The readout in panel (B) is an image acquired by a camera phone. In another embodiment, a phone application can convert the image into an inverted grayscale file that can perform relative quantification (densitometry) on the visible testy bands.

Figures 15A, 15B:
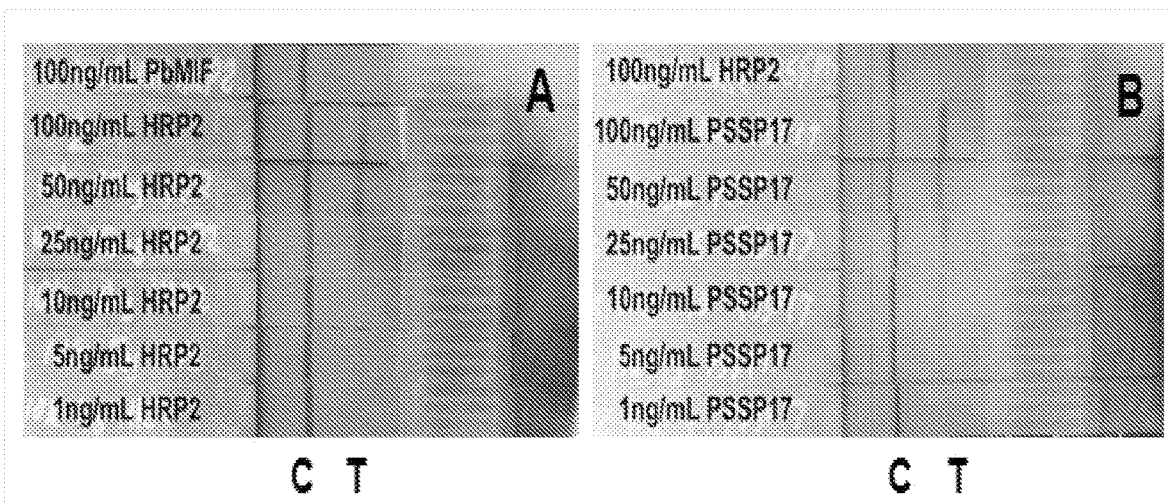
FIG. 15A-15B. Capture of PSSP17 in "spiked-in" samples of recombinant PSSP17 in malaria naïve human saliva. Determine LOD using spiked-in samples. (A) Recombinant PfHRP2 was spiked-in to naïve human saliva and tested by the SMAART-HRP2 Lateral Flow Immunoassay (LFIA). (B) Recombinant PSSP17 was spiked-in to 20 µL naïve human saliva and tested by the SMAART-PSSP17 LFIA. C, control line. T, test line.

FIG. 15. shows capture of PSSP17 in "spiked-in" samples of recombinant PSSP17 in malaria naïve human saliva. Determine LOD using spiked-in samples. (A) Recombinant PfHRP2 was spiked-in to naïve human saliva and tested by the SMAART-HRP2 Lateral Flow Immunoassay (LFIA). Recombinant PbMIF (an irrelevant parasite protein) was used as a spiked-in control. (B) Recombinant PSSP17 was spiked-in to 20 4 naïve human saliva and tested by the SMAART-PSSP17 LFIA. Recombinant HRP2 was used as a spiked-in control. LOD for PSSP17 was ~5 ng/mL (approximately 3-12 gametocytes/4 of blood), whereas the LOD for PfHRP2 was 25 ng/mL. The reaction time was ~15-20 minutes, and analyte concentration dependent. Fluorescence images were captured by camera phone and inverted. C, control line. T, test line.

Figures 16A, 16B:
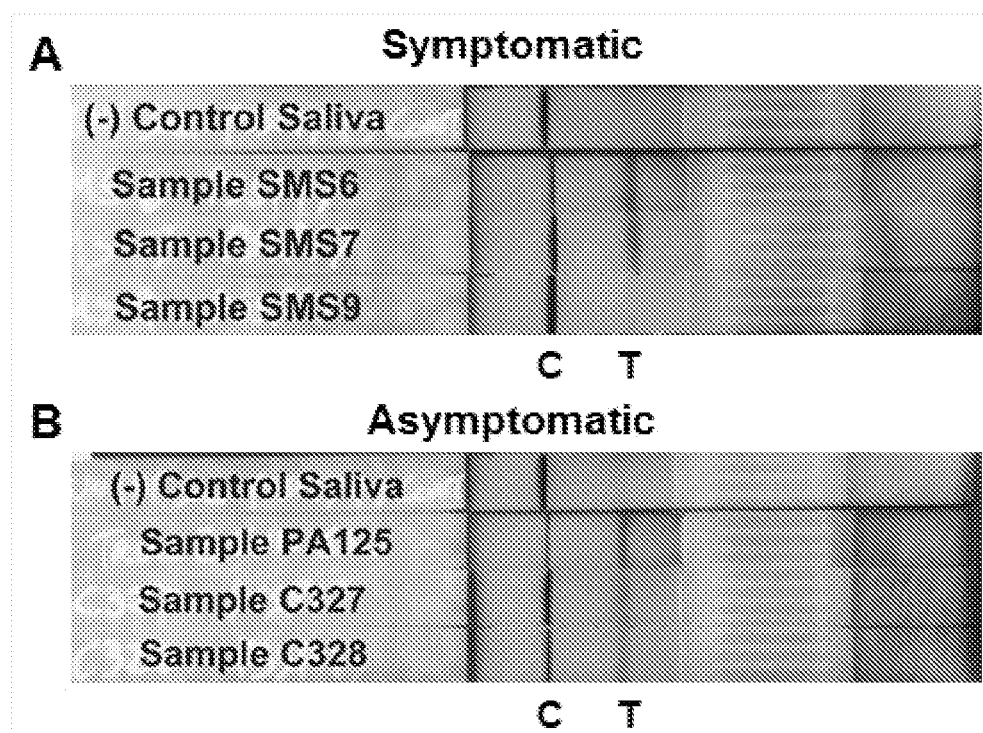
FIG. 16A-16B. Capture of native PSSP17 from saliva samples collected from asymptomatic and symptomatic children in Cameroon. Determined LOD using field samples. (A) PSSP17 was effectively captured from preserved, frozen saliva from three saliva samples from symptomatic children/young adults (5-19 years old) presenting at a clinic in Yaoundé, Cameroon. (B) PSSP17 was effectively captured from three preserved, frozen saliva samples from asymptomatic children from a primary school in Mfou, Cameroon. These tests used blinded samples. Control naïve human saliva (+HRP2) samples were analyzed in parallel.

FIG. 16. Shows the capture of native PSSP17 from saliva samples collected from asymptomatic and symptomatic children in Cameroon. Determined LOD using field samples. (A) PSSP17 was effectively captured from preserved, frozen saliva from three saliva samples from symptomatic children/young adults (5-19 years old) presenting at a clinic in Yaounde, Cameroon. (B) PSSP17 was effectively captured from three preserved, frozen saliva samples from asymptomatic children from a primary school in Mfou, Cameroon. These tests used blinded samples. Control naïve human saliva (+HRP2) samples were analyzed in parallel.

TABLE 6

Head to head comparison of SMAART vs. SD Bioline
RDT and the gold standard microscopy and PCR.

| Code | Age | Sex | RDT | Microscopy gametocytes/100WBC |
|---|---|---|---|---|
| SMS06 | 13 | M | POS | 0 |
| SMS07 | 19 | F | POS | 0 |
| SMS09 | 9 | F | POS | 0 |
| PA125 | 16 | M | POS | 0 |
| C327 | 11 | M | POS | 2 |
| C328 | 9 | F | POS | 5 |

Samples showcased in FIG. 16 were unblinded and found to have the following metrics. The apparent LOD for our studies is at the equivalence of ~2 gametocytes/1000 WBC or ~16 parasites/4 of blood (the known detection limit of microscopy) and undetectable by SD Bioline RDTs targeting the blood stage biomarker PfHRP2. All the individuals were SD Bioline RDT-positive for asexual parasites, but 4 samples were gam-negative by microscopy. Interestingly, given the repeated absence of false positives from our spiked-in/native saliva analyses (FIGS. 14-16), SMAART can potentially be faster (parallel analysis of samples) and more sensitive than the 30+mins/slide "gold standard" microscopy (i.e., <16 parasites/µL blood). Also, SMS9 (weakly positive) included sputum in the saliva sample, suggesting that even suboptimal samples remain useful with SMAART. We have shown that gram-negative, RDT-positive samples by microscopy are routinely found to be gram-positive by PCR.

Kit Components

Figures 17A, 17B, 17C, 17D, 17E, 17F:
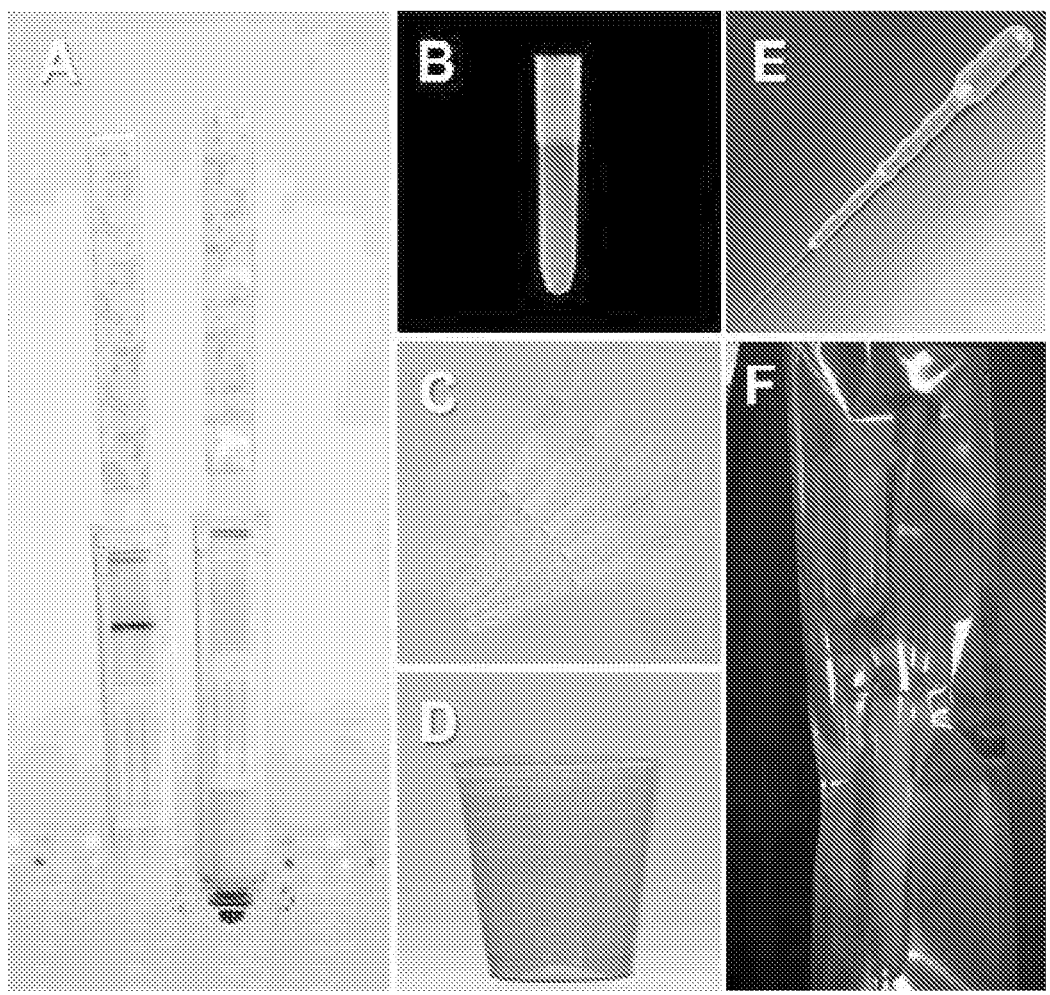
FIG. 17A-17F. Kit components.

In certain embodiments, the kit comprises ten (10) 1.2 ml microdilution tubes (Light Labs) containing lyophilized, biotinylated mAb 10E2.B7 for capture and EuChelate nanoparticle-conjugated mAb 27C9.B5 (FIG. 17A-B). The kit can also comprise ten (10) microdilution tubes containing lyophilized anti-PfHRP2 capture and detection mAbs (Arista Biologicals) (FIG. 17A-B). The kit can further comprise twenty (20) Lateral flow strips (FIG. 17C). Twenty (20) medicine cups (30 mL, Sarstedt, FIG. 1D) are provided for saliva collection by drool method and twenty (20) sterile, 1.5 ml fine tip transfer pipette for transferring ~15 µl of saliva (FIG. 17E) from the medicine cup to the microdilution tubes. The above components can be further partnered with saliva collection devices from many manufacturers, e.g., Oasis Diagnostics Pure. Sal™ device (FIG. 17F), Thermo Fisher Scientific's Oral Eze® device, DNA Genotek's OraGene® device or any derivation of the same or similar platforms. Furthermore, in the absence of a saliva collection device, small medicine cups such as those that are included in the kit can be used to collect saliva as per the described collection method below. Moreover, disposable paper or plastic cups that are available can be used in lieu of a medicine cup or a specific saliva collection device.

In particular embodiments, the kit comprises lateral flow strips, e.g., BioPorto's gRAD lateral flow immunoassay strips (N=20). In certain embodiments, the strips are striped with streptavidin at the test line and anti-mouse IgG in the control line. Twenty (20) strips are provided with a dropper of sample dilution buffer (SDB) enough for 20 reactions (FIG. 17C).

Figure 18:
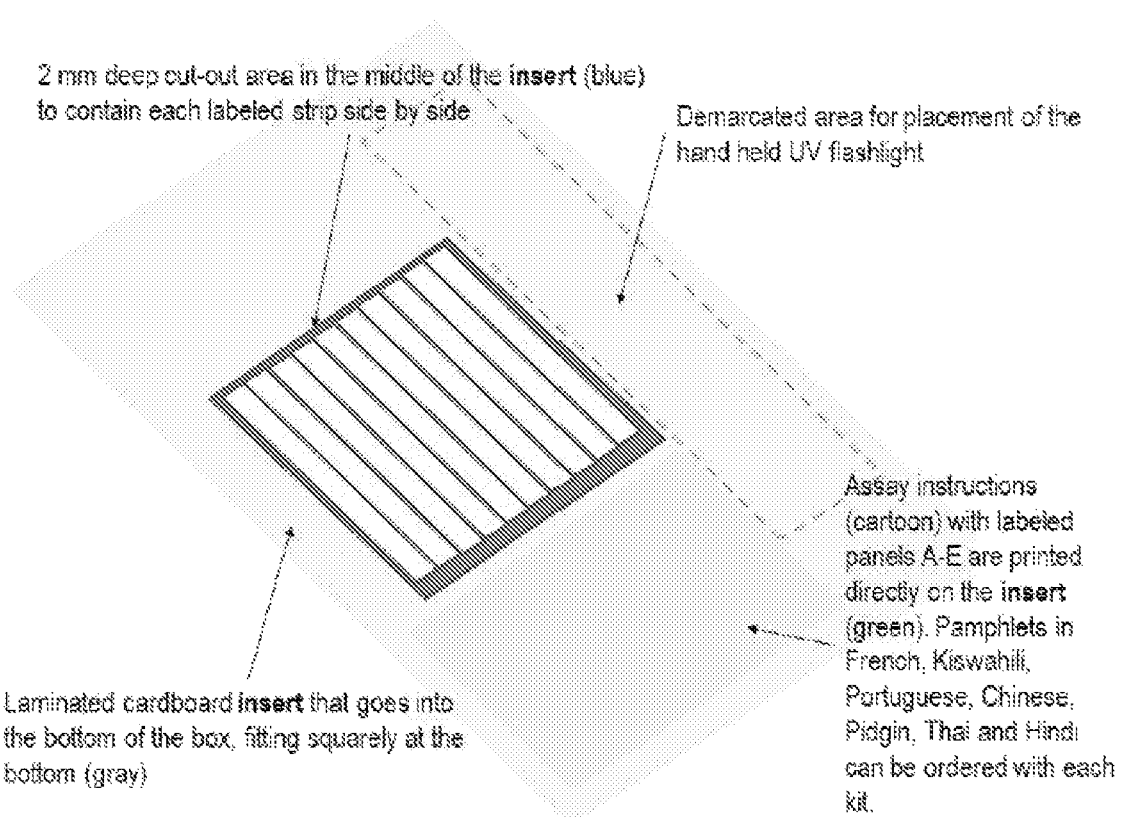
FIG. 18. Cardbox kit schematic showing the cardboard strip holder insert for imaging strips.
Figure 20:
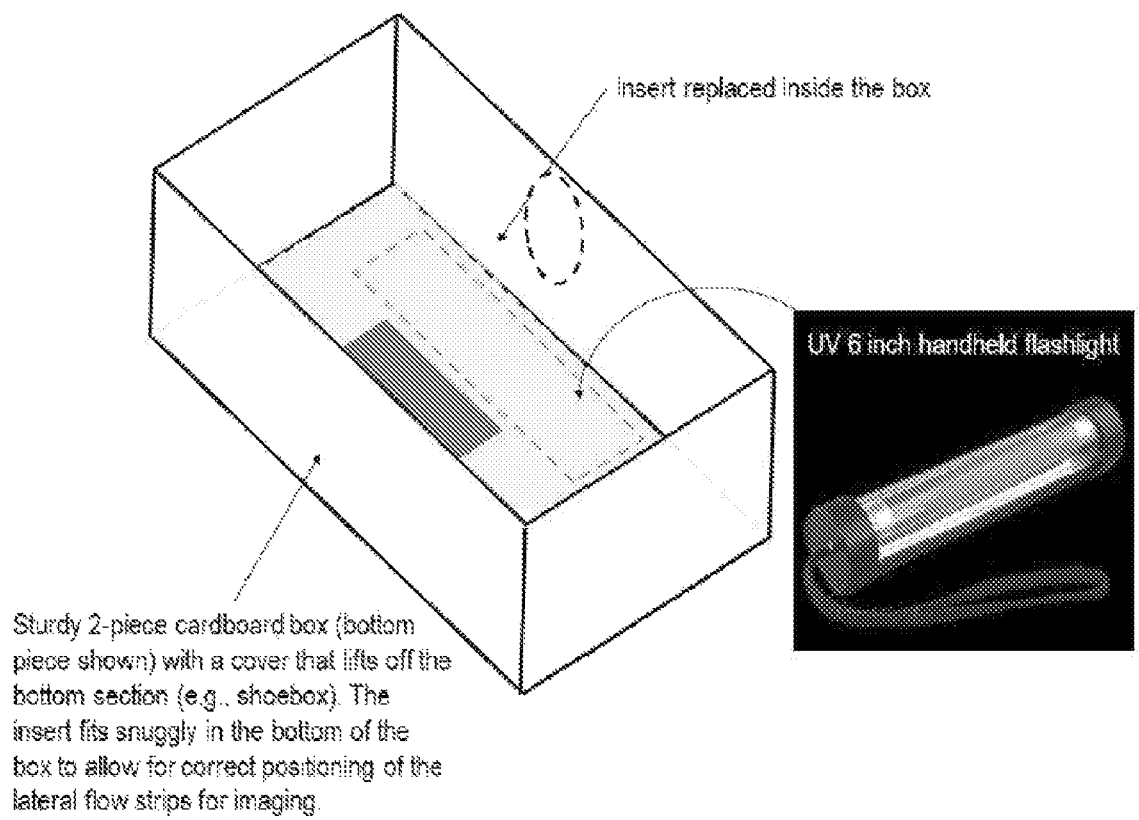
Figure 21:
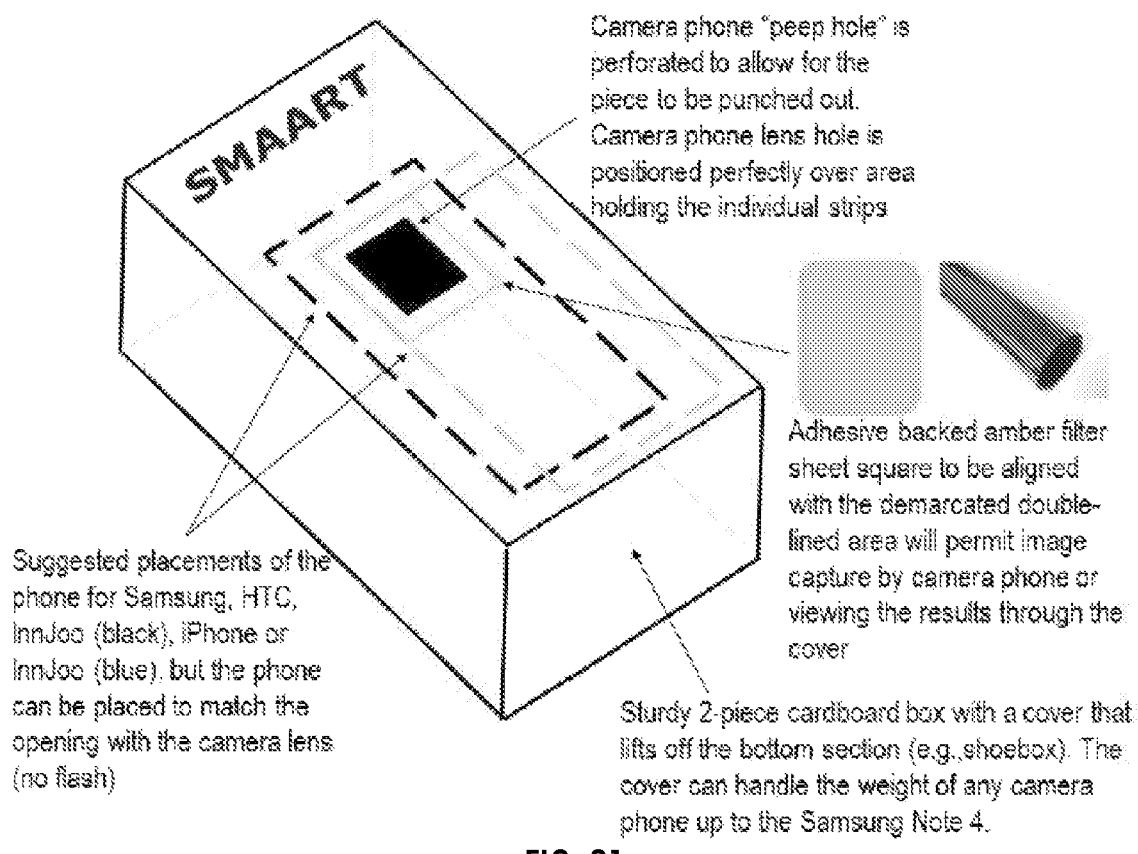

The kit can further comprise a strip holder insert (e.g., cardboard) for imaging 10 strips at a time (FIG. 18). The box containing the kit components can also serve as the viewing box for 10 strips from different individuals that are analyzed at the same time (FIGS. 19-21).

Figure 19:
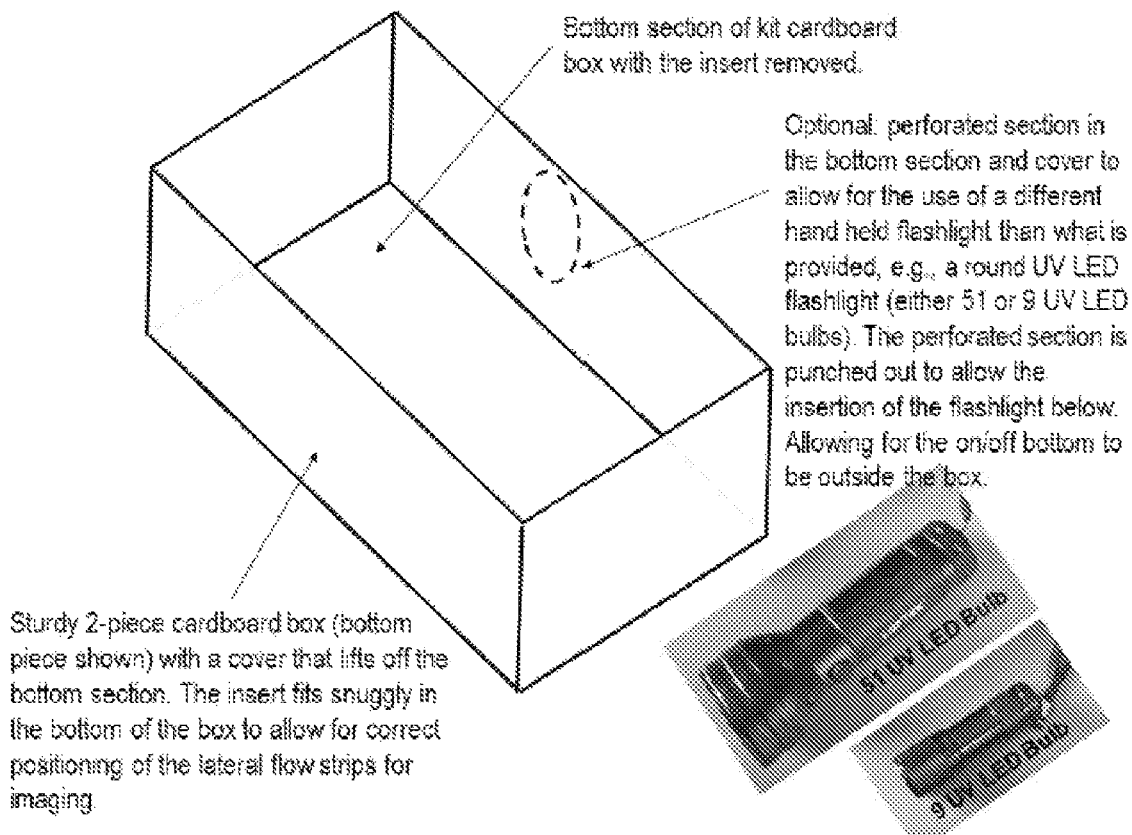
FIGS. 19-21. Cardboard kit schematic for viewing strips.

In further embodiments, a battery powered 395 nm (51W equivalent/2000 lumens) LED UV flashlight is provided (FIG. 19). For example, with the purchase of 10 kits a 395 nm 9 UV LED flashlight is provided. With the purchase of 5 kits, a battery powered 395 nm 4 W UV flashlight (including 4AA batteries and a replacement bulb) is provided (FIG. 20). An amber filter sheet sticker (Epak Electronics, Ltd. (United Kingdom)) is provided with each box to allow for camera phone image acquisition (FIG. 21). A filter is not required for visualization by eye.

Method of Detection

Lateral Flow Immunoassay
Antibody Conjugation.

Antibody immobilization procedure was adapted from previously published methods (Xiaofei Yuan et al. 2012; Etvi Juntunen et al. 2012). To activate MP carboxyl groups, 30 µL MPs in 120 µL MES buffer was combined with 15 µL EDC to achieve an EDC: COOH stoichiometric ratio of 1. The reaction was incubated for 20 min and then 125 µL borate buffer (200 mM) and 50 µL of 27C9.B5 (941 µg/mL) were added to achieve 1.354 mg Ab/M2 of MP surface area. Reaction was incubated for 1 h. MPs were then centrifuged. Supernatant was discarded and pellet was resuspended via sonication in 300 µl borate buffer (20 mM). PEG solution was added to a concentration of 0.1% (w/v) and the reactions was incubated for 30 min, centrifuged, and resuspended in borate buffer (20 mM) as before. Incubation steps were carried out at room temperature (RT) with gentle shaking, and centrifugation steps at 10,000×g for 25 min at 4° C.

Anti-PF3D7_1218800 mAb 27C9.B5 IgG was covalently coupled to carboxylate-modified polystyrene microparticles (MPs, 1% w/v) with 0.099 nm diameter, 37 A2 parking area, and Europium (III)-chelate (Thermo Fisher Scientific). 1-Ethyl-3-(3-Dimethylaminopropyl) Carbodiimide Hydrochloride (EDC, Thermo Fisher Scientific) was diluted to 10 mg/mL. Coupling reactions were performed using 200 mM and 20 mM sodium tetraborate decahydrate buffer (pH 9), as well as 25 mM MES buffer (pH 6.1). A 3% solution of Methoxypolyethylene glycol amine (PEG, Mn=5000 g/mol, Sigma Aldrich) was used for blocking MPs. Final MP-27C9.B5 conjugate (MPAb) concentration was 0.1% (w/v). Anti-PSSP17 mAb 10E2.B7 IgG (Bio-Ab) was biotinylated using EZ-Link NHS-PEO4-Biotinylation Kit (Thermo Fisher) at a 20:1 Biotin:Antibody molar ratio.

Biomarker Capture and Detection Using the LFIA Strip.

Sample Dilution Buffer (SDB50), Matrix Reduction Buffer (MRB), and gRAD OneDetection strips were provided by BioPorto (Hellerup, Denmark). Assays are carried out by combining 10 µL of MRB: SDB50 1:10,000 with either 10 µL of human saliva samples or control naïve human µL saliva spiked with recombinant PSSP17 to concentrations of 100 ng/mL to 0.5 ng/mL. To this 20 µL reaction, 1.5 µL of both MPAb (1.87E12 MP/mL) and Bio-Ab (580 µg/mL) are added with a fine tip transfer pipette and allowed to incubate for 5 min. Using the same tube, 3 drops of 120 µL SDB50 are added to the same microdilution tube as a chase buffer. The strip is then placed into the microdilution tube to draw up the strip. Once the buffer has been wicked up, the n tube/strip can be laid down on the table top, and then the strip removed from the tube and allowed to air dry for up to 5 minutes. LFIA strips are then activated by a LOFTEK® 51 UV LED handheld Flashlight 395 nM and imaged using an amber filter and an iPhone 5s 8 megapixel (MP) camera. All the UV LED hand held flashlights will work with the LFIA. However, any smart phone with a camera with ≥8 MP can be used for image acquisition. Android-based smart phones will allow for image analysis as described below. It is anticipated that working with cell phone manufacturers that a UV LED flash open can be utilized.

Data Storage, Cataloging and Quantification

Figure 22:
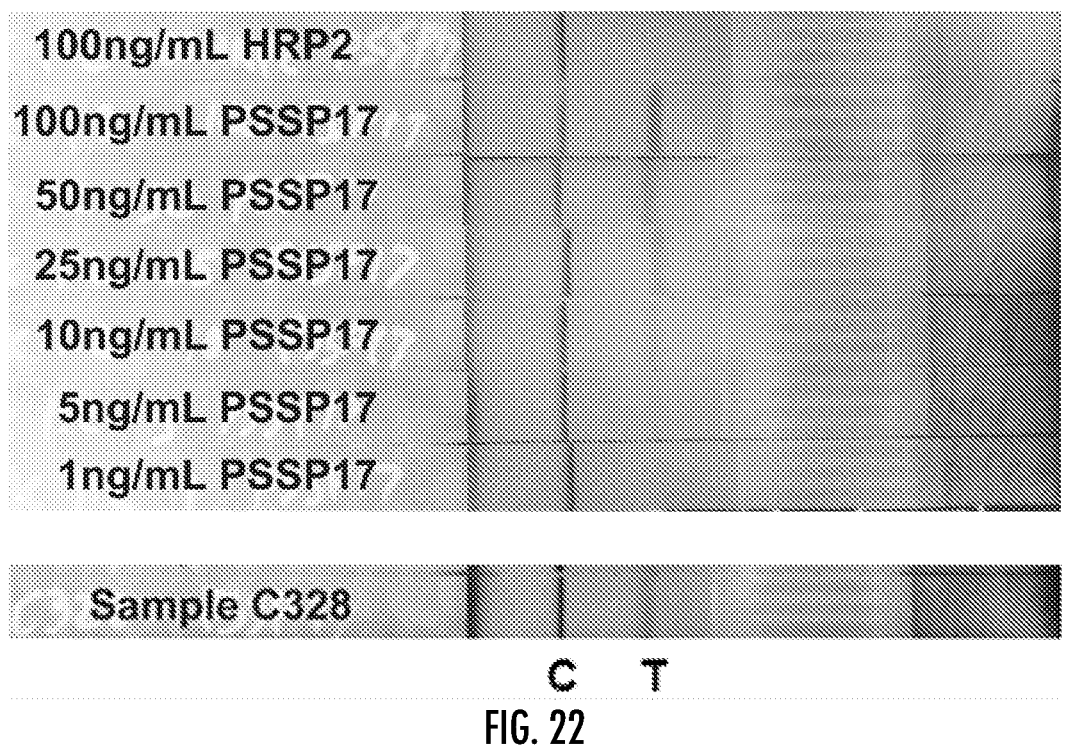
FIG. 22. Recombinant PSSP17 in known concentrations for generating standard curve.

Image acquisition by a camera phone (≥8 MP) would allow for analysis of the image in grayscale using image analysis algorithms akin to those that have been developed for MATLAB, ImageJ and "reader" software in R. The fluorescence image is first converted into grayscale and the intensity (pixel) of the Test line is compared to the Control line. Alternatively, the intensity can be compared to a stored value for intensity based on readings using a standard curve with recombinant PSSP17 in known concentrations (FIG. 22). Negative control saliva was spiked with the irrelevant *P. falciparum* HRP2 protein and analyzed with the PSSP17 lateral flow strips. Serial dilutions of recombinant PfPSSP17 were spiked into uninfected, naïve human saliva to generate a standard that allows for the measurement of pixel intensity for the test and control lines and a comparison of the ratio of test/control line for each standard. An android-based app can be developed for image analysis. For all assays, only 10 4 of spiked-saliva were analyzed. Limit of detection for the assay is ~50 pg of PSSP17. The 100 ng/mL strip takes about 4-5 mins to "develop". The 10 ng/mL strip takes about 20 mins to develop. As a positive control we used mature *P. falciparum* gametocyte lysate (estimated to be ~150 gametocytes/4). The lower limit of detection of recombinant PSSP17 was between 1-5 ng/mL, which is about 3-12 gametocytes/4. This has been verified using a real field sample from a gametocytemic child in Cameroon, wherein the limit of detection of microscopy of 16 gametocytes/µL of blood was matched by SMAART detection of PSSP17 in the saliva from the same child (C328).

Each strip can be dried and stored in the dark to further improve image acquisition and analysis up to 1 month following collection. Drying the strip for longer than 30 mins can greatly improve test control intensity for samples with lower abundance of the biomarker.

Images acquired by camera phone can be uploaded to a local ministry of health cloud data repository or a cloud drive in another country, to facilitate real-time surveillance data reporting, cataloging and analysis.

Example 5: Use of SMAART for Detection of *P. vivax* Gametocyte Carriage

*Plasmodium falciparum* PSSP17 (Pfpssp17) and its ortholog in *P. vivax* (Pvpssp17) share 80% amino acid (aa) sequence identity (FIG. 23). Importantly, the region (bar) used to raise monoclonal antibodies for detection and capture of PSSP17 from human saliva has 87% (102/117 aa) sequence identity. Signal peptide is shown as an arrow for Pfpssp17 (as determined by SignalP v. 4.1 algorithm). It is expected that the compositions and methods of the present invention can be used to detect *P. ovale, P. malariae* and *P. knowlesi*.

Figure 24:
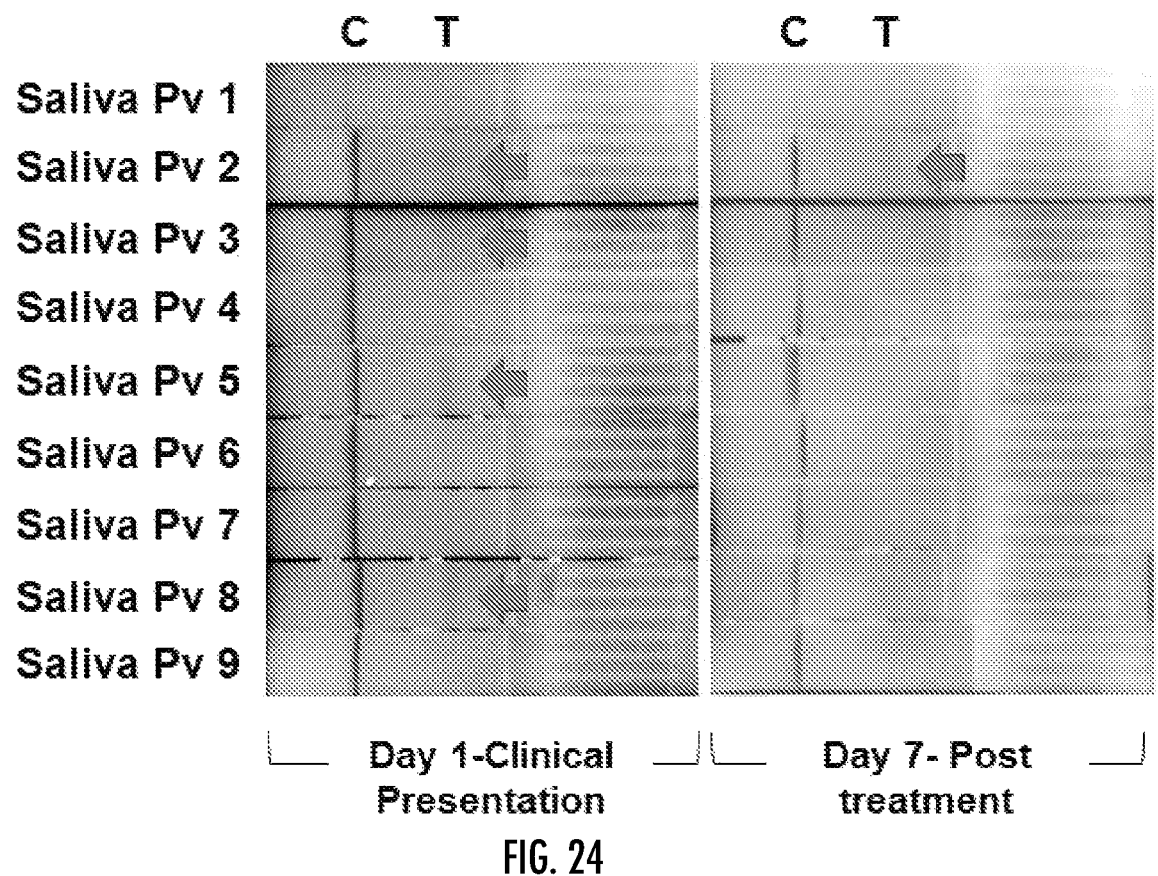
FIG. 24. SMAART lateral flow immunoassay used to detect the presence of the *P. vivax* gametocyte PSSP17 in 10 µl of unprocessed, blinded saliva from adults presenting at a clinic in Manaus, Brazil. Image was captured by camera phone and inverted. C, control line. T, test line.

The SMAART Lateral Flow Immunoassay prototype can detect the presence of the *P. vivax* gametocyte PSSP17 in 10 µl of unprocessed, blinded saliva from adults presenting at a clinic in Manaus, Brazil. See FIG. 24. Image was captured by camera phone and inverted. Of the 9 saliva samples tested, four (4) were positive (red arrows) at the test line (T). Once unblinded, the samples were found to be from individuals who are were found to be positive by microscopy for asexual blood stages of *P. vivax* upon patient intake at the clinic (Day 1, left panel). However, given the difficulty in identifying *P. vivax* gametocytes, gametocytemia was not determined for each blood smear. *P. vivax* gametocytes are present in the blood at the same time as asexual stages during the primary attack, which is quite different from *P. falciparum*. Although *P. vivax* gametocytes appear very early in infection and represent less than 2% of the total parasite biomass, they are also short-lived. Individuals presenting at a clinic with symptomatic malaria may or may have detectable gametocytes in their blood, since they would presumably be at different stages of the infection cycle. The same individuals were treated with Primaquine and re-screened at Day 7 (right panel) following treatment. The patients were all microscopy-negative following drug treatment. However, we determined that saliva from patient #2 appeared to remain faintly positive for *P. vivax* gametocytes. Whereas, saliva samples analyzed from patient #3, #5 and #8 suggest that parasite clearance was complete following drug treatment. This study demonstrates the utility of the SMAART test to determine parasite clearance after drug treatment, specifically for stages that are responsible for transmission to mosquitoes.

We claim:

1. An antibody or fragment thereof that specifically binds SEQ ID NO:8, wherein the antibody comprises (a) a variable heavy chain comprising SEQ ID NO:20; and (b) a variable light chain comprising SEQ ID NO:40.

2. An antibody or fragment thereof that specifically binds SEQ ID NO:8, wherein the antibody comprises (a) a variable heavy chain comprising SEQ ID NO:60; and (b) a variable light chain comprising SEQ ID NO:80.

3. An antibody comprising (a) a variable heavy chain comprising the complementarity determining regions (CDRs) shown in SEQ ID NOS:23, 25 and 27; and (b) a variable light chain comprising the CDRs shown in SEQ ID NOS:43, 45 and 47, wherein the antibody specifically binds SEQ ID NO:8 or PSSPI7.

4. An antibody comprising (a) a variable heavy chain comprising the CDRs shown in SEQ ID NOS:63, 65 and 67; and (b) a variable light chain comprising the CDRs shown in SEQ ID NOS:83, 85 and 87, wherein the antibody specifically binds SEQ ID NO:8 or PSSP17.

5. A kit comprising (a) at least one antibody that specifically binds PSSPI7; and (b) a detection reagent for detecting the presence of PSSPI 7 in a saliva sample obtained from a subject suspected of having a malaria parasite, wherein the at least one antibody that specifically binds PSSPI 7 comprises an antibody that specifically binds SEQ ID NO:8, wherein, the at least one antibody comprises:
   i. (a) a variable heavy chain comprising SEO ID NO:20; and (b) a variable light chain comprising SEO ID NO:40; or,
   ii. (a) a variable heavy chain comprising SEO ID NO:60; and (b) a variable light chain comprising SEO ID NO:80; or
   iii. (a) a variable heavy chain comprising the complementarity determining regions (CDRs) shown in SEO ID NOS:23, 25 and 27; and (b) a variable light chain comprising the CDRs shown in SEO ID NOS:43, 45 and 47; or,
   iv. (a) a variable heavy chain comprising the CDRs shown in SEO ID NOS:63, 65 and 67; and (b) a variable light chain comprising the CDRs shown in SEO ID NOS:83, 85 and 87.

6. The kit of claim 5, further comprising (c) at least one antibody hat specifically binds histidine rich protein 2 (HRP2) of *Plasmodium falciparum*; and (d) a detection reagent for detecting the presence of the HRP2 in a saliva sample obtained from a subject suspected of having a malaria parasite.

7. The kit of claim 5, further comprising a lateral flow immunoassay device.

8. The kit of claim 5, further comprising a positive control for PSSP17, wherein the positive control is the amino acid sequence shown in SEQ ID NO:8.

9. A rapid diagnostic test kit for the malaria parasite *Plasmodium* comprising:
   a. a plurality of capture reagents, wherein the plurality of capture reagents comprise antibodies comprising:
      i. (a) a variable heavy chain comprising SEQ ID NO: 20; and (b) a variable light chain comprising SEQ ID NO: 40; or
      ii. (a) a variable heavy chain comprising SEQ ID NO: 60; and (b) a variable light chain comprising SEQ ID NO: 80; or
      iii. (a) a variable heavy chain comprising the complementarity determining regions (CDRs) shown in SEQ ID NOS: 23, 25 and 27; and (b) a variable light chain comprising the CDRs shown in SEQ ID NOS: 53, 45 and 47; or
      iv. (a) a variable heavy chain comprising the complementarity determining regions (CDRs) shown in SEQ ID NOS: 63, 65 and 67; and (b) a variable light chain comprising the CDRs shown in SEQ ID NOS: 83, 85 and 87;
   b. a detection agent that binds to the capture reagents;
   c. instructions for collecting a sample from the individual, incubating the plurality of capture reagents, detecting the presence of the capture reagents bound to the proteins;
   wherein he capture reagents are antibodies.

10. The kit of claim 9, wherein the one or more proteins are encoded by the gene comprises identified by accession number PF3D7 1218800 (PSSPI7).

11. The kit of claim 10, wherein the one or more proteins are encoded by the gene further comprises identified by accession number PF3D7_0507800.

12. The kit of claim 9, wherein the kit further comprises an antibody that binds to histidine rich protein 2 (HRP2) of *Plasmodium falciparum*.

13. The kit of claim 9, further comprising a positive control protein comprising SEQ ID NO: 8.

* * * * *

SEQUENCE LISTING

<160> NUMBER OF SEQ ID NOS: 90

<210> SEQ ID NO 1
<211> LENGTH: 22
<212> TYPE: DNA
<213> ORGANISM: Artificial Sequence
<220> FEATURE:
<223> OTHER INFORMATION: PF3D7_0906100 forward primer

<400> SEQUENCE: 1
caccatgggt aacaaaatta gc                                              22

<210> SEQ ID NO 2
<211> LENGTH: 22
<212> TYPE: PRT
<213> ORGANISM: Artificial Sequence
<220> FEATURE:
<223> OTHER INFORMATION: PF3D7_0906100 reverse primer

<400> SEQUENCE: 2

Thr Thr Thr Cys Ala Gly Gly Thr Thr Thr Thr Gly Ala Thr Ala
1               5                   10                  15

Cys Gly Thr Thr Cys Cys
            20

<210> SEQ ID NO 3
<211> LENGTH: 20
<212> TYPE: DNA
<213> ORGANISM: Artificial Sequence
<220> FEATURE:
<223> OTHER INFORMATION: PF3D7_1218800 forward primer

<400> SEQUENCE: 3
caccaaaatc gtgctgtcca                                          20

<210> SEQ ID NO 4
<211> LENGTH: 24
<212> TYPE: DNA
<213> ORGANISM: Artificial Sequence
<220> FEATURE:
<223> OTHER INFORMATION: PF3D7_1218800 reverse primer

<400> SEQUENCE: 4
accgaagtaa ataaaactcg gttc                                     24

<210> SEQ ID NO 5
<211> LENGTH: 18
<212> TYPE: DNA
<213> ORGANISM: Artificial Sequence
<220> FEATURE:
<223> OTHER INFORMATION: PF3D7_0309100 forward primer

<400> SEQUENCE: 5
caccgacctg agcggcct                                            18

<210> SEQ ID NO 6
<211> LENGTH: 25
<212> TYPE: DNA
<213> ORGANISM: Artificial Sequence
<220> FEATURE:
<223> OTHER INFORMATION: PF3D7_0309100 reverse primer

<400> SEQUENCE: 6
cagttcttcg tttttgatga acacg                                    25

<210> SEQ ID NO 7
<211> LENGTH: 351
<212> TYPE: DNA
<213> ORGANISM: Plasmodium falciparum

<400> SEQUENCE: 7
aaaatcgtgc tgtccaccct cgtcgtccacc aactcggcgg gcgaagaatt cctgtccaac    60
ttcaaactgc gtcatcatca atggtatcat atgaccgtgg ttcgtcatat caaccacgtc   120
cgcctgtttg tggatggcat tctggacagc tctttcctga cggaaggtat caccaaaacg   180
aatgatagcc cgatttatat cggcggtgcg ccgtactcgg ttgatagctg cgactttccg   240
ttcctgctgg atgaactgaa aatttataac ctgtctatcg caccgacca gattcaatcc   300 gaagcgagtg cctccctgtc aggcatcgaa ccgagtttta tttacttcgg t            351

<210> SEQ ID NO 8

```
<211> LENGTH: 117
<212> TYPE: PRT
<213> ORGANISM: Plasmodium falciparum

<400> SEQUENCE: 8
```

Lys Ile Val Leu Ser Thr Ser Ser Thr Asn Ser Ala Gly Glu Glu
 1               5                  10                  15

Phe Leu Ser Asn Phe Lys Leu Arg His His Gln Trp Tyr His Met Thr
            20                  25                  30

Val Val Arg His Ile Asn His Val Arg Leu Phe Val Asp Gly Ile Leu
        35                  40                  45

Asp Ser Ser Phe Leu Thr Glu Gly Ile Thr Lys Thr Asn Asp Ser Pro
    50                  55                  60

Ile Tyr Ile Gly Gly Ala Pro Tyr Ser Val Asp Ser Cys Asp Phe Pro
65                  70                  75                  80

Phe Leu Leu Asp Glu Leu Lys Ile Tyr Asn Leu Ser Ile Gly Thr Asp
                85                  90                  95

Gln Ile Gln Ser Glu Ala Ser Ala Ser Leu Ser Gly Ile Glu Pro Ser
            100                 105                 110

Phe Ile Tyr Phe Gly
        115

```
<210> SEQ ID NO 9
<211> LENGTH: 408
<212> TYPE: DNA
<213> ORGANISM: Artificial Sequence
<220> FEATURE:
<223> OTHER INFORMATION: mAb 10E2B7 heavy chain (+leader sequence)

<400> SEQUENCE: 9
atgaacttcg ggctcagctt gattttcctt gccctcattt taaaaggtgt ccagtgtgag      60
gtgcagctgg tggagtctgg gggagactta gtgaagcctg agggtccct gaaactctcc     120
tgtgcagcct ctggattcac tttcagttcc tatggcatgt cttgggttcg ccagactcca     180
gacaagagac tggagtgggt cgcaaccatt agtagtggtg gtagttacat ttactatcca     240
gacagtatga gggggcgatt caccatgtcc agagacaatg ccaagaacac cctgtacctg     300
caaatgagca gtctgaagtc tgaggacaca gccatgtatt actgtgcaag agaggaaagg     360
gattggttag cttactgggg ccaagggact ctggtcactg tctctgca                   408

<210> SEQ ID NO 10
<211> LENGTH: 351
<212> TYPE: DNA
<213> ORGANISM: Artificial Sequence
<220> FEATURE:
<223> OTHER INFORMATION: mAb 10E2B7 heavy chain (-leader sequence)

<400> SEQUENCE: 10
gaggtgcagc tggtggagtc tgggggagac ttagtgaagc tggagggtc cctgaaactc       60
tcctgtgcag cctctggatt cactttcagt tcctatggca tgtcttgggt tcgccagact     120
ccagacaaga gactggagtg ggtcgcaacc attagtagtg gtggtagtta catttactat     180
ccagacagta tgaaggggcg attcaccatg tccagagaca atgccaagaa caccctgtac     240
ctgcaaatga gcagtctgaa gtctgaggac acagccatgt attactgtgc aagagaggaa     300
agggattggt tagcttactg gggccaaggg actctggtca ctgtctctgc a               351

<210> SEQ ID NO 11
<211> LENGTH: 57
```

```
<212> TYPE: DNA
<213> ORGANISM: Artificial Sequence
<220> FEATURE:
<223> OTHER INFORMATION: mAb 10E2B7 heavy chain leader sequence

<400> SEQUENCE: 11
atgaacttcg ggctcagctt gattttcctt gccctcattt taaaaggtgt ccagtgt          57

<210> SEQ ID NO 12
<211> LENGTH: 90
<212> TYPE: DNA
<213> ORGANISM: Artificial Sequence
<220> FEATURE:
<223> OTHER INFORMATION: mAb 10E2B7 heavy chain framework region 1

<400> SEQUENCE: 12
gaggtgcagc tggtggagtc tgggggagac ttagtgaagc tggagggtc cctgaaactc         60 tcctgtgcag cctctggatt cactttcagt                                         90

<210> SEQ ID NO 13
<211> LENGTH: 15
<212> TYPE: DNA
<213> ORGANISM: Artificial Sequence
<220> FEATURE:
<223> OTHER INFORMATION: mAb 10E2B7 heavy chain CDR1

<400> SEQUENCE: 13
tcctatggca tgtct                                                         15

<210> SEQ ID NO 14
<211> LENGTH: 42
<212> TYPE: DNA
<213> ORGANISM: Artificial Sequence
<220> FEATURE:
<223> OTHER INFORMATION: mAb 10E2B7 heavy chain framework region 2

<400> SEQUENCE: 14
tgggttcgcc agactccaga caagagactg gagtgggtcg ca                           42

<210> SEQ ID NO 15
<211> LENGTH: 51
<212> TYPE: DNA
<213> ORGANISM: Artificial Sequence
<220> FEATURE:
<223> OTHER INFORMATION: mAb 10E2B7 heavy chain CDR2

<400> SEQUENCE: 15
accattagta gtggtggtag ttacatttac tatccagaca gtatgaaggg g                 51

<210> SEQ ID NO 16
<211> LENGTH: 96
<212> TYPE: DNA
<213> ORGANISM: Artificial Sequence
<220> FEATURE:
<223> OTHER INFORMATION: mAb 10E2B7 heavy chain framework region 3

<400> SEQUENCE: 16
cgattcacca tgtccagaga caatgccaag aacaccctgt acctgcaaat gagcagtctg        60
aagtctgagg acacagccat gtattactgt gcaaga                                  96

<210> SEQ ID NO 17
<211> LENGTH: 24
<212> TYPE: DNA
<213> ORGANISM: Artificial Sequence
<220> FEATURE:
```

-continued

<223> OTHER INFORMATION: mAb 10E2B7 heavy chain CDR3

<400> SEQUENCE: 17
gaggaaaggg attggttagc ttac                                            24

<210> SEQ ID NO 18
<211> LENGTH: 33
<212> TYPE: DNA
<213> ORGANISM: Artificial Sequence
<220> FEATURE:
<223> OTHER INFORMATION: mAb 10E2B7 heavy chain framework region 4

<400> SEQUENCE: 18
tggggccaag ggactctggt cactgtctct gca                                  33

<210> SEQ ID NO 19
<211> LENGTH: 136
<212> TYPE: PRT
<213> ORGANISM: Artificial Sequence
<220> FEATURE:
<223> OTHER INFORMATION: mAb 10E2B7 heavy chain (+leader sequence)

<400> SEQUENCE: 19

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Asp Ser Met Lys Gly Arg Phe Thr Met Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Glu Glu Arg Asp Trp Leu Ala Tyr Trp Gly Gln
        115                 120                 125

Gly Thr Leu Val Thr Val Ser Ala
    130                 135

<210> SEQ ID NO 20
<211> LENGTH: 117
<212> TYPE: PRT
<213> ORGANISM: Artificial Sequence
<220> FEATURE:
<223> OTHER INFORMATION: mAb 10E2B7 heavy chain (-leader sequence)

<400> SEQUENCE: 20

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Ile Tyr Tyr Pro Asp Ser Met
    50                  55                  60

Lys Gly Arg Phe Thr Met Ser Arg Asp Asn Ala Lys Asn Thr Leu Tyr
65                  70                  75                  80

```
Leu Gln Met Ser Ser Leu Lys Ser Glu Asp Thr Ala Met Tyr Tyr Cys
                85                  90                  95

Ala Arg Glu Glu Arg Asp Trp Leu Ala Tyr Trp Gly Gln Gly Thr Leu
            100                 105                 110

Val Thr Val Ser Ala
        115

<210> SEQ ID NO 21
<211> LENGTH: 19
<212> TYPE: PRT
<213> ORGANISM: Artificial Sequence
<220> FEATURE:
<223> OTHER INFORMATION: mAb 10E2B7 heavy chain leader sequence

<400> SEQUENCE: 21

Met Asn Phe Gly Leu Ser Leu Ile Phe Leu Ala Leu Ile Leu Lys Gly
1               5                   10                  15

Val Gln Cys

<210> SEQ ID NO 22
<211> LENGTH: 30
<212> TYPE: PRT
<213> ORGANISM: Artificial Sequence
<220> FEATURE:
<223> OTHER INFORMATION: mAb 10E2B7 heavy chain framework region 1

<400> SEQUENCE: 22

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 23
<211> LENGTH: 5
<212> TYPE: PRT
<213> ORGANISM: Artificial Sequence
<220> FEATURE:
<223> OTHER INFORMATION: mAb 10E2B7 heavy chain CDR1

<400> SEQUENCE: 23

Ser Tyr Gly Met Ser
1               5

<210> SEQ ID NO 24
<211> LENGTH: 14
<212> TYPE: PRT
<213> ORGANISM: Artificial Sequence
<220> FEATURE:
<223> OTHER INFORMATION: mAb 10E2B7 heavy chain framework region 2

<400> SEQUENCE: 24

Trp Val Arg Gln Thr Pro Asp Lys Arg Leu Glu Trp Val Ala
1               5                   10

<210> SEQ ID NO 25
<211> LENGTH: 17
<212> TYPE: PRT
<213> ORGANISM: Artificial Sequence
<220> FEATURE:
<223> OTHER INFORMATION: mAb 10E2B7 heavy chain CDR2

<400> SEQUENCE: 25

Thr Ile Ser Ser Gly Gly Ser Tyr Ile Tyr Tyr Pro Asp Ser Met Lys
1               5                   10                  15
```

Gly

<210> SEQ ID NO 26
<211> LENGTH: 32
<212> TYPE: PRT
<213> ORGANISM: Artificial Sequence
<220> FEATURE:
<223> OTHER INFORMATION: mAb 10E2B7 heavy chain framework region 3

<400> SEQUENCE: 26

Arg Phe Thr Met Ser Arg Asp Asn Ala Lys Asn Thr Leu Tyr Leu Gln
1               5                   10                  15

Met Ser Ser Leu Lys Ser Glu Asp Thr Ala Met Tyr Tyr Cys Ala Arg
            20                  25                  30

<210> SEQ ID NO 27
<211> LENGTH: 8
<212> TYPE: PRT
<213> ORGANISM: Artificial Sequence
<220> FEATURE:
<223> OTHER INFORMATION: mAb 10E2B7 heavy chain CDR3

<400> SEQUENCE: 27

Glu Glu Arg Asp Trp Leu Ala Tyr
1               5

<210> SEQ ID NO 28
<211> LENGTH: 11
<212> TYPE: PRT
<213> ORGANISM: Artificial Sequence
<220> FEATURE:
<223> OTHER INFORMATION: mAb 10E2B7 heavy chain framework region 4

<400> SEQUENCE: 28

Trp Gly Gln Gly Thr Leu Val Thr Val Ser Ala
1               5                   10

<210> SEQ ID NO 29
<211> LENGTH: 393
<212> TYPE: DNA
<213> ORGANISM: Artificial Sequence
<220> FEATURE:
<223> OTHER INFORMATION: mAb 10E2B7 DNA light chain (+leader sequence)

<400> SEQUENCE: 29
atgaagttgc ctgttaggct gttggtgctg atgttctgga ttcctgcttc cagcagtgat      60
gttgtgatga cccaaagtcc actctccctg cctgtcagtc ttggagatca agcctccatc     120
tcttgcagat ctagtcagag ccttatacac aataatggag acatctatgt acattggtac     180
ctgcagaagc caggccagtc tccaaagctc ctgatctaca agtttccaa ccgattttct      240 ggggtcccag acaggttcag tggcagtgga tcaggacag atttcacatt caagatcagc      300
agagtggagg ctgaggatct gggagtttat ttctgctctc aaagttcaca tgttcctccc     360
acgttcggag ggggaccaa gctggaaata aaa                                    393

<210> SEQ ID NO 30
<211> LENGTH: 336
<212> TYPE: DNA
<213> ORGANISM: Artificial Sequence
<220> FEATURE:
<223> OTHER INFORMATION: mAb 10E2B7 DNA light chain (-leader sequence)

<400> SEQUENCE: 30
gatgttgtga tgacccaaag tccactctcc ctgcctgtca gtcttggaga tcaagcctcc    60
atctcttgca gatctagtca gagccttata cacaataatg gagacatcta tgtacattgg   120
tacctgcaga agccaggcca gtctccaaag ctcctgatct acaaagtttc caaccgattt   180
tctggggtcc cagacaggtt cagtggcagt ggatcaggga cagatttcac attcaagatc   240
agcagagtgg aggctgagga tctgggagtt tatttctgct ctcaaagttc acatgttcct   300
cccacgttcg gagggggac caagctggaa ataaaa                              336

<210> SEQ ID NO 31
<211> LENGTH: 57
<212> TYPE: DNA
<213> ORGANISM: Artificial Sequence
<220> FEATURE:
<223> OTHER INFORMATION: mAb 10E2B7 DNA light chain leader sequence

<400> SEQUENCE: 31
atgaagttgc ctgttaggct gttggtgctg atgttctgga ttcctgcttc cagcagt       57

<210> SEQ ID NO 32
<211> LENGTH: 69
<212> TYPE: DNA
<213> ORGANISM: Artificial Sequence
<220> FEATURE:
<223> OTHER INFORMATION: mAb 10E2B7 DNA light chain framework region 1

<400> SEQUENCE: 32
gatgttgtga tgacccaaag tccactctcc ctgcctgtca gtcttggaga tcaagcctcc    60
atctcttgc                                                            69

<210> SEQ ID NO 33
<211> LENGTH: 48
<212> TYPE: DNA
<213> ORGANISM: Artificial Sequence
<220> FEATURE:
<223> OTHER INFORMATION: mAb 10E2B7 DNA light chain CDR1

<400> SEQUENCE: 33
agatctagtc agagccttat acacaataat ggagacatct atgtacat                 48

<210> SEQ ID NO 34
<211> LENGTH: 45
<212> TYPE: DNA
<213> ORGANISM: Artificial Sequence
<220> FEATURE:
<223> OTHER INFORMATION: mAb 10E2B7 DNA light chain framework region 2

<400> SEQUENCE: 34
tggtacctgc agaagccagg ccagtctcca aagctcctga tctac                    45

<210> SEQ ID NO 35
<211> LENGTH: 21
<212> TYPE: DNA
<213> ORGANISM: Artificial Sequence
<220> FEATURE:
<223> OTHER INFORMATION: mAb 10E2B7 DNA light chain CDR2

<400> SEQUENCE: 35
aaagtttcca accgattttc t                                              21

<210> SEQ ID NO 36
<211> LENGTH: 96
<212> TYPE: DNA
<213> ORGANISM: Artificial Sequence

```
<220> FEATURE:
<223> OTHER INFORMATION: mAb 10E2B7 DNA light chain framework region 3

<400> SEQUENCE: 36
ggggtcccag acaggttcag tggcagtgga tcagggacag atttcacatt caagatcagc      60
agagtggagg ctgaggatct gggagtttat ttctgc                                96

<210> SEQ ID NO 37
<211> LENGTH: 27
<212> TYPE: DNA
<213> ORGANISM: Artificial Sequence
<220> FEATURE:
<223> OTHER INFORMATION: mAb 10E2B7 DNA light chain CDR3

<400> SEQUENCE: 37
tctcaaagtt cacatgttcc tcccacg                                          27

<210> SEQ ID NO 38
<211> LENGTH: 30
<212> TYPE: DNA
<213> ORGANISM: Artificial Sequence
<220> FEATURE:
<223> OTHER INFORMATION: mAb 10E2B7 DNA light chain framework region 4

<400> SEQUENCE: 38
ttcggagggg ggaccaagct ggaaataaaa                                       30

<210> SEQ ID NO 39
<211> LENGTH: 131
<212> TYPE: PRT
<213> ORGANISM: Artificial Sequence
<220> FEATURE:
<223> OTHER INFORMATION: mAb 10E2B7 AA light chain (+leader sequence)

<400> SEQUENCE: 39

Met Lys Leu Pro Val Arg Leu Leu Val Leu Met Phe Trp Ile Pro Ala
1               5                   10                  15

Ser Ser Ser Asp Val Val Met Thr Gln Ser Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Asn Asn Gly Asp Ile Tyr Val His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Phe Lys Ile Ser Arg Val Glu Ala Glu Asp Leu Gly Val Tyr Phe Cys
            100                 105                 110

Ser Gln Ser Ser His Val Pro Pro Thr Phe Gly Gly Gly Thr Lys Leu
        115                 120                 125

Glu Ile Lys
    130

<210> SEQ ID NO 40
<211> LENGTH: 112
<212> TYPE: PRT
<213> ORGANISM: Artificial Sequence
<220> FEATURE:
<223> OTHER INFORMATION: mAb 10E2B7 AA light chain (-leader sequence)

<400> SEQUENCE: 40
```

```
Asp Val Val Met Thr Gln Ser Pro Leu Ser Leu Pro Val Ser Leu Gly
1               5                   10                  15

Asp Gln Ala Ser Ile Ser Cys Arg Ser Gln Ser Leu Ile His Asn
            20                  25                  30

Asn Gly Asp Ile Tyr Val His Trp Tyr Leu Gln Lys Pro Gly Gln Ser
            35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Phe Lys Ile
65                  70                  75                  80

Ser Arg Val Glu Ala Glu Asp Leu Gly Val Tyr Phe Cys Ser Gln Ser
                85                  90                  95

Ser His Val Pro Pro Thr Phe Gly Gly Gly Thr Lys Leu Glu Ile Lys
            100                 105                 110

<210> SEQ ID NO 41
<211> LENGTH: 19
<212> TYPE: PRT
<213> ORGANISM: Artificial Sequence
<220> FEATURE:
<223> OTHER INFORMATION: mAb 10E2B7 AA light chain leader sequence

<400> SEQUENCE: 41

Met Lys Leu Pro Val Arg Leu Leu Val Leu Met Phe Trp Ile Pro Ala
1               5                   10                  15

Ser Ser Ser

<210> SEQ ID NO 42
<211> LENGTH: 23
<212> TYPE: PRT
<213> ORGANISM: Artificial Sequence
<220> FEATURE:
<223> OTHER INFORMATION: mAb 10E2B7 AA light chain framework region 1

<400> SEQUENCE: 42

Asp Val Val Met Thr Gln Ser Pro Leu Ser Leu Pro Val Ser Leu Gly
1               5                   10                  15

Asp Gln Ala Ser Ile Ser Cys
            20

<210> SEQ ID NO 43
<211> LENGTH: 16
<212> TYPE: PRT
<213> ORGANISM: Artificial Sequence
<220> FEATURE:
<223> OTHER INFORMATION: mAb 10E2B7 AA light chain CDR1

<400> SEQUENCE: 43

Arg Ser Ser Gln Ser Leu Ile His Asn Asn Gly Asp Ile Tyr Val His
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: mAb 10E2B7 AA light chain framework region 2

<400> SEQUENCE: 44

Trp Tyr Leu Gln Lys Pro Gly Gln Ser Pro Lys Leu Leu Ile Tyr
1               5                   10                  15
```

<210> SEQ ID NO 45
<211> LENGTH: 7
<212> TYPE: PRT
<213> ORGANISM: Artificial Sequence
<220> FEATURE:
<223> OTHER INFORMATION: mAb 10E2B7 AA light chain CDR2

<400> SEQUENCE: 45

Lys Val Ser Asn Arg Phe Ser
1               5

<210> SEQ ID NO 46
<211> LENGTH: 32
<212> TYPE: PRT
<213> ORGANISM: Artificial Sequence
<220> FEATURE:
<223> OTHER INFORMATION: mAb 10E2B7 AA light chain framework region 3

<400> SEQUENCE: 46

Gly Val Pro Asp Arg Phe Ser Gly Ser Gly Ser Gly Thr Asp Phe Thr
1               5                   10                  15

Phe Lys Ile Ser Arg Val Glu Ala Glu Asp Leu Gly Val Tyr Phe Cys
            20                  25                  30

<210> SEQ ID NO 47
<211> LENGTH: 9
<212> TYPE: PRT
<213> ORGANISM: Artificial Sequence
<220> FEATURE:
<223> OTHER INFORMATION: mAb 10E2B7 AA light chain CDR3

<400> SEQUENCE: 47

Ser Gln Ser Ser His Val Pro Pro Thr
1               5

<210> SEQ ID NO 48
<211> LENGTH: 10
<212> TYPE: PRT
<213> ORGANISM: Artificial Sequence
<220> FEATURE:
<223> OTHER INFORMATION: mAb 10E2B7 AA light chain framework region 4

<400> SEQUENCE: 48

Phe Gly Gly Gly Thr Lys Leu Glu Ile Lys
1               5                   10

<210> SEQ ID NO 49
<211> LENGTH: 411
<212> TYPE: DNA
<213> ORGANISM: Artificial Sequence
<220> FEATURE:
<223> OTHER INFORMATION: mAb 27C9B5 DNA heavy chain (+leader sequence)

<400> SEQUENCE: 49
atgggatgga gcggagtctt tatctttctc ctgtcagtaa ctgcaggtgt tcactcccag      60
gtccaggtgc ggcagtctgg agctgaagtg gtaaggcctg ggacttcagt gagggtgtcc     120
tgcaagactt ctggatacgc cttcactgat tatttgatag agtgggtcaa acagaggcct     180
ggacagggcc ttgagtggat tggagtgatt aatcctgtaa aggtactac taactacagt     240 gagaagttca aggcaaggc aacactgact gcagacaaat cctccggcac tgcctacatg     300
cagttctaca gcctgacatc tgatgactct gcggtctatt tctgtgcaag atcgagaggt     360
agtgatgggt ttccttactg gggccaaggg actctggtca ctgtctctgc a             411

<210> SEQ ID NO 50
<211> LENGTH: 354
<212> TYPE: DNA
<213> ORGANISM: Artificial Sequence
<220> FEATURE:
<223> OTHER INFORMATION: mAb 27C9B5 DNA heavy chain (-leader sequence)

<400> SEQUENCE: 50

```
caggtccagg tgcggcagtc tggagctgaa gtggtaaggc ctgggacttc agtgagggtg      60
tcctgcaaga cttctggata cgccttcact gattatttga tagagtgggt caaacagagg     120
cctggacagg gccttgagtg gattggagtg attaatcctg taagaggtac tactaactac     180
agtgagaagt tcaagggcaa ggcaacactg actgcagaca atcctccgg cactgcctac      240
atgcagttct acagcctgac atctgatgac tctgcggtct atttctgtgc aagatcgaga     300
ggtagtgatg ggtttcctta ctggggccaa gggactctgg tcactgtctc tgca           354
```

<210> SEQ ID NO 51
<211> LENGTH: 57
<212> TYPE: DNA
<213> ORGANISM: Artificial Sequence
<220> FEATURE:
<223> OTHER INFORMATION: mAb 27C9B5 DNA heavy chain leader sequence

<400> SEQUENCE: 51

```
atgggatgga gcggagtctt tatctttctc ctgtcagtaa ctgcaggtgt tcactcc         57
```

<210> SEQ ID NO 52
<211> LENGTH: 90
<212> TYPE: DNA
<213> ORGANISM: Artificial Sequence
<220> FEATURE:
<223> OTHER INFORMATION: mAb 27C9B5 DNA heavy chain framework region 1

<400> SEQUENCE: 52

```
caggtccagg tgcggcagtc tggagctgaa gtggtaaggc ctgggacttc agtgagggtg      60
tcctgcaaga cttctggata cgccttcact                                       90
```

<210> SEQ ID NO 53
<211> LENGTH: 15
<212> TYPE: DNA
<213> ORGANISM: Artificial Sequence
<220> FEATURE:
<223> OTHER INFORMATION: mAb 27C9B5 DNA heavy chain CDR1

<400> SEQUENCE: 53

```
gattatttga tagag                                                       15
```

<210> SEQ ID NO 54
<211> LENGTH: 42
<212> TYPE: DNA
<213> ORGANISM: Artificial Sequence
<220> FEATURE:
<223> OTHER INFORMATION: mAb 27C9B5 DNA heavy chain framework region 2

<400> SEQUENCE: 54

```
tgggtcaaac agaggcctgg acagggcctt gagtggattg ga                         42
```

<210> SEQ ID NO 55
<211> LENGTH: 51
<212> TYPE: DNA
<213> ORGANISM: Artificial Sequence
<220> FEATURE:
<223> OTHER INFORMATION: mAb 27C9B5 DNA heavy chain CDR2

<400> SEQUENCE: 55
gtgattaatc ctgtaagagg tactactaac tacagtgaga agttcaaggg c    51

<210> SEQ ID NO 56
<211> LENGTH: 96
<212> TYPE: DNA
<213> ORGANISM: Artificial Sequence
<220> FEATURE:
<223> OTHER INFORMATION: mAb 27C9B5 DNA heavy chain framework region 3

<400> SEQUENCE: 56
aaggcaacac tgactgcaga caaatcctcc ggcactgcct acatgcagtt ctacagcctg    60
acatctgatg actctgcggt ctatttctgt gcaaga    96

<210> SEQ ID NO 57
<211> LENGTH: 27
<212> TYPE: DNA
<213> ORGANISM: Artificial Sequence
<220> FEATURE:
<223> OTHER INFORMATION: mAb 27C9B5 DNA heavy chain CDR3

<400> SEQUENCE: 57
tcgagaggta gtgatgggtt tccttac    27

<210> SEQ ID NO 58
<211> LENGTH: 33
<212> TYPE: DNA
<213> ORGANISM: Artificial Sequence
<220> FEATURE:
<223> OTHER INFORMATION: mAb 27C9B5 DNA heavy chain framework region 4

<400> SEQUENCE: 58
tggggccaag ggactctggt cactgtctct gca    33

<210> SEQ ID NO 59
<211> LENGTH: 137
<212> TYPE: PRT
<213> ORGANISM: Artificial Sequence
<220> FEATURE:
<223> OTHER INFORMATION: mAb 27C9B5 AA heavy chain (+leader sequence)

<400> SEQUENCE: 59

Met Gly Trp Ser Gly Val Phe Ile Phe Leu Leu Ser Val Thr Ala Gly
1               5                   10                  15

Val His Ser Gln Val Gln Val Arg Gln Ser Gly Ala Glu Val Val Arg
            20                  25                  30

Pro Gly Thr Ser Val Arg Val Ser Cys Lys Thr Ser Gly Tyr Ala Phe
        35                  40                  45

Thr Asp Tyr Leu Ile Glu Trp Val Lys Gln Arg Pro Gly Gln Gly Leu
    50                  55                  60

Glu Trp Ile Gly Val Ile Asn Pro Val Arg Gly Thr Thr Asn Tyr Ser
65                  70                  75                  80

Glu Lys Phe Lys Gly Lys Ala Thr Leu Thr Ala Asp Lys Ser Ser Gly
                85                  90                  95

Thr Ala Tyr Met Gln Phe Tyr Ser Leu Thr Ser Asp Asp Ser Ala Val
            100                 105                 110

Tyr Phe Cys Ala Arg Ser Arg Gly Ser Asp Gly Phe Pro Tyr Trp Gly
        115                 120                 125

Gln Gly Thr Leu Val Thr Val Ser Ala
    130                 135

```
<210> SEQ ID NO 60
<211> LENGTH: 118
<212> TYPE: PRT
<213> ORGANISM: Artificial Sequence
<220> FEATURE:
<223> OTHER INFORMATION: mAb 27C9B5 AA heavy chain (-leader sequence)

<400> SEQUENCE: 60

Gln Val Gln Val Arg Gln Ser Gly Ala Glu Val Val Arg Pro Gly Thr
1               5                   10                  15

Ser Val Arg Val Ser Cys Lys Thr Ser Gly Tyr Ala Phe Thr Asp Tyr
            20                  25                  30

Leu Ile Glu Trp Val Lys Gln Arg Pro Gly Gln Gly Leu Glu Trp Ile
        35                  40                  45

Gly Val Ile Asn Pro Val Arg Gly Thr Thr Asn Tyr Ser Glu Lys Phe
    50                  55                  60

Lys Gly Lys Ala Thr Leu Thr Ala Asp Lys Ser Ser Gly Thr Ala Tyr
65                  70                  75                  80

Met Gln Phe Tyr Ser Leu Thr Ser Asp Ser Ala Val Tyr Phe Cys
                85                  90                  95

Ala Arg Ser Arg Gly Ser Asp Gly Phe Pro Tyr Trp Gly Gln Gly Thr
            100                 105                 110

Leu Val Thr Val Ser Ala
        115

<210> SEQ ID NO 61
<211> LENGTH: 19
<212> TYPE: PRT
<213> ORGANISM: Artificial Sequence
<220> FEATURE:
<223> OTHER INFORMATION: mAb 27C9B5 AA heavy chain leader sequence

<400> SEQUENCE: 61

Met Gly Trp Ser Gly Val Phe Ile Phe Leu Leu Ser Val Thr Ala Gly
1               5                   10                  15

Val His Ser

<210> SEQ ID NO 62
<211> LENGTH: 30
<212> TYPE: PRT
<213> ORGANISM: Artificial Sequence
<220> FEATURE:
<223> OTHER INFORMATION: mAb 27C9B5 AA heavy chain framework region 1

<400> SEQUENCE: 62

Gln Val Gln Val Arg Gln Ser Gly Ala Glu Val Val Arg Pro Gly Thr
1               5                   10                  15

Ser Val Arg Val Ser Cys Lys Thr Ser Gly Tyr Ala Phe Thr
            20                  25                  30

<210> SEQ ID NO 63
<211> LENGTH: 5
<212> TYPE: PRT
<213> ORGANISM: Artificial Sequence
<220> FEATURE:
<223> OTHER INFORMATION: mAb 27C9B5 AA heavy chain CDR1

<400> SEQUENCE: 63

Asp Tyr Leu Ile Glu
1               5
```

```
<210> SEQ ID NO 64
<211> LENGTH: 14
<212> TYPE: PRT
<213> ORGANISM: Artificial Sequence
<220> FEATURE:
<223> OTHER INFORMATION: mAb 27C9B5 AA heavy chain framework region 2

<400> SEQUENCE: 64

Trp Val Lys Gln Arg Pro Gly Gln Gly Leu Glu Trp Ile Gly
1               5                   10

<210> SEQ ID NO 65
<211> LENGTH: 17
<212> TYPE: PRT
<213> ORGANISM: Artificial Sequence
<220> FEATURE:
<223> OTHER INFORMATION: mAb 27C9B5 AA heavy chain CDR2

<400> SEQUENCE: 65

Val Ile Asn Pro Val Arg Gly Thr Thr Asn Tyr Ser Glu Lys Phe Lys
1               5                   10                  15

Gly

<210> SEQ ID NO 66
<211> LENGTH: 32
<212> TYPE: PRT
<213> ORGANISM: Artificial Sequence
<220> FEATURE:
<223> OTHER INFORMATION: mAb 27C9B5 AA heavy chain framework region 3

<400> SEQUENCE: 66

Lys Ala Thr Leu Thr Ala Asp Lys Ser Ser Gly Thr Ala Tyr Met Gln
1               5                   10                  15

Phe Tyr Ser Leu Thr Ser Asp Asp Ser Ala Val Tyr Phe Cys Ala Arg
            20                  25                  30

<210> SEQ ID NO 67
<211> LENGTH: 9
<212> TYPE: PRT
<213> ORGANISM: Artificial Sequence
<220> FEATURE:
<223> OTHER INFORMATION: mAb 27C9B5 AA heavy chain CDR3

<400> SEQUENCE: 67

Ser Arg Gly Ser Asp Gly Phe Pro Tyr
1               5

<210> SEQ ID NO 68
<211> LENGTH: 11
<212> TYPE: PRT
<213> ORGANISM: Artificial Sequence
<220> FEATURE:
<223> OTHER INFORMATION: mAb 27C9B5 AA heavy chain framework region 4

<400> SEQUENCE: 68

Trp Gly Gln Gly Thr Leu Val Thr Val Ser Ala
1               5                   10

<210> SEQ ID NO 69
<211> LENGTH: 393
<212> TYPE: DNA
<213> ORGANISM: Artificial Sequence
<220> FEATURE:
<223> OTHER INFORMATION: mAb 27C9B5 DNA light chain (+leader sequence)

<400> SEQUENCE: 69
```

```
atgaagttgc ctgttaggct gttggtgctg atgttctgga ttcctgcttc cagcagtgat    60
gttttgatga cccaaactcc actctccctg cctgtcagtc ttggagatca agcctccatc   120
tcttgcagat ctagtcagag cattgtacat agtaatggat acacctattt agagtggtac   180
ctgcagaaac caggccagtc tccaaagctc cttatctaca aactttccaa ccgattttct   240
ggggtcccag acaggttcag tggcagtgga tcagggacag atttcacact aagatcagc   300 cgagtggagg ctgaggatct gggagtttat tactgctttc aaggttcaca tattccgtac   360
acgttcggag gggggaccaa gttggaaata aaa                                393
```

<210> SEQ ID NO 70
<211> LENGTH: 336
<212> TYPE: DNA
<213> ORGANISM: Artificial Sequence
<220> FEATURE:
<223> OTHER INFORMATION: mAb 27C9B5 DNA light chain (-leader sequence)

<400> SEQUENCE: 70

```
gatgttttga tgacccaaac tccactctcc ctgcctgtca gtcttggaga tcaagcctcc    60
atctcttgca gatctagtca gagcattgta catagtaatg gatacaccta tttagagtgg   120
tacctgcaga aaccaggcca gtctccaaag ctccttatct acaaactttc caaccgattt   180
tctggggtcc cagacaggtt cagtggcagt ggatcaggga cagatttcac acttaagatc   240
agccgagtgg aggctgagga tctgggagtt tattactgct ttcaaggttc acatattccg   300
tacacgttcg gaggggggac caagttggaa ataaaa                              336
```

<210> SEQ ID NO 71
<211> LENGTH: 57
<212> TYPE: DNA
<213> ORGANISM: Artificial Sequence
<220> FEATURE:
<223> OTHER INFORMATION: mAb 27C9B5 DNA light chain leader sequence

<400> SEQUENCE: 71

```
atgaagttgc ctgttaggct gttggtgctg atgttctgga ttcctgcttc cagcagt      57
```

<210> SEQ ID NO 72
<211> LENGTH: 69
<212> TYPE: DNA
<213> ORGANISM: Artificial Sequence
<220> FEATURE:
<223> OTHER INFORMATION: mAb 27C9B5 DNA light chain framework region 1

<400> SEQUENCE: 72

```
gatgttttga tgacccaaac tccactctcc ctgcctgtca gtcttggaga tcaagcctcc    60
atctcttgc                                                           69
```

<210> SEQ ID NO 73
<211> LENGTH: 48
<212> TYPE: DNA
<213> ORGANISM: Artificial Sequence
<220> FEATURE:
<223> OTHER INFORMATION: mAb 27C9B5 DNA light chain CDR1

<400> SEQUENCE: 73

```
agatctagtc agagcattgt acatagtaat ggatacacct atttagag               48
```

<210> SEQ ID NO 74
<211> LENGTH: 45
<212> TYPE: DNA

```
<213> ORGANISM: Artificial Sequence
<220> FEATURE:
<223> OTHER INFORMATION: mAb 27C9B5 DNA light chain framework region 2

<400> SEQUENCE: 74
tggtacctgc agaaaccagg ccagtctcca aagctcctta tctac          45

<210> SEQ ID NO 75
<211> LENGTH: 21
<212> TYPE: DNA
<213> ORGANISM: Artificial Sequence
<220> FEATURE:
<223> OTHER INFORMATION: mAb 27C9B5 DNA light chain CDR2

<400> SEQUENCE: 75
aaactttcca accgattttc t                                    21

<210> SEQ ID NO 76
<211> LENGTH: 96
<212> TYPE: DNA
<213> ORGANISM: Artificial Sequence
<220> FEATURE:
<223> OTHER INFORMATION: mAb 27C9B5 DNA light chain framework region 3

<400> SEQUENCE: 76
ggggtcccag acaggttcag tggcagtgga tcagggacag atttcacact taagatcagc    60
cgagtggagg ctgaggatct gggagtttat tactgc                            96

<210> SEQ ID NO 77
<211> LENGTH: 27
<212> TYPE: DNA
<213> ORGANISM: Artificial Sequence
<220> FEATURE:
<223> OTHER INFORMATION: mAb 27C9B5 DNA light chain CDR3

<400> SEQUENCE: 77
tttcaaggtt cacatattcc gtacacg                              27

<210> SEQ ID NO 78
<211> LENGTH: 30
<212> TYPE: DNA
<213> ORGANISM: Artificial Sequence
<220> FEATURE:
<223> OTHER INFORMATION: mAb 27C9B5 DNA light chain framework region 4

<400> SEQUENCE: 78
ttcggagggg ggaccaagtt ggaaataaaa                           30

<210> SEQ ID NO 79
<211> LENGTH: 131
<212> TYPE: PRT
<213> ORGANISM: Artificial Sequence
<220> FEATURE:
<223> OTHER INFORMATION: mAb 27C9B5 AA light chain (+leader sequence)

<400> SEQUENCE: 79

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Tyr Thr Tyr Leu Glu Trp Tyr Leu Gln Lys Pro
    50                  55                  60
```

Gly Gln Ser Pro Lys Leu Leu Ile Tyr Lys Leu Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Ile Pro Tyr Thr Phe Gly Gly Gly Thr Lys Leu
        115                 120                 125

Glu Ile Lys
    130

<210> SEQ ID NO 80
<211> LENGTH: 112
<212> TYPE: PRT
<213> ORGANISM: Artificial Sequence
<220> FEATURE:
<223> OTHER INFORMATION: mAb 27C9B5 AA light chain (-leader sequence)

<400> SEQUENCE: 80

Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
            20                  25                  30

Asn Gly Tyr Thr Tyr Leu Glu Trp Tyr Leu Gln Lys Pro Gly Gln Ser
        35                  40                  45

Pro Lys Leu Leu Ile Tyr Lys Leu Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Ile Pro Tyr Thr Phe Gly Gly Gly Thr Lys Leu Glu Ile Lys
        100                 105                 110

<210> SEQ ID NO 81
<211> LENGTH: 19
<212> TYPE: PRT
<213> ORGANISM: Artificial Sequence
<220> FEATURE:
<223> OTHER INFORMATION: mAb 27C9B5 AA light chain leader sequence

<400> SEQUENCE: 81

Met Lys Leu Pro Val Arg Leu Leu Val Leu Met Phe Trp Ile Pro Ala
1               5                   10                  15

Ser Ser Ser

<210> SEQ ID NO 82
<211> LENGTH: 23
<212> TYPE: PRT
<213> ORGANISM: Artificial Sequence
<220> FEATURE:
<223> OTHER INFORMATION: mAb 27C9B5 AA light chain framework region 1

<400> SEQUENCE: 82

Asp Val Leu Met Thr Gln Thr Pro Leu Ser Leu Pro Val Ser Leu Gly
1               5                   10                  15

Asp Gln Ala Ser Ile Ser Cys
            20

```
<210> SEQ ID NO 83
<211> LENGTH: 16
<212> TYPE: PRT
<213> ORGANISM: Artificial Sequence
<220> FEATURE:
<223> OTHER INFORMATION: mAb 27C9B5 AA light chain CDR1

<400> SEQUENCE: 83

Arg Ser Ser Gln Ser Ile Val His Ser Asn Gly Tyr Thr Tyr Leu Glu
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: mAb 27C9B5 AA light chain framework region 2

<400> SEQUENCE: 84

Trp Tyr Leu Gln Lys Pro Gly Gln Ser Pro Lys Leu Leu Ile Tyr
1               5                   10                  15

<210> SEQ ID NO 85
<211> LENGTH: 7
<212> TYPE: PRT
<213> ORGANISM: Artificial Sequence
<220> FEATURE:
<223> OTHER INFORMATION: mAb 27C9B5 AA light chain CDR2

<400> SEQUENCE: 85

Lys Leu Ser Asn Arg Phe Ser
1               5

<210> SEQ ID NO 86
<211> LENGTH: 32
<212> TYPE: PRT
<213> ORGANISM: Artificial Sequence
<220> FEATURE:
<223> OTHER INFORMATION: mAb 27C9B5 AA light chain framework region 3

<400> SEQUENCE: 86

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
                20                  25                  30

<210> SEQ ID NO 87
<211> LENGTH: 9
<212> TYPE: PRT
<213> ORGANISM: Artificial Sequence
<220> FEATURE:
<223> OTHER INFORMATION: mAb 27C9B5 AA light chain CDR3

<400> SEQUENCE: 87

Phe Gln Gly Ser His Ile Pro Tyr Thr
1               5

<210> SEQ ID NO 88
<211> LENGTH: 10
<212> TYPE: PRT
<213> ORGANISM: Artificial Sequence
<220> FEATURE:
<223> OTHER INFORMATION: mAb 27C9B5 AA light chain framework region 4

<400> SEQUENCE: 88

Phe Gly Gly Gly Thr Lys Leu Glu Ile Lys
1               5                   10
```

<210> SEQ ID NO 89
<211> LENGTH: 350
<212> TYPE: PRT
<213> ORGANISM: Plasmodium vivax
<220> FEATURE:
<221> NAME/KEY: MISC_FEATURE
<222> LOCATION: (1)..(350)
<223> OTHER INFORMATION: P. vivax PSSP17

<400> SEQUENCE: 89

Met Pro Phe His Phe Ser Lys Thr Trp Cys Leu Ile Phe Leu Tyr Phe
1               5                   10                  15

Tyr Phe Lys Thr Gln Ile Glu Cys Tyr Gln Asp Asp Pro Lys Leu Pro
            20                  25                  30

Glu Cys Asp Val Ser Ile Asp Thr Ala Ile Cys Ile Asn Asn Gly Gln
        35                  40                  45

Lys Ile Leu Leu Pro Glu Ala Lys Pro Tyr Gly Ile Ser Ala His Ile
    50                  55                  60

Lys Phe Asp Ser Ile Ser Ala Val Asp Ala Thr Gly Asn Arg Asn His
65                  70                  75                  80

Ala Val Gly Asn Phe Phe Ala Ser Thr Gly Phe Gly Gly Met Gly Asn
                85                  90                  95

Ser Ser Leu Phe Arg Lys Asn Tyr Ile Tyr Ile Pro His Ser Asp Glu
            100                 105                 110

Tyr Phe Lys Thr Val Asp Phe Ser Tyr Thr Phe Phe Ile Tyr Leu Leu
        115                 120                 125

Glu Asp Glu Leu Ser Ile Lys Asn Asn Val Glu Met Phe Cys Pro
    130                 135                 140

Val Ile His Lys Gly Ile Ile Lys Asp Lys Val Gln Glu Ser Ser Pro
145                 150                 155                 160

Ala Ile Leu Ile Asn Ala Lys Asn Gly Arg Ile Lys Ile Val Leu Ser
                165                 170                 175

Thr Ser Ser Ser Thr Asn Ser Ala Gly Glu Glu Phe Leu Ser Asn Phe
            180                 185                 190

Lys Leu Arg Arg His Gln Trp Tyr His Val Ala Val Arg His Ile
        195                 200                 205

Asn His Val Arg Leu Phe Val Asn Gly Ile Leu Asp Ser Ser Phe Leu
    210                 215                 220

Thr Glu Gly Ile Thr Lys Thr Asn Asp Phe Pro Ile Tyr Ile Gly Gly
225                 230                 235                 240

Ala Pro Tyr Ser Val Glu Ser Cys Asp Phe Pro Leu Leu Asp Glu
                245                 250                 255

Leu Lys Tyr Asn Leu Ser Leu Gly Val Asp His Ile Gln Ser Glu
            260                 265                 270

Ala Ala Ser Thr Leu Asn Gly Val Glu Pro Ser Phe Ile Tyr Phe Gly
        275                 280                 285

Cys Phe His Cys Asp Ile Asn Asn Ala Ile Leu Ser Cys Pro Asn Asn
    290                 295                 300

Tyr His Leu Cys Asn Lys Val Glu Leu Tyr Ile Gly Val Tyr Asn Val
305                 310                 315                 320

Met Arg Lys Phe Ser Leu Asn Ile Asn Asn Leu Ile Leu Pro Phe Ser
                325                 330                 335

Pro Glu Asn His Thr Gly Ile Gly Val Cys Cys Ala Asp Ile
            340                 345                 350

<210> SEQ ID NO 90
<211> LENGTH: 348
<212> TYPE: PRT
<213> ORGANISM: Plasmodium falciparum
<220> FEATURE:
<221> NAME/KEY: MISC_FEATURE
<222> LOCATION: (1)..(348)
<223> OTHER INFORMATION: P. falciparum PSSP17

<400> SEQUENCE: 90

Met Leu Leu Tyr Leu Tyr Lys Ile Trp Tyr Leu Ile Leu Leu Trp Leu
1               5                   10                  15

Tyr Thr His Asn Gln Tyr Lys Cys Asp Leu Arg Lys Pro Pro Glu Cys
                20                  25                  30

Asp Val Ser Ile Asp Thr Ser Ile Cys Ile Asn Asn Gly Gln Lys Ile
            35                  40                  45

Leu Leu Pro Ser Ala Lys Pro Tyr Gly Ile Ser Thr His Ile Thr Phe
        50                  55                  60

Asp Ser Leu Met Pro Val Asp Ser Thr Gly Asn Arg Asn His Ala His
65                  70                  75                  80

Gly Lys Phe Phe Ala Ser Ser Gly Phe Gly Ile Gly Asn Ser Ala
                85                  90                  95

Leu Phe Arg Gln Asn Tyr Ile Tyr Ile Pro His Ser Asp Glu Tyr Phe
            100                 105                 110

Lys Ser Val Asp Phe Ser Tyr Thr Phe Phe Ile Tyr Leu Leu Gln Asp
        115                 120                 125

Glu Ile Ser Arg Lys Asn Asn Met Glu Glu Lys Phe Cys Pro Val Ile
130                 135                 140

His Lys Gly Ile Ile Lys Asp Lys Ile Gln Glu Ser Ser Pro Ala Ile
145                 150                 155                 160

Leu Ile Asn Thr Lys Asn Gly Arg Ile Lys Ile Val Leu Ser Thr Ser
                165                 170                 175

Ser Ser Thr Asn Ser Ala Gly Glu Glu Phe Leu Ser Asn Phe Lys Leu
            180                 185                 190

Arg His His Gln Trp Tyr His Met Thr Val Val Arg His Ile Asn His
        195                 200                 205

Val Arg Leu Phe Val Asp Gly Ile Leu Asp Ser Ser Phe Leu Thr Glu
210                 215                 220

Gly Ile Thr Lys Thr Asn Asp Ser Pro Ile Tyr Ile Gly Gly Ala Pro
225                 230                 235                 240

Tyr Ser Val Asp Ser Cys Asp Phe Pro Phe Leu Leu Asp Glu Leu Lys
                245                 250                 255

Ile Tyr Asn Leu Ser Ile Gly Thr Asp Gln Ile Gln Ser Glu Ala Ser
            260                 265                 270

Ala Ser Leu Ser Gly Ile Glu Pro Ser Phe Ile Tyr Phe Gly Cys Phe
        275                 280                 285

His Cys Asp Met Asn Thr Ala Ile Leu Ser Cys Pro Asn Asn Tyr His
290                 295                 300

Leu Cys Asn Lys Met Glu Leu Tyr Ile Gly Val Tyr Asn Val Leu Arg
305                 310                 315                 320

Lys Phe Ser Leu Asp Val Asn Asn Ile Ile Leu Pro Tyr Ser Ser Glu
                325                 330                 335

Ser Asn Leu Gly Ile Gly Ile Cys Cys Thr Asp Ile
            340                 345